US010071158B2

(12) United States Patent
Heiss et al.

(10) Patent No.: US 10,071,158 B2
(45) Date of Patent: *Sep. 11, 2018

(54) COMBINATION OF THE APPLICATION OF ANTIBODIES FOR IMMUNOSTIMULATION TOGETHER WITH GLUCOCORTICOIDS

(71) Applicant: Lindis Biotech GmbH, Martinsried (DE)

(72) Inventors: Markus M. Heiss, Pöcking (DE); Horst Lindhofer, Munich (DE)

(73) Assignee: LINDIS BIOTECH GMBH, Martinsried (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/247,029

(22) Filed: Apr. 7, 2014

(65) Prior Publication Data
US 2015/0086550 A1 Mar. 26, 2015

Related U.S. Application Data

(63) Continuation of application No. 11/977,856, filed on Oct. 26, 2007, now Pat. No. 8,709,421, which is a continuation-in-part of application No. PCT/EP2005/004468, filed on Apr. 26, 2005.

(51) Int. Cl.
| A61K 39/00 | (2006.01) |
| A61K 39/395 | (2006.01) |
| A61K 31/573 | (2006.01) |
| C07K 16/28 | (2006.01) |
| C07K 16/30 | (2006.01) |
| C07K 16/32 | (2006.01) |
| A61K 45/06 | (2006.01) |

(52) U.S. Cl.
CPC ........ *A61K 39/3955* (2013.01); *A61K 31/573* (2013.01); *A61K 39/0011* (2013.01); *A61K 45/06* (2013.01); *C07K 16/2809* (2013.01); *C07K 16/30* (2013.01); *C07K 16/32* (2013.01); *A61K 2039/505* (2013.01); *C07K 2317/31* (2013.01)

(58) Field of Classification Search
None
See application file for complete search history.

(56) References Cited

U.S. PATENT DOCUMENTS

| 5,496,804 A * | 3/1996 | Reed .................. A61K 38/193 424/85.1 |
| 5,677,174 A | 10/1997 | Dinsmore |
| 5,869,045 A | 2/1999 | Hellstrom |
| 5,945,311 A | 8/1999 | Lindhofer |
| 5,985,276 A | 11/1999 | Lindhofer |
| 6,007,807 A | 12/1999 | Mocikat |
| 6,020,145 A | 2/2000 | Hellstrom |
| 6,030,615 A | 2/2000 | Bucala et al. |
| 6,134,982 A | 10/2000 | Takabatake |
| 6,172,213 B1 | 1/2001 | Lowman |
| 6,183,744 B1 | 2/2001 | Goldenberg |
| 6,210,668 B1 | 4/2001 | Lindhofer |
| 6,294,167 B1 | 9/2001 | Lindhofer |
| 6,306,393 B1 | 10/2001 | Goldenberg |
| 6,322,787 B1 | 11/2001 | Mocikat |
| 6,551,592 B2 | 4/2003 | Lindhofer et al. |
| 6,761,889 B2 | 7/2004 | Lowman |
| 6,962,702 B2 | 11/2005 | Hansen |
| 6,994,853 B1 | 2/2006 | Lindhofer |
| 7,018,632 B2 | 3/2006 | Lindhofer |
| 7,074,403 B1 | 7/2006 | Goldenberg |
| 7,125,541 B2 | 10/2006 | Thorpe et al. |
| 7,157,085 B2 | 1/2007 | Lowman |
| 7,262,028 B2 | 8/2007 | Van Berkel |
| 7,312,318 B2 | 12/2007 | Hansen |
| 7,378,386 B2 | 5/2008 | Thorpe |
| 7,407,656 B2 | 8/2008 | Reiter |
| 7,438,907 B2 | 10/2008 | Schuurman |
| 7,462,352 B2 | 12/2008 | Hansen |
| 7,482,013 B2 | 1/2009 | Ballance |
| 7,494,646 B2 | 2/2009 | Jakobovits |
| 7,521,056 B2 | 4/2009 | Chang |
| 7,534,427 B2 | 5/2009 | Goldenberg et al. |
| 7,534,431 B2 | 5/2009 | McBride |

(Continued)

FOREIGN PATENT DOCUMENTS

| CA | 2397169 | 2/2004 |
| CA | 2402930 | 3/2004 |

(Continued)

OTHER PUBLICATIONS

Schmidt et al., The effect of different corticosteroids and cycloporin A on interleukin-4 and interleukin-5 release from murine $T_H2$-type T cells, European Journal of Pharmacology, 1994, vol. 260, No. 2-3, pp. 247-250 Exhibit 9.
Schweizer et al., Efficient carcinoma cell killing by activated polymorphonuclear neutrophils targeted with an Ep-CAMxCD64 (HEA125x197) bispecific antibody, Cancer Immunology and Immunotherapy, 2002, vol. 51, No. 11-12, pp. 621-629 Exhibit 10.
Armstrong, Andrew and Stephen L. Eck, "EpCAM: A New Therapeutic Target for an Old Cancer Antigen," *Cancer Biology & Therapy*, 2003, 2:320-6.
de Gast, Gijsbert C. et al., "CD8 T cell activation after intravenous administration of CD3 x CD19 bispecific antibody in patients with non-Hodgkin lymphoma," *Cancer Immunol Immunother*, 1995, 40:390-6.
Hess, Ch. et al., "Immunological Monitoring of Locoregional Infusion Chemotherapy in Patients with Liver Metastases of Colorectal Carcinoma," *Journal of Cancer Research and Clinical Oncology*, 1986, 111(Supp 1):S100, Abstract Liv 20.
Jung, Gundram et al., "Local Immunotherapy of Glioma Patients with a Combination of 2 Bispecific Antibody Fragments and Resting Autologous Lymphocytes: Evidence for In Situ T-Cell Activation and Therapeutic Efficacy," *Int. J. Cancer*, 2001, 91:225-30.

(Continued)

*Primary Examiner* — Hong Sang
(74) *Attorney, Agent, or Firm* — Fitch Even Tabin & Flannery, LLP

(57) ABSTRACT

The present invention relates to methods for reducing or eliminating the non-specific release of a cytokine associated with a disease comprising administering at least one glucocorticoid and an immunostimulating antibody. Additionally, the present invention relates to a pharmaceutical composition that contains at least one immunostimulating antibody and at least one glucocorticoid.

20 Claims, 39 Drawing Sheets

(56) References Cited

U.S. PATENT DOCUMENTS

| | | |
|---|---|---|
| 7,538,195 B2 | 5/2009 | Singh |
| 7,576,101 B2 | 8/2009 | Karlik |
| 7,604,799 B2 | 10/2009 | Kinch |
| 7,635,472 B2 | 12/2009 | Kufer |
| 7,641,901 B2 | 1/2010 | Goldenberg |
| 7,772,209 B2 | 8/2010 | Niyikiza |
| 7,910,103 B2 | 3/2011 | Goldenberg |
| 7,947,459 B2 | 5/2011 | Hubert |
| 8,012,470 B2 | 9/2011 | Lindhofer |
| 8,066,989 B2 | 11/2011 | Lindhofer |
| 8,268,617 B2 | 9/2012 | Singh |
| 8,277,806 B2 | 10/2012 | Lindhofer |
| 8,383,081 B2 | 2/2013 | Hansen |
| 8,530,627 B2 | 9/2013 | Koenig |
| 8,663,638 B2 | 3/2014 | Lindhofer |
| 8,784,821 B1 | 7/2014 | Kufer |
| 8,889,135 B2 | 11/2014 | Fischkoff |
| 9,017,676 B2 | 4/2015 | Lindhofer |
| 9,605,242 B2 | 3/2017 | Lindhofer |
| 9,750,806 B2 | 9/2017 | Lindhofer |
| 9,772,327 B2 | 9/2017 | Lindhofer |
| 2001/0018041 A1 | 8/2001 | Hanna |
| 2002/0004497 A1* | 1/2002 | Tolonen ............... A61K 45/06 514/169 |
| 2002/0006404 A1 | 1/2002 | Hanna |
| 2002/0012665 A1 | 1/2002 | Hanna |
| 2002/0028178 A1 | 3/2002 | Hanna |
| 2002/0037289 A1 | 3/2002 | Thorpe et al. |
| 2002/0041847 A1 | 4/2002 | Goldenberg |
| 2002/0159996 A1 | 10/2002 | Hariharan |
| 2003/0086924 A1 | 5/2003 | Sliwkowski |
| 2003/0180292 A1 | 9/2003 | Hanna |
| 2003/0223999 A1 | 12/2003 | Lindhofer |
| 2004/0043029 A1 | 3/2004 | Hellstrom |
| 2004/0137612 A1 | 7/2004 | Baksh |
| 2004/0197324 A1 | 10/2004 | Liu |
| 2004/0219155 A1 | 11/2004 | Thorpe |
| 2004/0219203 A1 | 11/2004 | Griffiths |
| 2005/0002941 A1 | 1/2005 | Thorpe |
| 2005/0003403 A1 | 1/2005 | Rossi |
| 2005/0004349 A1 | 1/2005 | Hubert |
| 2005/0013819 A1 | 1/2005 | Kinch |
| 2005/0031620 A1 | 2/2005 | Thorpe |
| 2005/0043233 A1 | 2/2005 | Stefanic et al. |
| 2005/0070693 A1* | 3/2005 | Hansen ............... C07K 16/2887 530/388.22 |
| 2005/0079184 A1 | 4/2005 | Hsing-Chang |
| 2005/0084490 A1 | 4/2005 | Adams |
| 2005/0090659 A1 | 4/2005 | Herrmann |
| 2005/0118164 A1 | 6/2005 | Herman |
| 2005/0123536 A1 | 6/2005 | Law |
| 2005/0129696 A1 | 6/2005 | Thorpe |
| 2005/0163782 A1 | 7/2005 | Glaser |
| 2005/0180972 A1 | 8/2005 | Wahl |
| 2005/0215472 A1 | 9/2005 | Schulke |
| 2007/0116820 A1 | 5/2007 | Prakash |
| 2009/0232812 A1 | 9/2009 | Kufe |
| 2010/0266496 A1 | 10/2010 | Hansen |
| 2017/0224818 A1 | 8/2017 | Lindhofer |

FOREIGN PATENT DOCUMENTS

| | | |
|---|---|---|
| CA | 2414148 | 6/2004 |
| CN | 1311257 | 9/2001 |
| CN | 1169837 | 10/2004 |
| CN | 101331151 | 12/2008 |
| DE | 10156910 | 6/2003 |
| DE | 10209564 | 9/2003 |
| JP | 2007-287008 A | 10/1995 |
| JP | 2008-114588 A | 5/1996 |
| JP | 2002-540078 A | 11/2002 |
| JP | 2004-500412 A | 1/2004 |
| JP | 2009-500363 A | 8/2009 |
| WO | 1998042378 | 10/1998 |
| WO | 1999001556 | 1/1999 |
| WO | WO 99/54440 | 10/1999 |
| WO | 1999066951 | 12/1999 |
| WO | 2000074718 | 12/2000 |
| WO | 2001005427 | 1/2001 |
| WO | WO 01/34194 | 5/2001 |
| WO | 2001077137 | 10/2001 |
| WO | WO 02/004021 | 1/2002 |
| WO | 2002022685 | 3/2002 |
| WO | WO 02/064634 | 8/2002 |
| WO | 2002072141 | 9/2002 |
| WO | 2002074938 | 9/2002 |
| WO | 2002086104 | 10/2002 |
| WO | 2003022995 | 3/2003 |
| WO | WO 03/030835 | 4/2003 |
| WO | 2003034903 | 5/2003 |
| WO | 2003044035 | 5/2003 |
| WO | WO 03/043583 | 5/2003 |
| WO | 2003074567 | 9/2003 |
| WO | 2003106621 | 12/2003 |
| WO | 2004004658 | 1/2004 |
| WO | 2004004661 | 1/2004 |
| WO | 2004006847 | 1/2004 |
| WO | 2004009618 | 1/2004 |
| WO | 2004016750 | 2/2004 |
| WO | 2004032828 | 4/2004 |
| WO | 2004045512 | 6/2004 |
| WO | 2004058298 | 7/2004 |
| WO | 2004066931 | 8/2004 |
| WO | 2004066932 | 8/2004 |
| WO | WO 2004/071404 | 8/2004 |
| WO | 2004074434 | 9/2004 |
| WO | 2004094613 | 11/2004 |
| WO | WO 2004/105737 | 12/2004 |
| WO | WO 2004/106381 | 12/2004 |
| WO | 2005000898 | 1/2005 |
| WO | 2005000899 | 1/2005 |
| WO | 2005012493 | 2/2005 |
| WO | 2005014618 | 2/2005 |
| WO | WO 2005/027839 | 3/2005 |
| WO | WO 2006/089133 | 8/2006 |
| WO | 2007068354 | 6/2007 |
| WO | 2007120656 | 10/2007 |
| WO | 2012055961 | 5/2012 |
| WO | 2012062596 | 5/2012 |
| WO | 2013083809 | 6/2013 |

OTHER PUBLICATIONS

Marmé, Alexander et al. "Intraperitoneal Bispecific Antibody (HEA125XOKT3) Therapy Inhibits Malignant Ascites Production in Advanced Ovarian Carcinoma," *Int. J. Cancer*, 2002, 101:183-9.

Metzler, Bernhard et al., "Inhibition of Arteriosclerosis by T-Cell Depletion in Normocholesterolemic Rabbits Immunized with Heat Shock Protein 65," *Arteriosclerosis, Thrombosis and Vascular Biology*, 1999, 19:1905-11.

Poczatek, Robert B. et al., "Ep-CAM Levels in Prostatic Adenocarcinoma and Prostatic Intraepithelial Neoplasia," *The Journal of Urology*, 1999, 162:1462-6.

Schmitt, M. et al., "Opsonization with a trifunctional bispecific (αCD3 x αEpCAM) antibody results in efficient lysis in vitro and in vivo of EpCAM positive tumor cells by cytotoxic T lymphocytes," *International Journal of Oncology*, 2004, 25:841-8.

FDA website extract showing the approval history of alemtuzumab accessed on Dec. 23, 2013.

Hartmann F et al., Treatment of refractory Hodgkin's disease with an anti-CD16/CD30 bispecific antibody, Blood. Mar. 15, 1997;89(6):2042-7.

Lillehei KO et al., Long-term follow-up of patients with recurrent malignant gliomas treated with adjuvant adoptive immunotherapy, Neurosurgery. Jan. 1991;28(1):16-23.

Merchant AM et al., An efficient route to human bispecific IgG, Nat Biotechnol. Jul. 1998;16(7):677-81.

Nielsen HJ et al., Effect of ranitidine on postoperative suppression of natural killer cell activity and delayed hypersensitivity, Acta Chir Scand. Aug. 1989;155(8):377-82.

(56) References Cited

OTHER PUBLICATIONS

Rose AL et al., Glucocorticoids and rituximab in vitro: synergistic direct antiproliferative and apoptotic effects, Blood. Sep. 1, 2002;100(5):1765-73.
Scheinfeld et al., Dermatology Journal online, 2003, vol. 9(2).
Sebastian M. et al, Treatment of non-small cell lung cancer patients with the trifunctional monoclonal antibody catumaxomab (anti-EpCAM x anti-CD3): a phase I study, Cancer Immunol Immunother. Oct. 2007;56(10):1637-44. Epub Apr. 5, 2007.
Thierfelder S. et al., Bispecific antibodies target operationally tumor-specific antigens in two leukemia relapse models, Blood. Dec. 15, 1996;88(12):4651-8.
Walsh et al., Cleveland Clinic Journal of Medicine, 1992, vol. 59 No. 5, 505-514.
Walz A. et al., Antitumour effects of a bispecific trivalent antibody in multicellular tumour spheroids, Anticancer Res. Mar-Apr. 2004;24(2B):887-93.
Walz A. et al., Prednisolone reduces TNF-alpha release by PBMCs activated with a trifunctional bispecific antibody but not their anti-tumor activity, Anticancer Res. Nov.-Dec. 2005;25(6B):4239-43.
Wikipedia entry for 'corticosteroid', as at Apr. 17, 2005.
Wikipedia entry for 'trifunctional antibody', as at Nov. 2009.
Wikipedia revision history for 'trifunctional antibody' as of Dec. 2013.
Zeidler R. et al., Simultaneous activation of T cells and accessory cells by a new class of intact bispecific antibody results in efficient tumor cell killing, J. Immunol. Aug. 1, 1999;163(3):1246-52.
Summons to Oral Proceedings Under Rule 115(1) EPC, EPC Patent No. 1874821 dated Jun. 29, 2016. (English Language Translation Enclosed.).
Amgen Opposition to the European Patent EP 1874 821 dated Jan. 17, 2014. (English Language Translation Enclosed.).
Strawman Opposition to European Patent 1874821 dated Feb. 9, 2016. (English Language Translation Enclosed.).
Notice of Opposition to a European Patent, EP1874821 dated Jan. 17, 2014.
Lindis Response to Opponents' Submission of Mar. 17, 2017, dated Mar. 8, 2017.
Submission of Opponents Strawman/Amgen in relation to EP Opposition of EP Patent No. 1874821 (dated Mar. 7, 2017).
Sebatian thesis, Sections 4.1 and 4.2 (previously cited on Apr. 7, 2014).
Prmotionsordnung des Fachbereichs Medizin der Johannes Guttenberg-Universität Maninz, In Der Fassung vom May 2, 1989 (9 pages).
Ackerman, George L. et al., "Adrenocortical Responsiveness After Alternate-Day Corticosteroid Therapy." The New England Journal of Medicine, Feb. 22, 1968, vol. 278, No. 8, pp. 405-409.
Borchmann, et al., "Monoclonal antibody-based immunotherapy of Hodgkin's lymphoma." Current Opinion in Investigational Drugs, Dec. 2004, vol. 5, No. 12, pp. 1262-1267, Abstract only.
Brandi, Christian, et al., "The Effect of Dexamethasone on Polyclonal T Cell Activation and Redirected Target Cell Lysis As Induced by a CD19/CD3-Bispecific Single-Chain Antibody Construct." Cancer Immunology Immunotherapy, 2007, volume, 56, No. 10, 1551-1563, 13 pages.
Breslin, Sheila, "Cytokine-Release Syndrome: Overview and Nursing Implications." Clinical Journal of Oncology Nursing, Supplement to vol. 11, No. 1, pp. 37-42, abstract only (p. 37), 2007.
Bumol, T. F., et al., "Unique Glycoprotein-Proteoglycan Complex Defined by Monoclonal Antibody on Human Melanoma Cells." Proceedings of the National Academy of Sciences of the U.S.A., vol. 79, Feb. 1982, pp. 1245-1249.
Burges, Alexander, et al., "Effective Relief of Malignant Ascites in Patients with Advanced Ovarian Cancer by a Trifunctional Anti-EpCAM x Anti-CD3 Antibody: A Phase I/II Study." Clinical Cancer Research, Jul. 1, 2007, vol. 13, No. 13, pp. 3899-3905.
Center for Drug Evaluation and Research, Application No. 12555700g1s000, Labeling, Amgen Inc., 2014, 28 pages.
Center for Drug Evaluation and Research, Application No. 12555700g1s000, Medical Review(s), Amgen, Inc. dated Sep. 19, 2014, 104 pages.
Clinical Trials.gov, CASIMAS: Catumaxomab Safety Phase IIIb Study With Intrperitoneal Infusion in Patients With Malignant Ascites Due to Epithelial Cancers (CASIMAS). First posted Jan. 14, 2009. <https://clinicaltrials.gov/ct2/show/NCT00822809>, 6 pages.
Dechant, Michael, et al., "Monoclonal antibodies for the treatment of cancer: Reality and future directions." Enhancer—Biotherapy of Cancer, 2005, vol. 3, No. 2, pp. 2-7, 3 pages.
Declaration of Deutsche Nationalbibliothek (Hans-Peter Krieger), dated Sep. 29, 2017, 3 pages.
Declaration of Dr. Malte Koellner, dated Mar. 3, 2017, 2 pages, cited in European U.S. Pat. No. 1874821 B1.
E-Mail from Jutta Schmid, dated Jan. 24, 2017, cited in European Patent No. 1874821 B1, 4 pages (English translation enclosed).
E-Mail from Markus Goertz, dated Jan. 26, 2017, cited in European Patent No. 1874821 B1, 3 pages (English translation enclosed).
E-Mail from Wera Erhard, dated Jan. 24, 2017, cited in European Patent No. 1874821 B1, 2 pages (English translation enclosed).
Email from Markus Gortz regarding publication date for "Sebastian, Martin. Immunologische Aktivierungsparameter bei Patienten mit nicht-kleinzelligem Lungenkarzinom unter Therapie mit dem bispezifishchen Antikorper Removab." reference, email dated Jan. 13, 2017, 2 pages, cited in European Patent. No. 1874821 B1.
European Patent No. 1874821 B1, Fourth Letter regarding the opposition procedure (no time limit), dated Jan. 16, 2017, 10 pages. (English translation enclosed).
European Patent No. 1874821 B1, Letter regarding the opposition procedure (no time limit), dated Jan. 16, 2017, 2 pages.
European Patent No. 1874821 B1, Scanned annex to a communication—opposition procedure, dated Apr. 20, 2017, 16 pages.
European Patent No. 1874821 B1, Second Letter regarding the opposition procedure (no time limit), dated Jan. 16, 2017, 14 pages.
European Patent No. 1874821 B1, Third Letter regarding the opposition procedure (no time limit), dated Jan. 16, 2017, 9 pages. (English translation enclosed).
European Patent No. 1874821 B1, (PCT/EP2005/004468), Supplementary Experimental Results, dated Sep. 10, 2012, 10 pages.
European Patent No. 1874821 B1, Annex to the communication—opposition, dated Apr. 20, 2017, 12 pages (English translation enclosed).
European Patent No. 1874821 B1, Annex to the communication—opposition, dated Jun. 29, 2016, 16 pages (English translation enclosed).
European Patent No. 1874821 B1, Annex to the communication—opposition, List of References, dated Jun. 30, 2017, 35 pages (English translation enclosed).
European Patent No. 1874821 B1, Any annexes (other than citation) to an opposition letter, filed Mar. 7, 2017, dated Aug. 21, 2014, 4 pages.
European Patent No. 1874821 B1, Declaration of Dr. Raymund Buhmann, dated Oct. 31, 2017, 4 pages.
European Patent No. 1874821 B1, First Annex to the communication—opposition, dated May 19, 2017, 35 pages (English translation enclosed).
European Patent No. 1874821 B1, First Letter regarding the opposition procedure (no time limit), dated Oct. 6, 2017, 21 pages.
European Patent No. 1874821 B1, Fourth Letter regarding the opposition procedure (no time limit), dated Oct. 6, 2017, 13 pages (English translation enclosed).
European Patent No. 1874821 B1, Letter accompanying subsequently filed items (Amgen Reasearch (Munich) GmbH AMG149540P, dated Oct. 6, 2017, 2 pages.
European Patent No. 1874821 B1, Letter accompanying subsequently filed items, Strawman Limited, dated Oct. 6, 2017, 2 pages.
European Patent No. 1874821 B1, Letter from Prof. Dr. med. Markus M. Heiss, dated Mar. 15, 2017, 1 page (English translation enclosed).
European Patent No. 1874821 B1, Letter regarding the opposition procedure (no time limit), dated Feb. 16, 2017, 36 pages (English translation enclosed).

(56) References Cited

OTHER PUBLICATIONS

European Patent No. 1874821 B1, Letter regarding the opposition procedure (no time limit), dated Mar. 9, 2017, 14 pages (English translation enclosed).
European Patent No. 1874821 B1, Letter regarding the opposition preocedure, dated Jan. 4, 2018, 3 pages.
European Patent No. 1874821 B1, Letter regarding the opposition procedure, dated Nov. 7, 2017, 35 pages (English translation enclosed).
European Patent No. 1874821 B1, Second Annexes (other than citation) to an opposition letter, dated Mar. 15, 2017, 7 pages.
European Patent No. 1874821 B1, Second Letter regarding the opposition procedure (no time limit), dated Oct. 6, 2017, 21 pages (English translation enclosed).
European Patent No. 1874821 B1, Third Letter regarding the opposition procedure (no time limit), dated Oct. 6, 2017, 7 pages (English translation enclosed).
FDA Drug Approval Package, Blincyto (blinatumomab) Injection, Company: Amgen, Inc., date created: Jan. 12, 2015, http://www.accessdata.fda.gov/drugsatfda_docs/nda/2014/125557origls000TOC.cfm>, retrieved Jan. 13, 2017, 2 pages, cited in European Patent No. 1874821 B1.
Frankfurt, Olga, et al., "Mechanisms of Glucocorticoid-Induced Apoptosis in Hematologic Malignancies: updates." Current Opinion Oncology, 2004, vol. 16, pp. 553-563.
French, Ruth R., et al., "Treatment of B-cell lymphomas with combination of bispecific antibodies and saporin." Lancet, 1995, vol. 346, No. 8969, pp. 223-224, Abstract only.
Haense, N., et al., "A Phase I Trial of the Trifunctional Anti HER2 x anti CD3 Antibody Ertumaxomab in Patients with Advanced Solid Tumors." BMC Cancer, 2016, vol. 16, No. 420, 10 pages.
Harvey, M.L., et al., "Antibodies in the treatment of lymphoma Clinical Oncology." 2001, vol. 13, No. 4, pp. 251-261, Abstract only.
Haynes, Robert C., Jr., "Adrenocorticotropic Hormone: Adrenocortical Steroids and Their Synthetic Analogs: Inhibitors of the Synthesis and Actions of Adrenocortical Hormones." The Pharmacological Basis of Therapeutics, Eighth Edition, 1999, Pergamn Press, Inc., pp. 1431-1462.
Heiss, Markus M., et al., "Immunotherapy of Malignant Ascites With Trifunctional Antibodies." International Journal of Cancer, 2005, vol. 117, pp. 435-443.
Hida, T., et al., "Epitope Analysis of Cluster 1 and NK Cell-Related Monoclonal Antibodies." British Journal of Cancer, 1991, vol. 63, Suppl. XIV, pp. 24-28.
Hinrichs, Christian S., et al., "Glucocorticoids Do Not Inhibit Antitumor Activity of Activated CD8+ T Cells." Journal of Immunotherapy, 2005, vol. 28, No. 6, pp. 517-524.
ICH Efficacy Guidelines, "E6 Good Clinical Practice." Adoption date of Mar. 1997, <http://www.ich.org/products/guidelines/efficacy/article/efficacy-guidelines.html>, retrieved Jan. 11, 2017, 2 pages.
Inaba, Hiroto, et al., "Glucocorticoid Use in Acute Lymphoblastic Leukemia: Comparison of Prednisone and Dexamethasone." Lancet Oncology, Nov. 2010, vol. 11, No. 11, pp. 1096-1106.
International Conference on Harmonisation of Technical Requirements for Registration of Pharmaceuticals for Human Use. ICH Harmonised Tripartite Guideline, Guideline For Good Clinical Practice E6(R1), Current step 4 version, dated Jun. 10, 1996, 59 pages.
Janeway CA Jr, Travers P, Walport M, et al., "T cell-mediated cytotoxicity." Immunobiology: The Immune System in Health and Disease. 5th Edition, New York, Garland Science, 2001. <http://www.ncbi.nlm.nih.gov/books/NBK27101/>, 12 pages.
Janeway, Charles, et al., "CD28-dependent co-stimulation of activated T cells induces expression of the T-cell growth factor interleukin-2 and the high-affinity IL-2 receptor." Janeway's Immunobiology, 7th ed. (2008), Garland Science, Taylor & Francis Group LLC, New York: S.345.
Lester, Robert S. et al., "The Risks of Systemic Corticosteroid Use." Dermatologic Therapy, Apr. 1998, vol. 16, No. 2, pp. 277-286.

Lindhofer, Horst, et al., "Bispecific Antibodies Target Operationally Tumor-Specific Antigens in Two Leukemia Relapse Models." Blood, vol. 88, No. 12, Dec. 15, 1996, pp. 4651-4658.
Loffler, A, et al., "Efficient elimination of chronic lymphocytic leukaemia B cells by autologous T cells with a bispecific anti-CD19/anti-CD3 single-chain antibody construct." Leukemia, May 1, 2003, vol. 17, No. 5, pp. 900-909, Abstract only.
Manzke, Oliver, et al., "CD3 x CD19 bispecific antibodies and CD28 costimulation for locoregional treatment of low-malignancy non-Hodgkin's lymphoma." Cancer Immunology Immunotherapy, 1997, vol. 45, Nos. 3-4, pp. 198-202, Abstract only.
Mau-Sorensen, Morten, et al., "A Phase I Trial of Intravenous Catumaxomab: A Bispecific Monoclonal Antibody Targeting EpCAM and the T Cell Coreceptor CD3." Cancer Chemother Parmacol, 2015, vol. 75, pp. 1065-1173.
Paape, Max J., et al., "The bovine neutrophil: Structure and function in blood and milk." Veterinary Research, Sep./Oct. 2003, vol. 34, No. 5, pp. 597-627, Abstract only.
Park, John W., et al. "Monoclonal antibody therapy." Advances in Protein Chemistry, 2001, vol. 56, pp. 369-421, Abstract only.
Patienteninformation, Klinische Pilotstudie, Immuntherapie solider Tumoren mittels trifunktioneller bispezifischer Antikoper der Spezifitaten anti-EpCAM x anti-CD3 und anti-HER2/neu x anti-CD3. Priv. Doz. Dr. med. M.M. Heisse, Klinikurn der Universitat Munchen, 7 pages, cited in European Patent No. 1874821 B1, filed Mar. 15, 2017 (English translation enclosed).
Rosta, A., et al., "[Current therapy of Hodgkin's disease]. A Hodgkin-kor kezelese." Lege Artis Medicinae, 2001, vol. 11, Nos. 6-7, pp. 412-417, Abstract only.
Roussidis, Andreas E. et al., "Inhibition of receptor tyrosine kinase-based signal transduction as specific target for cancer treatment." In Vivo, Nov./Dec. 2002, vol. 16, No. 6, pp. 459-469, Abstract only.
Ruf, Peter, et al., "Pharmacokinetics, Immunogenicity and Bioactivity of the Therapeutic Antibody Catumaxomab Intraperitoneally Administered to Cancer Patients." British Journal of Clinical Pharmacology, 2010, vol. 69, No. 6, pp. 617-625.
Ruf, Peter, et al., "Two New Trifunctional Antibodies for the Therapy of Human Malignant Melanoma." International Journal of Cancer, 2004, vol. 108, pp. 725-732.
Sehouli, Jalid, et al., "Catumaxomab With and Without Prednisolone Premedication for the Treatment of Malignant Ascites Due to Epithelial Cancer: Results of the Randomised Phase IIIb CASIMAS Study." Medical Oncology, 2014, vol. 31, No. 76, 10 pages.
Stroehlein, Michael , et al., "Induction of Anti-Tumor Immunity by Trifunctional Antibodies in Patients With Peritoneal Carcinomatosis." Journal of Experimental & Clinical Cancer Research, 2009, vol. 28, No. 18, 10 pages.
Tesch, Hans, et al., "[Pathogenesis and treatment of Hodgkin's disease]. Pathogenese Und Therapie Des Hodgkin-Lymphoms." Medizinische Klinik, Feb. 15, 1998, vol. 93, No. 2, pp. 82-90, Abstract only.
Thrush, Gerald R., et al., "Immunotoxins: An Update." Annual Review of Immunology, vol. 14:49-71 (vol. publication date Apr. 1996), Abstract only.
Travaux Preparatoires, Ubereinkommen, Uber Die Erteilung Europaischer Patente (Europaisches Patentubereinkommen), Apr. 2006, 18 pages, cited in European Patent No. 1874821 B1.
Valerius, Thomas, et al., "Involvement of the high-affinity receptor for IgG (Fc gamma RI; CD64) in enhanced tumor cell cytotoxicity of neutrophils during granulocyte colony-stimulating factor therapy." Blood, vol. 82, No. 3, Aug. 1, 1993, pp. 931-939.
Viardot, Andreas, et al., "Blinatumomab Monotherapy Shows Efficacy in Patients with Relapsed Diffuse Large B Cell Lymphoma." Blood, vol. 118, 2011, Abstract, p. 1637.
Voet & Voet, "Biochemistry, Third Edition 2004" John Wiley & Sons, Inc., 2004, pp. 659 and 666.
Walz, Annette (2002): Antitumorale Wirkungsmechanismen eines bispezifischen Antikorpers in vitro gegenuber Einzelzellen and dreidimensionalen Spharoiden. Dissertation, LMU Munchen: Medizinische, Abstract, 3 pages. (English translation enclosed).
Warren, Amy J., et al., "Detection of Mitomycin C-DNA Adducts in Human Breast Cancer Cells Grown in Culture, as Xenografted Tumors in Nude Mice, and in Biopsies of Human Breast Cancer

(56) References Cited

OTHER PUBLICATIONS

Patient Tumors as Determined by 32P-Postlabeling." Clinical Cancer Research, Apr. 2001, vol. 7, pp. 1033-1042.
Wikipedia C-reaktives Protein, obtained Nov. 6, 2017, 2 pages, cited in European Patent No. 1874821 B1.
Zeidler, Reinhard, et al., "TNF-alpha Contributes to the Antitumor Activity of a Bispecific, Trifunctional Antibody." Anticancer Research, vol. 21, 2011, pp. 3499-3504.
European U.S. Pat. No. 1874821 B1, Annex to the Communication—Opposition, dated Mar. 9, 2018, 85 pages (English translation enclosed).
Partial English Machine Translation of pp. 1-55 of Dissertation by Annette Walz, 2002 (cited on Information Disclosure Statement Form as NPL 107), 55 pages.
Partial English Translation of section 4.2.3.3., pp. 45-47, of Dissertation by Annette Walz, 2002 (cited on Information Disclosure Statement Form as NPL 107), 2 pages.
U.S. Appl. No. 60/653,587, Exhibit 12, filed Feb. 15, 2005.
U.S. Label for Alemtuzumab, Apr. 2004 Exhibit 11.
Bao et al., Heparin—binding growth factor, pleiotrophin, mediates neuritogenic activity of embryonic pig brain-derived chondroitin sulfate/dermatan sulfate hybrid chains, The Journal of Biological Chemistry, vol. 280, No. 10, 2006, pp. 9180-9191 Exhibit 6.
Fukuda et al., Outcomes of graft failure/rejection following allogenetic hematopoletic cell transplantation: 10-year experience at FHCRC, Blood, vol. 102, No. 11, p. 240a, XP008057118 Exhibit 7, 2003.
Sakuma et al., Effects of FK506 and other immunosuppressive anti-rheumatic agents on T cell activation mediated IL-6 and IgM production in vitro, International Immunopharmacology, 2001, vol. 1, No. 4, pp. 749-757 Exhibit 8.
Carter, Paul, et al., "Identification and Validation of Cell Surface Antigens for Antibody Targeting in Oncology." Endocrine-Related Cancer, 2004, vol. 11, pp. 659-687.
Janeway, Charles, et al., "Immunolgie." 2002, Spektrum Akademischer Verlag GmbH, Heidelberg, Berlin, pp. 346-348 and 357, cited in European Patent No. 1874821 B1.
Meredith, Ruby F., et al., "Intraperitoneal Radioimmunochemotherapy of Ovarian Cancer: A Phase I Study." Cancer Biotherapy & Radiopharmaceuticals, 2001, vol. 16, No. 4, pp. 305-315.
Patent holder reply to the Statement of Opposition and the Substantiation of Opposition, dated Feb. 9, 2016, 81 pages.
Seidman, Andrew D. et al., "Weekly Trastuzumab and Paclitaxel Therapy for Metastatic Breast Cancer With Analysis of Efficacy by HER2 Immunophenotype and Gene Amplification." Journal of Clinical Oncology, May 15, 2001, vol. 19, No. 10, pp. 2587-2595.
Non-Final Office Action, U.S. Appl. No. 15/934,403, dated Jun. 1, 2018, 15 pages.

\* cited by examiner

Mean values, 3 healthy test subject

| PBMC | 211.3 |
| PBMC+AK | 1273.8 |
| PBMC+AK+HCT8 | 1160.0 |
| PBMC+AK+0.01 | 1100.0 |
| PBMC+AK+0.01+HCT8 | 1027.5 |
| PBMC+AK+0.1 | 931.9 |
| PBMC+AK+0.1+HCT8 | 656.3 |
| PBMC+AK+1 | 528.1 |
| PBMC+AK+1+HCT8 | 443.1 |

| PBMC | 6469.2 |
| PBMC+AK | 13906.7 |
| PBMC+AK+HCT8 | 13990.0 |
| PBMC+AK+0.01 | 11548.3 |
| PBMC+AK+0.01+HCT8 | 13677.5 |
| PBMC+AK+0.1 | 6652.5 |
| PBMC+AK+0.1+HCT8 | 8310.8 |
| PBMC+AK+1 | 1635.8 |
| PBMC+AK+1+HCT8 | 3973.3 |

| | |
|---|---|
| PBMC | 196.3 |
| PBMC+AK | 250.1 |
| PBMC+AK+HCT8 | 762 |
| PBMC+AK+0.01 | 111.3 |
| PBMC+AK+0.01+HCT8 | 684.1 |
| PBMC+AK+0.1 | 170.1 |
| PBMC+AK+0.1+HCT8 | 539.2 |
| PBMC+AK+1 | 117.5 |
| PBMC+AK+1+HCT8 | 394.9 |

| PBMC | 75.4 |
| --- | --- |
| PBMC+AK | 1530.8 |
| PBMC+AK+HCT8 | 1279.1 |
| PBMC+AK+0.01 | 573 |
| PBMC+AK+0.01+HCT8 | 860.3 |
| PBMC+AK+0.1 | 381 |
| PBMC+AK+0.1+HCT8 | 573.6 |
| PBMC+AK+1 | 238.3 |
| PBMC+AK+1+HCT8 | 318 |

| 10x = 500ng/ml | cd3.4.25 | cd3.8.hladr |
| --- | --- | --- |
| PBMC | 26.02 | 16.84 |
| PBMC+AK | 77.24 | 62.65 |
| PBMC+AK+HCT8 | 82.40 | 62.91 |
| PBMC+AK+0.01 | 77.98 | 60.94 |
| PBMC+AK+0.01+HCT8 | 83.93 | 58.90 |
| PBMC+AK+0,1 | 79.37 | 60.09 |
| PBMC+AK+0,1+HCT8 | 82.07 | 57.18 |
| PBMC+AK+1 | 74.89 | 56.93 |
| PBMC+AK+1+HCT8 | 80.65 | 57.13 |

COMBINATION OF THE APPLICATION OF ANTIBODIES FOR IMMUNOSTIMULATION TOGETHER WITH GLUCOCORTICOIDS

This application is a continuation application of U.S. Ser. No. 11/977,856, filed Oct. 26, 2007, now U.S. Pat. No. 8,709,421, issued Apr. 29, 2014, which is a continuation-in-part of (under 35 U.S.C. § 111(a)), and claims the priority to (under 35 U.S.C. §§ 120 and 365(c)), PCT application PCT/EP2005/004468, with international filing date Apr. 26, 2005, the entirety of which is hereby incorporated by reference into this application.

Throughout this application various publications are referenced. The disclosures of these publications in their entirety are hereby incorporated by reference into this application in order to more fully describe the state of the art to which this invention pertains. The invention has been described with reference to various specific and preferred embodiments and techniques. However, it should be understood that many variations and modifications can be made while remaining within the spirit and scope of the invention.

TECHNICAL FIELD

The present invention relates to methods for reducing or eliminating the non-specific release of a cytokine associated with a disease comprising administering at least one glucocorticoid and an immunostimulating antibody. Additionally, the present invention relates to a pharmaceutical composition that contains at least one immunostimulating antibody and at least one glucocorticoid.

BACKGROUND OF THE INVENTION

Immunotherapeutic processes are playing an increasing role in the treatment of diseases, particularly cancer and infections, that hitherto could only be controlled with difficulty or inadequately. In this connection, use is preferably made of antibodies by way of immunostimulating agents; cf. Glennie and Johnson (2000) Immunology Today 21(8): 403-410. The efficacy of immunostimulating antibodies of such a type is based, in particular, on the possibility of the specific binding of defined antigens. However, a great problem in connection with the combating of diseases such as cancer and infections by means of immunostimulating antibodies hitherto has been constituted by the severe side-effects caused by the application of antibodies of such a type, in which connection severe malaise, vomiting, allergic reactions, hypotension, tachycardia, high fever and even fatal circulatory failure or organ failure have been observed in particular, mostly by reason of a SIRS (systemic inflammatory response syndrome).

These intense side-effects of immunostimulating antibodies correlate in most cases with a non-specific release of cytokine, caused by the antibodies, which is responsible for a large proportion of the stated clinical side-effects. The extent of the release of cytokine, which is dependent on the quantity applied and on the velocity of application of the immunostimulating antibody, limits the compatible dose of the respective immunostimulating antibody in clinical use.

Glucocorticoids have long been known as highly effective anti-inflammatory and immunosuppressant active substances. One mechanism in the context of the immunosuppressant action of glucocorticoids is the attenuating action thereof on the transcription of cytokines; cf., for example, Blotta et al. (1997) J. Immunol. 158: 5589 to 5595; Ballow and Nelson (1997) JAMA 278 (22), Chapter 24: 2008 to 2017. In recent years, further advances have been made with regard to the investigation of the immunosuppressant action of glucocorticoids, particularly in connection with the development of T-cells and the function thereof; presented synoptically, for example, in Ashwell and Vacchio (2000) Annu. Rev. Immunol. 18: 309 to 345. In the development of effective immunosuppressant therapies, particularly in connection with the prevention of (acute) transplant rejections, use is preferably made of glucocorticoids in combination with further immunosuppressant agents. For instance, Herbelin et al. (Transplantation (2000) 68 (5): 616 to 622) report an improvement in acute immunosuppression therapy with the anti-CD3 antibody OKT3 with prior administration of glucocorticoids by reason of the reduction, caused by said glucocorticoids, of the production of TNF-α, IL-2 and IFN-γ. However, in the state of the art an administration of glucocorticoids in connection with the stimulation of the immune system of a patient by antibody therapies, for example with trifunctional antibodies (trAB), is totally unknown. In particular, glucocorticoids have been employed hitherto when an immunosuppression was the therapeutic aim.

The object underlying the present invention is therefore to provide a new system for the most extensive possible alleviation of the side-effects of antibodies acting in immunostimulatory manner.

This object is achieved by the embodiments of the present invention that are characterised in the claims.

SUMMARY OF THE INVENTION

The present invention provides methods and pharmaceutical compositions for reducing the non-specific release of a cytokine associated with a disease in a subject.

In an exemplary embodiment, the present invention provides methods for reducing the non-specific release of a cytokine associated with a disease comprising administering at least one glucocorticoid and an immunostimulating antibody.

In further exemplary embodiment, the invention provides pharmaceutical composition containing at least one immunostimulating antibody and at least one glucocorticoid, optionally in conjunction with one or more pharmaceutically compatible carriers and/or adjuvant substances.

The glucocorticoid of the invention can be, but is not limited to, a glucocorticoid such as prednisone, prednisolone, methylprednisolone, triamcinolone, betamethasone, dexamethasone, cortisone acetate, prednylidene, deflazacort, cloprednol, fluocortolone or budenoside, or a combination thereof.

The immunostimulating antibody of the invention can be a monoclonal antibody, a chimeric antibody, humanised antibody, human antibody, trifunctional antibody, multispecific antibody, multifunctional antibody and/or a variant or derivative thereof. The immunostimulating antibody can specifically recognize a tumour antigen and/or a CD marker. Tumor antigens recognized by the immunostimulating antibody include, but is not limited to, EpCAM, HER2/neu, HER3/neu, G250, CEA, MAGE, VEGF, GD3, EGFR, αVβ3-integrin, HLA, HLA-DR, ASC, CD1, CD7, CD11, CD13, CD14, CD19, CD20, CD21, CD22, CD23, CD24, CD33, CD40, CD41, CD52, c-erb-2, CALLA, MHCII, CD44v3, CD44v6, CD117, p97, ganglioside GD2, GD3, C215, antigen of the antibody 9.2.27, antigen of the antibody NE150 and antigen of the antibody CA125. CD markers recognized by the immunostimulating antibody include, but is not limited to, CD2, CD3, CD4, CD5, CD6, CD8, CD28, or CD44.

In a preferred embodiment the immunostimulating antibody is trifunctional with the specificity anti-EpCAM x anti-CD3 or anti-HER2/neu x anti-CD3.

The disease so treated by the methods and/or pharmaceutical compositions of the invention can be a cancerous disease. For example, the cancer can include, but is not limited to, gastric carcinoma, adenocarcinoma, malignant melanoma, colonic carcinoma, pancreatic carcinoma, ovarian carcinoma, uterine carcinoma, hepatocellular carcinoma, all histological types of bronchial carcinoma, lymphomas, sarcomas, blastomas and gastrointestinal stromal tumour (GIST).

Administration of the glucocorticoid(s) and immunostimulating antibody can be done intraperitoneally, intravenously, intra-arterially, intramuscularly, intradermally, subcutaneously, intratumourally or selectively into a defined organ. For example, selective administration into a defined organ can be undertaken via a catheter into a supplying vessel such as the A. hepatica for the liver. Administration of the glucocorticoid(s) and immunostimulating antibody can be done simultaneously or not.

DETAILED DESCRIPTION OF THE INVENTION

In particular, in accordance with the invention the use of one or more glucocorticoids is provided for producing a medicament for reducing the non-specific release of cytokine in the treatment of diseases with one or more immunostimulating antibodies.

This novel indication of glucocorticoids in connection with antibody therapy for immunostimulation in the case of diseases, particularly cancer, is based on the surprising finding that the combination of immunostimulating antibodies of defined specificity together with glucocorticoids results in a reduction of the non-specific release of cytokine by immunological cells without the action of the immunostimulating antibodies directed against the defined antigen(s) being impaired. In particular in connection with the use of antibodies for immunostimulation (for example, against tumour cells), the combination of the antibodies with glucocorticoids results in a modulation of the resulting immune activity; the immune activity of the antibody or antibodies, directed against the defined antigen(s), remains largely unchanged, whereas non-specific effects, such as the non-specific release of cytokine described above, which arise in the application of immunostimulating antibodies independently of the binding to the target antigen(s), are significantly reduced.

By reason of the combination of glucocorticoids (i.e. one or more) with one or more immunostimulating antibodies, in comparison with the immunostimulatory therapies known in the art several advantages arise which considerably extend the possibilities, particularly of clinical applicability, of antibodies for the immunotherapy:

1. By virtue of reducing of the release of cytokine, with the same dosage and largely unchanged specific action (i.e. directed against the target antigen(s)) significantly slighter undesirable side-effects (as listed above) arise.
2. By virtue of reducing of the undesirable side-effects, the dosage of the antibody or antibodies to be applied can be increased considerably. As a result, in combination with glucocorticoids a considerable enhancement of action is possible via the increase in the antibody dose.
3. Surprisingly, the glucocorticoids to be employed in accordance with the invention only reduce the non-specific (systemic) release of cytokine, which is independent of the binding of the target antigen. The release of cytokines therefore arises only at the site of antigen binding (for example, at the site of the binding and intentional destruction of tumour cells). Therefore the action of the immunostimulating antibodies by reason of this effect, in addition to the higher dosage which was stated above and which is now possible, is focused onto the site of antigen binding without being influenced by systemically released cytokines.

The term "antibody" in the sense of the present invention includes monoclonal antibodies, chimeric antibodies, humanised antibodies, human antibody, trifunctional antibody, multispecific antibody and/or multifunctional antibody which may all be present in bound or soluble form, as well as fragments or derivatives of the aforementioned antibodies. In addition to the fragments of antibodies according to the invention on their own, antibodies according to the invention may also appear in recombinant form as fusion proteins with other (protein) constituents. Fragments as such or fragments of antibodies according to the invention as constituents of fusion proteins are typically produced by the methods of enzymatic cleavage, of protein synthesis or by the recombinant methods familiar to a person skilled in the art. A particularly preferred antibody of the present invention is a trifunctional antibody (trAB).

Chimeric antibodies according to the invention are molecules that contain various constituents, these being derived from various animal species (e.g. antibodies that exhibit a variable region derived from a murine monoclonal antibody, and a constant region of a human immunoglobulin). Chimeric antibodies are preferably employed in order, on the one hand, to reduce the immunogenicity in the application and, on the other hand, to increase the yields in the production; for example, murine monoclonal antibodies produce higher yields from hybridoma cell lines, but also result in a higher immunogenicity in man, so that human/murine chimeric antibodies are preferably employed. Still more preferred is a monoclonal antibody that combines in itself the hypervariable, complementarity-defining regions (CDR) of a murine monoclonal antibody with the remaining regions of a human antibody. An antibody of such a type is called humanised antibody. Chimeric antibodies and processes for their production are known from the art (Cabilly et al., Proc. Natl. Sci. USA 81: 3273-3277 (1984); Morrison et al. Proc. Natl. Acad. Sci USA 81:6851-6855 (1984); Boulianne et al. Nature 312: 643-646 (1984); Cabilly et al., EP-A-125 023; Neuberger et al., Nature 314: 268-270 (1985); Taniguchi et al., EP-A-171 496; Morrion et al., EP-A-173 494; Neuberger et al., WO 86/01533; Kudo et al., EP-A-184 187; Sahagan et al., J. Immunol. 137: 1066-1074 (1986); Robinson et al., WO 87/02671; Liu et al., Proc. Natl. Acad. Sci USA 84: 3439-3443 (1987); Sun et al., Proc. Natl. Acad. Sci USA 84: 214218 (1987); Better et al., Science 240: 1041-1043 (1988) and Harlow and Lane, Antibodies: A Laboratory Manual, supra. These cited references are incorporated into the present invention as being pertinent to the disclosure.

The expression "immunostimulating antibody" or "immunotherapeutic antibody" in the sense of the present invention means that the respective antibody, by reason of its antigen specificity, brings about or assists a stimulation of the immune system of the patient that is desired within the scope of the treatment of the respective disease.

In particular, immunostimulating antibodies in the sense of the present invention are those which induce a T-cell activation. Particularly advantageous in this connection is an activation of cytotoxic T-cells (CTL, cytotoxic T-lymphocytes, so-called T killer cells). Also encompassed, however, are immunostimulating antibodies with antibody-mediated effects, which occur, for example, via an activation of T helper cells, accessory cells (macrophages), dendritic cells, B-cells or natural killer cells (NK cells).

Particularly preferred immunostimulatory antibodies are multispecific, in particular bispecific, and/or multifunctional, in particular trifunctional. In the case of bispecific antibodies in particular, recombinant antibody molecules are to be mentioned, which are produced by recombinant techniques, for example scFv molecules (so-called single-chain antibodies), diabodies etc. The basic structure of bispecific antibodies and immunoconjugates is presented, for example, in van Spriel et al. (2000) Immunol. Today 21: 391-397. Bispecific antibodies may, of course, also be produced by known hybridoma techniques. Processes for producing multivalent and bispecific antibody fragments are known to a person skilled in the art and are described, for example, in Tomlinson and Holliger (2000) Meth. Enzymol. 326: 461 ff. A particularly preferred example of a bispecific antibody is a trifunctional bispecific antibody, to the Fc portion of which, i.e. the portion of the antibody that is not directly involved in the antigen binding, accessory immune cells are able to bind.

Preferred bispecific immunostimulatory antibodies are, in accordance with the invention, those which exhibit at least one specificity against an antigen on a cell to be killed, for example a tumour cell, and against a CD marker. The CD marker of a bispecific, immunostimulating antibody of such a type is preferably expressed on T-lymphocytes and is therefore selected from the group consisting of CD2, CD3, CD4, CD5, CD6, CD8, CD28 and CD44. The T-cell specificity of the bispecific antibody consequently recruits T-cells, on the one hand, in specific manner. The second specificity of the preferred, immunostimulatory active antibody is directed against an antigen that is expressed as specifically as possible on the cell to be eliminated by the immune system. In the case of cancer cells, this is preferentially a so-called tumour antigen, i.e. a peptide or polypeptide expressed on the surface of the cells of a tumour. Preferred tumour antigens of antibodies that are active in immunostimulatory manner against cancer cells are, for example, EpCAM, HER2/neu, HER3/neu, G250, CEA, MAGE, VEGF, GD3, EGFR, $\alpha V\beta 3$-integrin, HLA, HLA-DR, ASC, CD1, CD2, CD4, CD6, CD7, CD8, CD11, CD13, CD14, CD19, CD20, CD21, CD22, CD23, CD24, CD33, CD40, CD41, CD52, c-erb-2, CALLA (CD10), MHCII, CD44v3, CD44v6, CD117, p97, ganglioside GD2, GD3, C215, antigen of the Ab 9.2.27, antigen of the Ab NE150 and antigen of the Ab CA125 (cf. also Jager (2001) J. Clin. Pathol. 54(9): 669-674; Jager (2002) Curr. Opin. Immunol. 14 (2): 178-182).

Particularly preferred in this context is, as already mentioned, a variant of a bispecific antibody molecule that on the Fc portion exhibits one or more binding sites for accessory immune cells. This antibody type accordingly recruits not only the cell to be eliminated, for example a tumour cell, and T-cells, but at the same time also accessory immune cells such as monocytes or macrophages, and in this way forms a "tri-cell complex". By virtue of the recruitment of the third cellular binding partner, the phagocytosis of the cell to be eliminated is triggered. This, in turn, is the prerequisite for the emergence of a polyclonal immune response, as a result of which the patient is immunised not only against the isolated antigen, expressed on the cell to be eliminated, but against a large number of the cells to be eliminated, in particular tumour cells, in the body of the patient, with all possible mutations.

Particularly preferred embodiments of trifunctionally bispecific antibodies that are active in immunostimulatory manner in accordance with the invention are endowed, for example, with the specificity anti-EpCAM x anti-CD3 or anti-HER2/neu x anti-CD3.

The glucocorticoid to be used in accordance with the invention is not particularly restricted, and may be both naturally occurring, for example hydrocortisone (cortisol) or cortisone, or of synthetic nature. There is also no restriction whatsoever with respect to a selection as regards the biological half-life (active in the short term, active in the medium term and active in the long term). Synthetic glucocorticoids to be used in accordance with the invention are, for example, prednisone, prednisolone, methylprednisolone, triamcinolone, betamethasone, dexamethasone, cortisone acetate, prednylidene, deflazacort, cloprednol, fluocortolone and budenoside, this list being by no means definitive.

A particularly preferred glucocorticoid according to the present invention is the glucocorticoid dexamethasone. This is a synthetic glucocorticoid, the half-life of which amounts to 36 hours to 54 hours; this corresponds to a glucocorticoid that is active in the long term. It is therefore particularly suitable for a treatment with requisite continuous glucocorticoid action. After its administration, dexamethasone is bound to albumin in a proportion amounting to 70% to 80%, so that a free and active proportion of the glucocorticoid of 20% to 30% is present. Dexamethasone has an action that is approximately 30 times stronger than that of the natural adrenocortical hormone cortisone, a slight mineralocorticoid action, and a slight water-retaining and salt-retaining action. Amongst many other applications, it is also particularly suitable for application in patients with cardiac insufficiency or hypertension. Of significance therapeutically is, moreover, the strong antiphlogistic and immunosuppressive (antiallergic) action of dexamethasone. Also advantageous is the fact that maximum plasma concentrations are attained within a few minutes after i.v. injection.

By way of examples of cancerous diseases that are capable of being treated with the immunotherapeutic antibody (or even several antibodies) according to the invention in conjunction with the glucocorticoid (or several glucocorticoids), gastric carcinoma, adenocarcinoma, malignant melanoma, colonic carcinoma, pancreatic carcinoma, ovarian carcinoma, uterine carcinoma, hepatocellular carcinoma, bronchial carcinoma (all histological types), lymphomas, sarcomas, parvicellular pulmonary carcinoma, blastomas, gastrointestinal stromal tumour (GIST) etc. may be mentioned.

As regards to the manner of administration both of the immunostimulatory antibody and of the glucocorticoid, in accordance with the invention there are no restrictions whatsoever. Therefore both the glucocorticoid and the antibody can be administered intraperitoneally, systemically (intravenously or intra-arterially), intramuscularly, intradermally, subcutaneously, intratumourally, but also selectively into or via a defined organ. Of course, the glucocorticoid may, in particular, also be applied orally or—in the form of an ointment, a gel or another suitable form of administration—even onto the skin. As an example of a selective application into or via an organ, the administration via the bone marrow (as immunological organ) or via a superselective catheter into a vessel (artery) supplying the respective organ may be mentioned. As a specific example of an application of such a type by means of catheter, that into the A. hepatica for selective application into the liver or for systemic administration after passing through the organ may be specified. Further examples of organ-specific application are those into the liver via the portal vein, into the kidney via the renal artery, intrathecal application in the case of cerebral tumours, into the colonic region via mesenteric vessels, into the pancreas via the truncus coeliacus and the A. mesenteria superior, and into tumours in limbs via the corresponding arteries. Furthermore, direct application into a tumour may also be effected. Of course, in the case of the use, according to the invention, of immunostimulating antibodies and glucocorticoid the application of these active components may be effected by like methods or by different methods; for example, the antibody or antibodies selectively via the liver, the glucocorticoid(s) systemically, for example intravenously.

The glucocorticoid may, for example, be administered to the antibody acting by way of immunostimulatory agent simultaneously, separately or in temporally staggered manner. The glucocorticoid may accordingly be administered to the antibody temporally before or after or simultaneously. According to a particularly preferred embodiment, the glucocorticoid and the immunostimulatory antibody are administered approximately simultaneously.

A further subject of the invention is a product containing at least one immunostimulatory or immunotherapeutic antibody as defined above and at least one glucocorticoid according to the above definition in the form of a combined preparation for simultaneous, separate or temporally staggered application in connection with the treatment and/or prophylaxis of cancerous diseases, tumorous diseases. Cancerous diseases include, for example, gastric carcinoma, adenocarcinoma, malignant melanoma, colonic carcinoma, pancreatic carcinoma, ovarian carcinoma, uterine carcinoma, hepatocellular carcinoma, all histological types of bronchial carcinoma, lymphomas, sarcomas and/or blastomas.

The constituents of the product according to the invention—at least one immunostimulatory or immunotherapeutic antibody as defined above (1st constituent) and at least one glucocorticoid according to the above definition (2nd constituent)—are functionally unified by virtue of their targeted use. The constituents of the product may not develop the advantageous action, described above, according to the invention independently of one another, so that despite the spatial separation of constituents 1 and 2 (for simultaneous, separate or temporally staggered administration) their application is available in the form of a new combined product which is not described in the state of the art.

A product according to the invention may include all the constituents, substances and embodiments such as are employed in a process or therapeutic process or process for the treatment and/or prophylaxis of diseases or in a combined-therapy process according to the present invention.

A further subject of the invention relates to a pharmaceutical composition containing at least one immunostimulatory or immunotherapeutic antibody as defined above and at least one glucocorticoid according to the above definition. The pharmaceutical composition of the present invention is suitable, in particular, for treating the diseases listed above. The pharmacologically active constituents of the pharmaceutical composition according to the invention are optionally present in conjunction with one or more carriers and/or adjuvant substances, as stated more precisely below.

In the pharmaceutical composition according to the invention, or in the case of the use according to the invention of the glucocorticoids, the latter and the antibody are advantageously made available in suitable formulations. Formulations of such a type are known to a person skilled in the art and contain, in addition to the substances acting in therapeutic or immunostimulatory manner, one or more pharmaceutically compatible carriers and/or pharmaceutically compatible excipients. Appropriate methods for suitable formulation and production of formulations of such a type are disclosed, for example, in "Remington's Pharmaceutical Sciences" (Mack Pub. Co., Easton, Pa., 1980), the full content of which is an integral part of the disclosure of the present invention. For parenteral administration, sterile water, sterile saline solution, polyalkylene glycols, hydrated naphthalenes and, in particular, biocompatible lactide polymers, lactide/glycolide copolymers or polyoxyethylene/polyoxypropylene copolymers, for example, enter into consideration as carrier substances. Pharmaceutical compositions according to the invention may contain filling substances or substances such as lactose, mannitol, substances for covalent linkage of polymers—such as polyethylene glycol, for example—to immunostimulatory antibodies according to the invention, for complexing with metal ions or inclusion of materials into or onto particular preparations of polymer compounds, such as, for example, polylactate, polyglycolic acid, hydrogel, or on liposomes, microemulsions, micelles, unilamellar or multilamellar vesicles, erythrocyte fragments or spheroblasts. The respective embodiments of the pharmaceutical compositions are chosen in a manner depending on the physical behaviour, for example with regard to solubility, stability, bioavailability or degradability. Controlled or constant release of the active-substance components according to the invention includes the formulation on the basis of lipophilic deposits (e.g. fatty acids, waxes or oils). Within the scope of the present invention, coatings of pharmaceutical compositions or medicaments according to the invention, containing the therapeutically active substances, namely coatings with polymers, are also disclosed (e.g. polyoxamers or polyoxamines). Moreover, therapeutically active substances or compositions according to the invention may exhibit protective coatings, for example protease-inhibitors or permeability-intensifiers. Preferred carriers are, typically, aqueous carrier materials, in which case use is made of water for injection (WFI) or water, buffered with phosphate, citrate, HEPES or acetate etc., and the pH is typically adjusted to 5.0 to 8.0 (preferentially 6.5 to 7.5). The carrier or the excipient will additionally preferentially contain salt constituents, for example sodium chloride, potassium chloride, or other components that make the solution isotonic, for example. Moreover, the carrier or the excipient may contain, in addition to the aforementioned constituents, additional components such as human serum albumin (HSA), polysorbate 80, sugar or amino acids etc.

The manner of administration and dosing of the medicament according to the invention or of the product according to the invention or of the pharmaceutical composition depend on the type of disease to be combated, where appropriate the stage thereof, the antigen to be controlled, and also the body weight, the age and the sex of the patient.

The concentration of the active components in the formulations according to the invention may be varied within a wide range. Doses, according to the invention, of the antibody fluctuate within the range from about 1 µg to about 1 mg, whereas glucocorticoids are generally administered in doses from about 1 mg to about 1000 mg, in particular about 1 mg to about 100 mg.

For example, the antibody can be administered in a dose between 1 µg to 10 µg, 10 µg to 20 µg, 20 µg to 30 µg, 30 µg to 40 µg, 40 µg to 50 µg, 50 µg to 60 µg, 60 µg to 70 µg, 70 µg to 80 µg, 80 µg to 90 µg, 90 µg to 100 µg, 1 µg to 50 µg, 50 µg to 100 µg, 100 µg to 150 µg, 150 µg to 200 µg, 200 µg to 250 µg, 250 µg to 300 µg, 300 µg to 350 µg, 350 µg to 400 µg, 400 µg to 450 µg, 450 µg to 500 µg, 500 µg to 550 µg, 550 µg to 600 µg, 600 µg to 650 µg, 650 µg to 700 µg, 700 µg to 750 µg, 750 µg to 800 µg, 800 µg to 850 µg, 850 µg to 900 µg, 900 µg to 950 µg, 950 µg to 1 mg.

For example, a glucocorticoid can be administered in a dose between 1 mg to 10 mg, 10 mg to 20 mg, 20 mg to 30 mg, 30 mg to 40 mg, 40 mg to 50 mg, 50 mg to 60 mg, 60 mg to 70 mg, 70 mg to 80 mg, 80 mg to 90 mg, 90 mg to 100 mg, 1 mg to 50 mg, 50 mg to 100 mg, 100 mg to 150 mg, 150 mg to 200 mg, 200 mg to 250 mg, 250 mg to 300 mg, 300 mg to 350 mg, 350 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1000 mg.

In accordance with the invention, a process for treating the aforementioned diseases is furthermore made available that includes the administering to a patient, in particular to a human being, of an immunostimulating antibody according to the above definition and at least one glucocorticoid. In this connection the previous or simultaneous application of the glucocorticoid before or together with the immunostimulating antibody is preferred. Of course, in accordance with the invention several immunostimulating antibodies and several glucocorticoids may be used in any combination.

A further subject of the invention relates to a kit that contains at least one immunostimulatory or immunotherapeutic antibody as defined above and at least one glucocorticoid according to the above definition, the at least one immunostimulatory or immunotherapeutic antibody as defined above and the at least one glucocorticoid according to the above definition being separated from one another.

A preferred embodiment of the invention relates to the use of the kit for the treatment and/or prophylaxis of cancerous diseases, tumour diseases. Cancerous diseases include, for example, gastric carcinoma, adenocarcinoma, malignant melanoma, colonic carcinoma, pancreatic carcinoma, ovarian carcinoma, uterine carcinoma, hepatocellular carcinoma, all histological types of bronchial carcinoma, lymphomas, sarcomas and/or blastomas.

BRIEF DESCRIPTION OF THE FIGURES

The Figures show:

FIG. 1A represents the release of IL-6, the IL-6 concentration in pg/ml being plotted on the y-axis. On the x-axis the respective stimulation of the PBMC has been plotted, with unstimulated PBMC serving by way of control (bar "PBMC"). In this connection, E signifies in each instance the stimulation with 100 µg/ml trifunctional bispecific antibody with the specificity anti-EpCAM x anti-CD3. Dexamethasone with the specified concentration in µg/ml is denoted by "Dexa". In the experiment according to FIG. 1A the release of IL-6 from PBMC is investigated after stimulation without contact with EpCAM-positive tumour cells (=target cells). The stimulation without EpCAM-positive tumour cells corresponds to the non-specific release of cytokine, which is independent of the antigen binding. Release is accordingly effected systemically by the totality of the PBMC. As FIG. 1A shows, dexamethasone reduces the release of IL-6 in concentration-dependent manner. In the case of a concentration of 1 µg/ml an almost total suppression of the release of IL-6 occurs. Therefore the side-effects caused by the systemic release of IL-6 should be able to be almost totally suppressed by a sufficiently high dose of dexamethasone.

FIG. 1B shows, in a plotting corresponding to FIG. 1A, the release of IL-6 from PBMC after stimulation with contact with EpCAM-positive tumour cells (HCT8; concentration $5 \times 10^4$ cells/ml). This procedure of stimulation with EpCAM-positive tumour cells corresponds to the situation of the release of IL-6 by the PBMC at the site of antigen binding. The IL-6 measured in this experimental arrangement therefore corresponds to the specific (i.e. targeted) action of the antibody that has been used and consequently does not constitute an undesirable side-effect. IL-6 is only released from immune cells that are directly involved in the specific immune reaction. The absolutely higher release (cf. the graduation of the y-axis in FIG. 1B with that in FIG. 1A) is therefore not to be appraised as a sign of a heightened side-effect, but is explained through the specific immunological action at the site of antigen binding. In the clinical use of the immunostimulating antibody together with the glucocorticoid the high quantity of IL-6 is released only by a few PBMC that are directly involved in the specific action. But the side-effects result from the non-specific release of interleukins by the totality of the PBMC (documented in the above FIG. 1A). As is evident from FIG. 1B, in the case of a dexamethasone concentration of 1 µg/ml the release of IL-6 is indeed reduced but lies far above the systemic release that is observed in the case of a stimulation without EpCAM-positive tumour cells with the antibody without dexamethasone (cf. FIG. 1A). Therefore in the case of a combined administration of the immunostimulating antibody with dexamethasone the non-specific release of IL-6 is substantially suppressed, whereas the targeted action of the immunostimulating antibody is still significant.

FIG. 1C represents in a further diagram a percentage comparison of the release of IL-6 after stimulation without/with HCT8 cells (target cells) in accordance with FIGS. 1A and 1B described above. On the y-axis the percentage release of IL-6 is represented, relative to the value without simultaneous use of dexamethasone (=100%). The respectively left-hand bars represent the values after stimulation without HCT8, whereas the respectively right-hand bar indicates the result after stimulation with HCT8 cells. Between a dexamethasone dosage from 0.1 µg/ml to 1 µg/ml a dissociation of the secretion of IL-6 takes place in the case of stimulation of the PBMC with the antibody in the absence of HCT8 cells in comparison with the stimulation in the presence of HCT8 cells: at 1 µg/ml dexamethasone the specific (i.e. caused by binding of the EpCAM-positive tumour cell) action-associated release of IL-6 is maintained. In contrast thereto, the non-specific secretion of IL-6. which is independent of the antigen binding (in the present case, the EpCAM binding on the HCT8 cells), has been substantially reduced or has disappeared.

FIG. 2A shows, in a manner similar to that in the above FIG. 1A (there with respect to IL-6), the release of TNF-α from PBMC after stimulation without contact with EpCAM-positive tumour cells, the TNF-α concentration in pg/ml being plotted here on the y-axis. This stimulation without target cells corresponds, in turn, as already stated with respect to FIG. 1A, to the systemic, non-specific release of cytokine, which arises independently of the antibody/antigen interaction. This systemic release of TNF-α is effected by the totality of the PBMC population. Dexamethasone reduces the release of TNF-α in concentration-dependent manner. At a concentration of 0.1 µg/ml a great reduction of the release of TNF-α already occurs, which amounts to about one fifth of the release of TNF-α that arises in the case of a stimulation with antibody without administration of glucocorticoid. At a glucocorticoid concentration from 1 µg/ml and higher, a total suppression of the release of TNF-α even occurs.

FIG. 2B represents, in a diagram similar to FIG. 1B, the release of TNF-α from PBMC after antibody stimulation with contact with EpCAM-positive tumour cells, the TNF-α concentration in pg/ml being plotted, here too, on the y-axis. The remainder of the plotting corresponds to that of FIG. 1B. The stimulation with EpCAM-positive tumour cells as target cells, which was carried out in this experimental arrangement, corresponds to the situation of the release of TNF-α by the PBMC at the site of antigen binding. Therefore the TNF-α concentration measured in this experiment is to be ascribed, for the most part, to the specific (targeted) action of the antibody and consequently does not constitute an undesirable side-effect. In the case of stimulation with contact with EpCAM-positive tumour cells, in comparison with the stimulation without contact with target cells, in connection with the release of TNF-α absolutely higher values are also measured, which, however, as already stated above with respect to the release of IL-6 in connection with FIG. 1B, has its origin in the specific immunological action at the site of the antibody/antigen interaction. Also in the case of the release of TNF-α being investigated in the present case, at a concentration of the glucocorticoid dexamethasone of 1 µg/ml and more a distinct reducing of the specific release of TNF-α is observed, which, however, is still significant.

FIG. 2C represents, in a plotting corresponding to FIG. 1C, a percentage comparison of the release of TNF-α after stimulation without (in each instance, left-hand bar) and with (in each instance, right-hand bar) HCT8 target cells. The 100% values correspond to the release of TNF-α without simultaneous administration of dexamethasone. With regard to the application, cf. FIG. 1C. Also with respect to TNF-α, between a dexamethasone dosage of 0.1 µg/ml and 1 µg/ml a dissociation of the cytokine secretion without target cells is observed in comparison with the stimulation with contact with target cells. At 1 µg/ml dexamethasone the specific (by virtue of binding of the EpCAM-positive tumour cell) action-associated release of TNF-α is maintained (more than 60% of the release of cytokine relative to the stimulation by antibodies without simultaneous addition of glucocorticoid). In contrast thereto, the non-specific secretion of TNF-α, which arises independently of the antigen binding (EpCAM binding on HCT8 cells), is reduced when accompanied by addition of 0.1 µg/ml dexamethasone to a good 20% of the value that is measured in the case of stimulation with antibody without addition of dexamethasone. In the case of 1 mg/ml dexamethasone, the non-specific release of TNF-α has even totally disappeared.

FIG. 3A confirms, in a plotting corresponding to FIGS. 1A and 2A (y-axis: IFN-γ concentration in pg/ml), the expectation presented above, since a release of IFN-γ occurs without contact with EpCAM-positive tumour cells (HCT8) in the case of no stimulation.

FIG. 3B documents the release of IFN-γ from PBMC after antibody stimulation with contact with EpCAM-positive tumour cells (HCT8). In the case of stimulation of the PBMC with the bispecific antibody in contact with the target cells (HTC8) a significant release of IFN-γ occurs, which in the case without addition of glucocorticoid amounts to over 6000 µg IFN-γ/ml. In the case of a simultaneous administration of 0.01 µg/ml dexamethasone this release of IFN-γ is even somewhat increased (over 7000 µg/ml). In the case of a dexamethasone concentration of 0.1 µg/ml the release of IFN-γ is indeed reduced to just under 3000 pg/ml, but is still significant.

FIG. 3C represents, in a manner similar to that in FIGS. 1C and 2C, a percentage comparison of the release of cytokine (here IFN-γ) after stimulation by antibody without and with contact with HCT8 target cells.

In FIGS. 4A to 4E there has been plotted in each instance on the y-axis the percentage fraction of the CD3/CD4 (T helper cells) or CD3/CD8 (T killer cells)-positive T-lymphocytes with expression of an activation marker (FIGS. 4A and 4C: CD25; FIGS. 4B and 4D: CD69; FIG. 4E: HLA-DR). The measurement was undertaken by FACS analysis. The respectively left-hand bars represent the results of the stimulation without contact with HCT8 target cells (concentration $5\times10^4$ cells/ml), whereas the respectively right-hand bars indicate the measured values in the case of stimulation with contact with HCT8 target cells. In the case of stimulation with the trifunctional bispecific antibody subject to contact with the HCT8 target cells, which corresponds to the specific stimulation with binding of the target antigen, the T-cell activation is not influenced by dexamethasone, as the unchanged high measured values in FIGS. 4A to 4E substantiate.

In FIGS. 5A to 5D the specific percentage cytotoxicity against HCT8 has been plotted as a function of the ratio of effector cells to target cells (E/T), the cytotoxicity test having been carried out in each instance in the case of a ratio of the effector cells to the target cells of 40:1, 20:1, 10:1, 5:1 and 2.5:1. In each experiment a stimulation with 100 µg/ml trifunctional bispecific antibodies with the specificity anti-EpCAM x anti-CD3 (E) without HCT8 cells was effected in the presence of HCT8 cells (E+HCT8) and also subject to additional administration of dexamethasone in concentrations of 0.01 µg/ml, 0.1 µg/ml, 1.0 µg/ml or 10.0 µg/ml without (E+µg/ml Dexa) and with contact with HCT8 cells (E+µg/ml dexa+HCT8).

FIG. 5A documents the influence of dexamethasone in a concentration of 0.01 mg/ml on the specific percentage cytotoxicity. In comparison with PBMC without dexamethasone, here by virtue of the glucocorticoid no inhibition of the specific percentage cytotoxicity arises.

FIG. 5B represents the results of the corresponding measurements with regard to the influence of 0.1 µg/ml dexamethasone. At this dexamethasone concentration a distinct inhibition of the specific percentage cytotoxicity by about 50 percentage points arises. In this connection no appreciable difference arose if the stimulation was carried out in the presence or in the absence of HCT8 cells.

FIG. 5C shows the results of the comparative measurements with dexamethasone in a concentration of 1 µg/ml. Here too, a distinct inhibition of the specific percentage cytotoxicity arose, which showed roughly the same level as was established in the case of a glucocorticoid concentration of 0.1 µg/ml (cf. FIG. 5B) if the stimulation of the PBMC was effected in the presence of HCT8 cells. In the case of a ratio of the effector cells to target cells of 20:1, in the absence of HCT8 a distinctly greater inhibition of the percentage specific cytotoxicity of the PBMC arose.

FIG. 5D reproduces the corresponding measurements in the case of a dexamethasone concentration of 10 µg/ml. In the case of stimulation of the PBMC in the presence of HCT8 cells, at this dexamethasone concentration a percentage specific cytotoxicity arose that corresponded roughly to that which was established in the case of dexamethasone concentrations of 0.1 µg/ml and 1 µg/ml (cf. FIGS. 5B and 5C): In the case of a ratio of effector cells to target cells of 20:1, a percentage cytotoxicity of 30% accordingly arose, whereas in the case of a ratio of effector cells to target cells that was twice as large the specific percentage cytotoxicity amounted to about 60%. In contrast thereto, in the case of a stimulation of the PBMC in the absence of HCT8 cells the cytotoxicity values in relation to the lower dexamethasone concentrations declined further.

According to the results presented in FIGS. 5A to 5D, dexamethasone has no effect on the cytotoxicity of stimulated PBMC at a concentration of 0.01 µg/ml. Starting from a concentration of 0.1 µg/ml, a distinct reducing of the cytotoxicity arises, independently of the absence or presence of HCT8 during the stimulation. In the case of a stimulation in the presence of HCT8, the percentage specific cytotoxicity remains at a level of 40% to 60% of the cytotoxicity that was measured without dexamethasone if dexamethasone above a concentration range of 3 orders of magnitude (0.1 µg/ml to 10 µg/ml) was given in the case of a ratio of effector cells to target cells of 40:1. Therefore in the case of a corresponding ratio of effector (E) cells to target (T) cells in the case of addition of glucocorticoid within a large concentration range a distinct percentage cytotoxicity of the PBMC stimulated in the presence of HCT8 cells is maintained constant. In contrast thereto, the cytotoxicity declines further in a manner depending on the dexamethasone concentration after stimulation of the PBMC without HCT8.

FIG. 6A-6E documents the laboratory values of immunological parameters of a patient with a chemotherapy-resistant gastric carcinoma which was treated, in accordance with the invention, with a trifunctional, bispecific antibody (anti-EpCAM x anti-CD3) immunostimulation against the tumour cells and also with glucocorticoid (dexamethasone) for the inhibition of the side-effects associated with the immunotherapy. On the y-axis of FIGS. 6A to 6E the measured values are plotted in each instance in the respectively specified unit. The course of the therapy in days is represented on the x-axis. In this connection E signifies an administration of the aforementioned immunostimulatory antibody with the dosage i.p. in µg, and Dex signifies the dexamethasone dose in mg which was administered i.v.

Figure 6A:
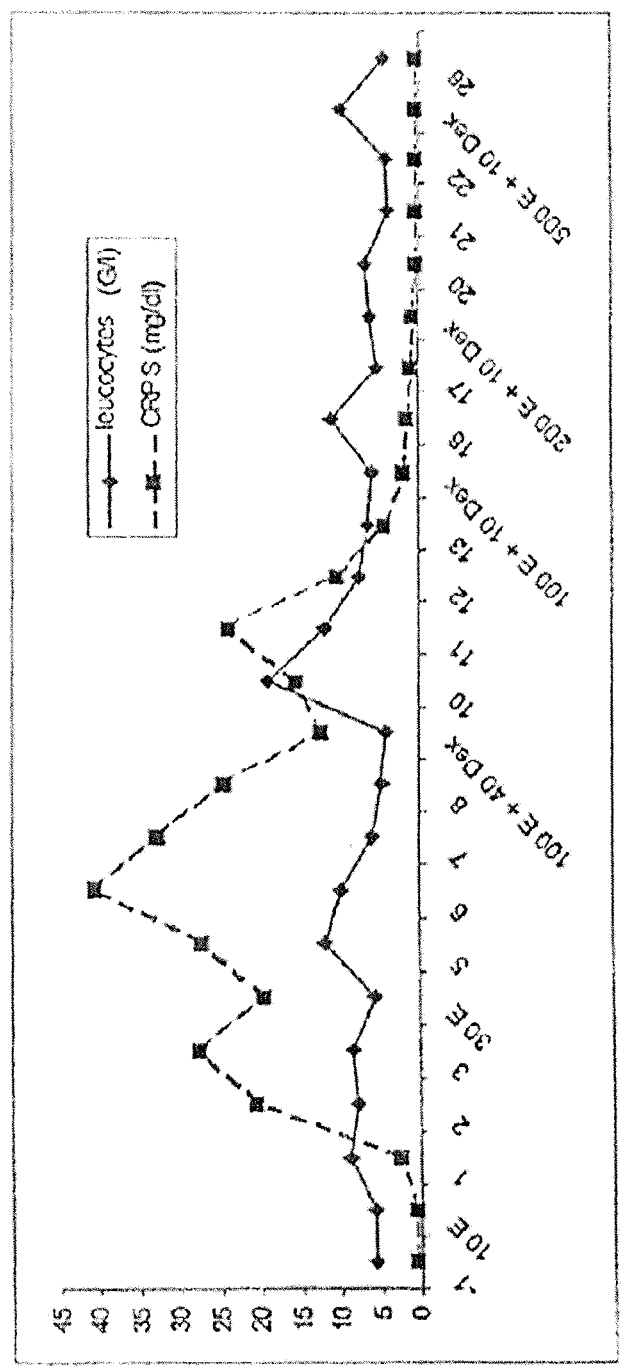

FIG. 6A represents the curve of the leucocyte concentration (in g/l) (♦) and also the serum-CRP concentrations (in mg/dl) (■). The first two doses of antibody on day 0 and on day 4 were effected without additional administration of the glucocorticoid. Under this therapy the serum concentration of the "acute-phase protein" CRP, in particular, rises to 40 mg/dl. In the further course of the therapy with additional application of dexamethasone with, at the same time, a distinct increase in the antibody dosage up to 500 µg the CRP-serum level falls back to normal values. The leucocyte concentration under the combined therapy according to the invention also remains below 20 g/l. Normal values in healthy adults fluctuate between 4 g/l and 11 g/l. The observed increase in the number of leucocytes is also an expression of the desired immunostimulation.

Figure 6B:
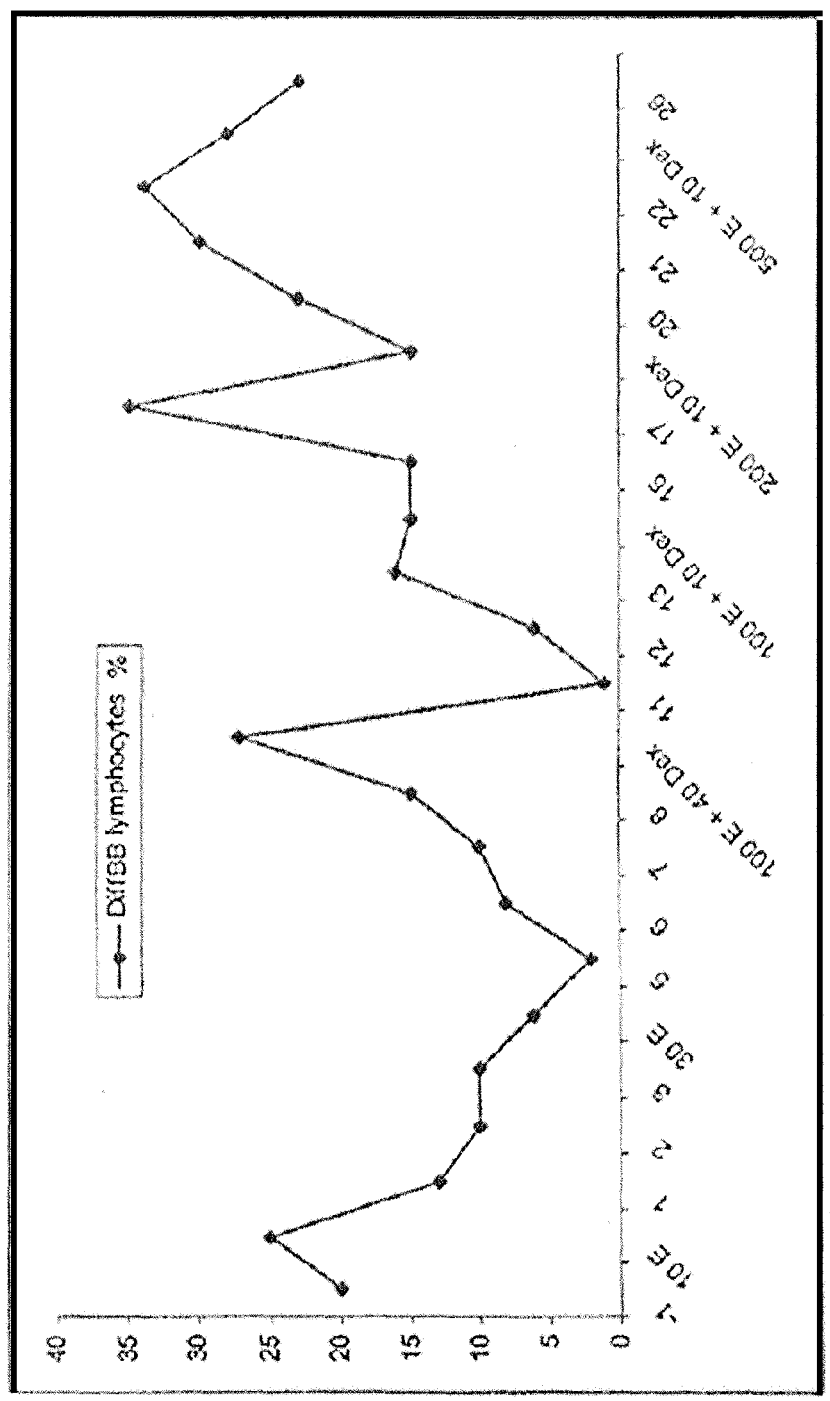

FIG. 6B represents the curve of the percentage fraction of the lymphocytes in the differential blood count. The observed fluctuations both under the antibody monotherapy at the start of the treatment and in the case of additional administration of dexamethasone subject to a simultaneous great increase in the dose of the immunotherapeutic antibody conform to expectations. In particular, towards the end of the administration of the combination, according to the invention, of antibody and glucocorticoid the measured values lie roughly within the normal range of a healthy adult (20% to 30% lymphocytes).

Figure 6C:
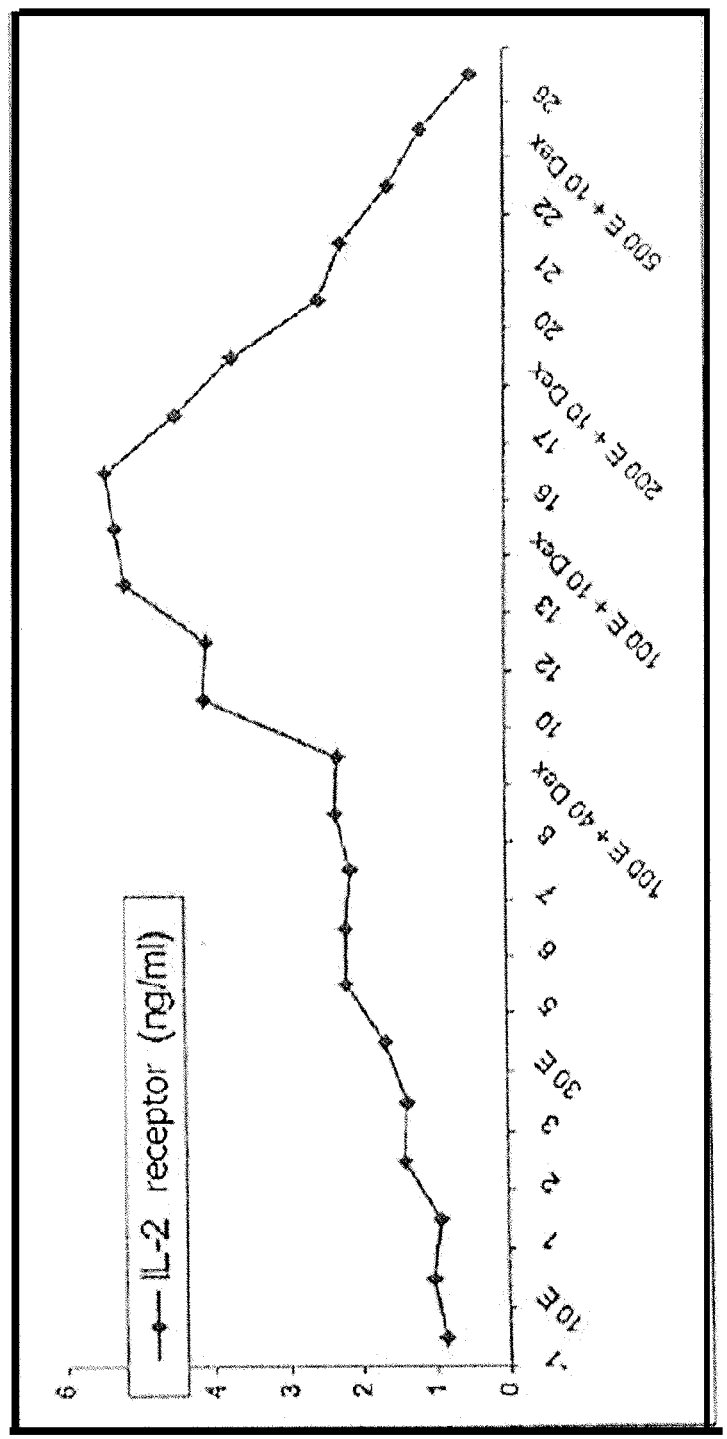

FIG. 6C shows the curve of the serum concentration of the IL-2 receptor. The values rise from about 1 ng/ml to about 2 ng/ml at the start of the treatment, at first in the case of increase of the dose of the immunstimulatory antibody to 100 µg i.p. and additional administration of dexamethasone to about 5.5 ng/ml, but fall again towards the end of the treatment despite a further distinct increase in the dose of the trifunctional, bispecific antibody and simultaneous administration of the glucocorticoid at a dose of 10 mg i.v., to below 1 ng IL-2 receptor/ml.

Figure 6D:
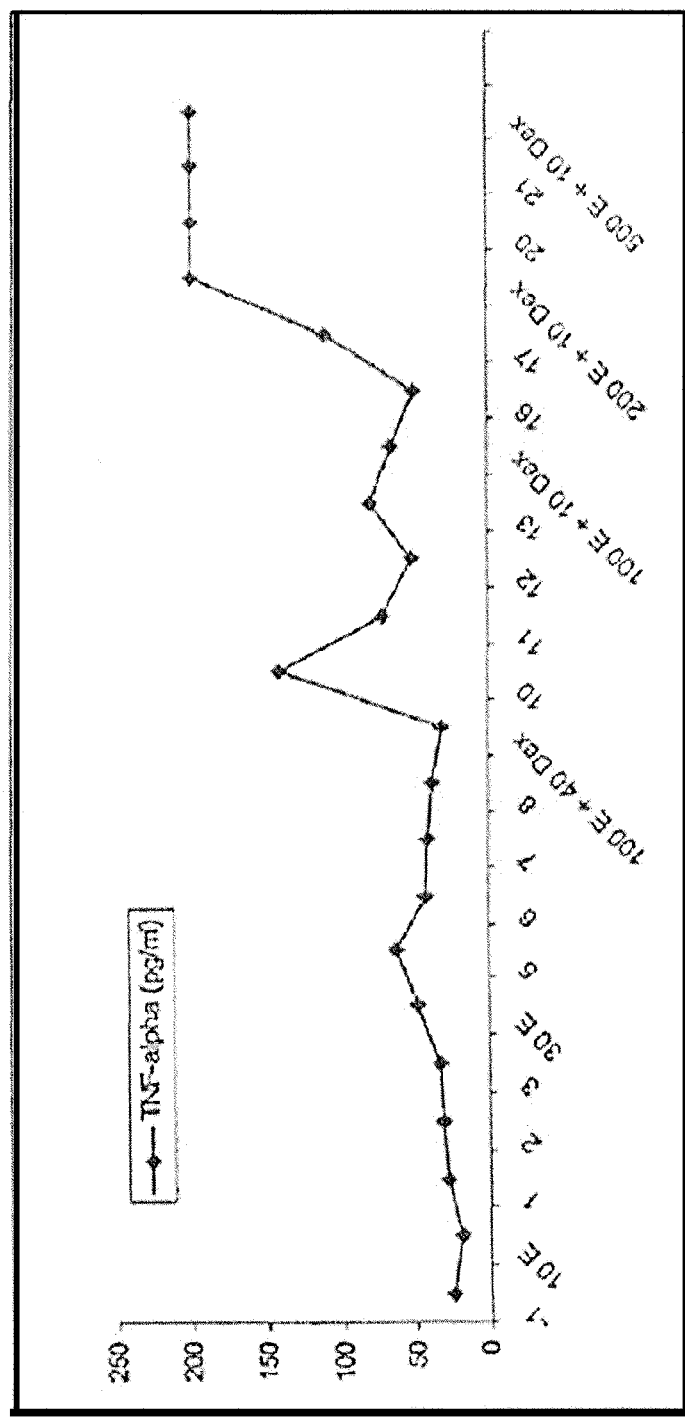

FIG. 6D shows the curve of the TNF-α concentration in the serum (in µg/ml) that was measured in the patient with the gastric carcinoma. TNF-α rises under the therapy with an increase in dose from 10 µg to 500 µg of the immunotherapeutic antibody as an expression of a cellular immune activity from a value of below 50 pg/ml in the case of low-dosed antibody monotherapy to about 200 pg/ml in the case of a dose of 200 µg or 500 µg i.p. of the bispecific antibody plus, in each instance, 10 mg i.v. dexamethasone. Consequently, by reason of the administration of the glucocorticoid, which suppresses the side-effects and which enables a considerable increase in the dose of the immunostimulatory antibody, an outstanding cellular specific immune activity is observed in the course of the therapy or use, according to the invention, of the glucocorticoid.

Figure 6E:
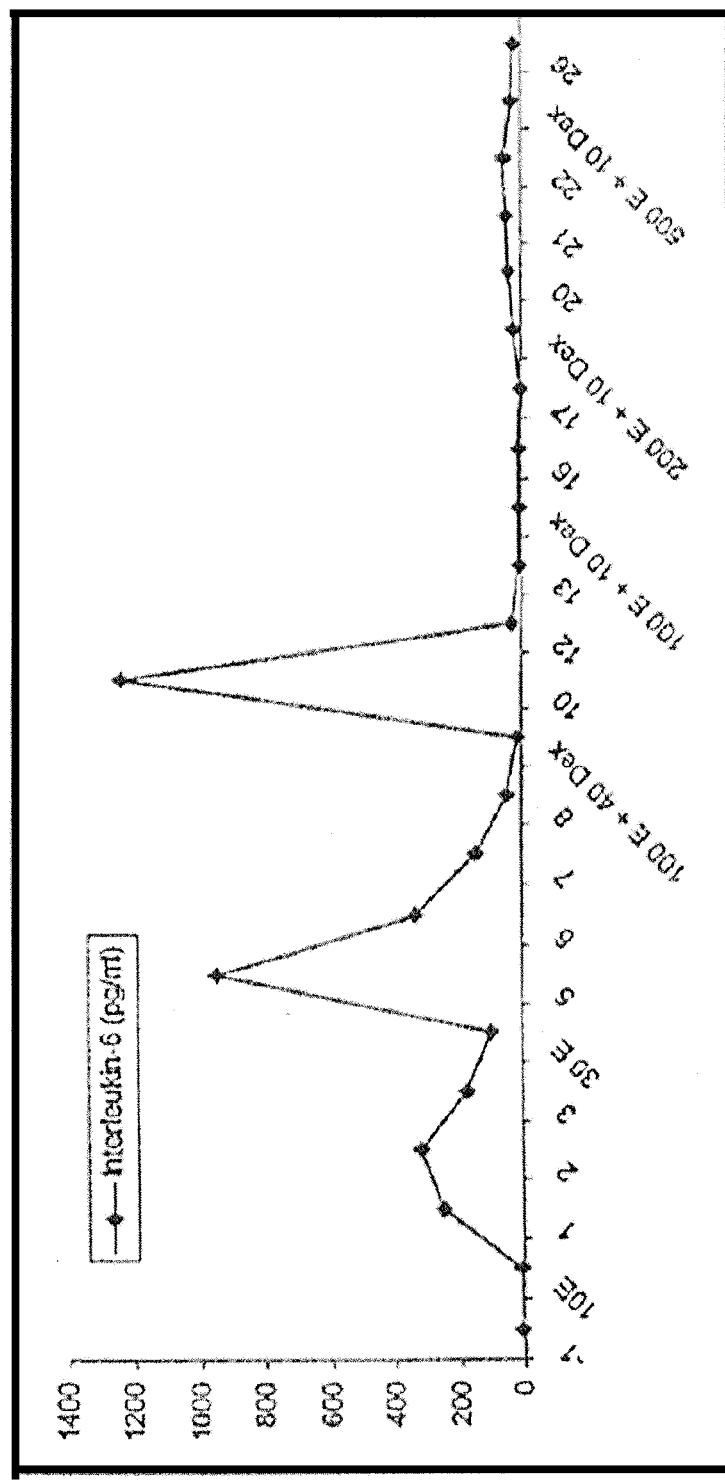

FIG. 6E shows the curve of the IL-6 concentration in the serum (in pg/ml) of the patient with gastric carcinoma under the therapy plotted on the x-axis. After the first and second administrations of the immunostimulating antibody without simultaneous administration of dexamethasone (on day 0 and day 4), distinct increases in the IL-6 concentration to about 300 pg/ml and just under 1000 pg/ml, respectively, are to be recorded. Also after the first combined administration of antibody and glucocorticoid (100 µg antibody i.p. plus 40 mg dexamethasone i.v. on day 9), a brief rise in the IL-6 concentration with a maximum value of about 1200 pg/ml is to be observed. However, the IL concentration attains base values again very quickly and remains constant at low values despite increase of the antibody dose up to 500 µg i.p., accompanied by simultaneous administration of 10 mg dexamethasone i.v.

The values of the immunological parameters established in a patient with gastric carcinoma show that under the combined therapy with trifunctional bispecific antibody of the specificity anti-EpCAM x anti-CD3 plus dexamethasone a distinct cellular specific immune activity is triggered, as the rise in the TNF-α concentration shows. All the other parameters remain largely constant under the immense increase in dose of the antibody, by reason of the administration of the glucocorticoid. In this regard it is to be noted that, except for TNF-α, none of the measured immunological parameters reflects the antibody-mediated action on the tumour cell, but corresponds to the immunological side-effect. In particular, despite the great increase in dose of the antibody, accompanied by simultaneous application of dexamethasone, no indication of a SIRS (systemic inflammatory response syndrome) is evident. SIRS is an inflammatory syndrome which arises by reason of an intense systemic release of cytokine in antibody therapies, in particular immunostimulatory therapies, in high dose, and may be associated with an organ failure, which may even have a fatal outcome. The immunological parameters observed in a patient with a chemotherapy-resistant gastric carcinoma under the combined therapy according to the invention surprisingly show no indications whatsoever of a severe side-effect of such a type.

Figure 7A:
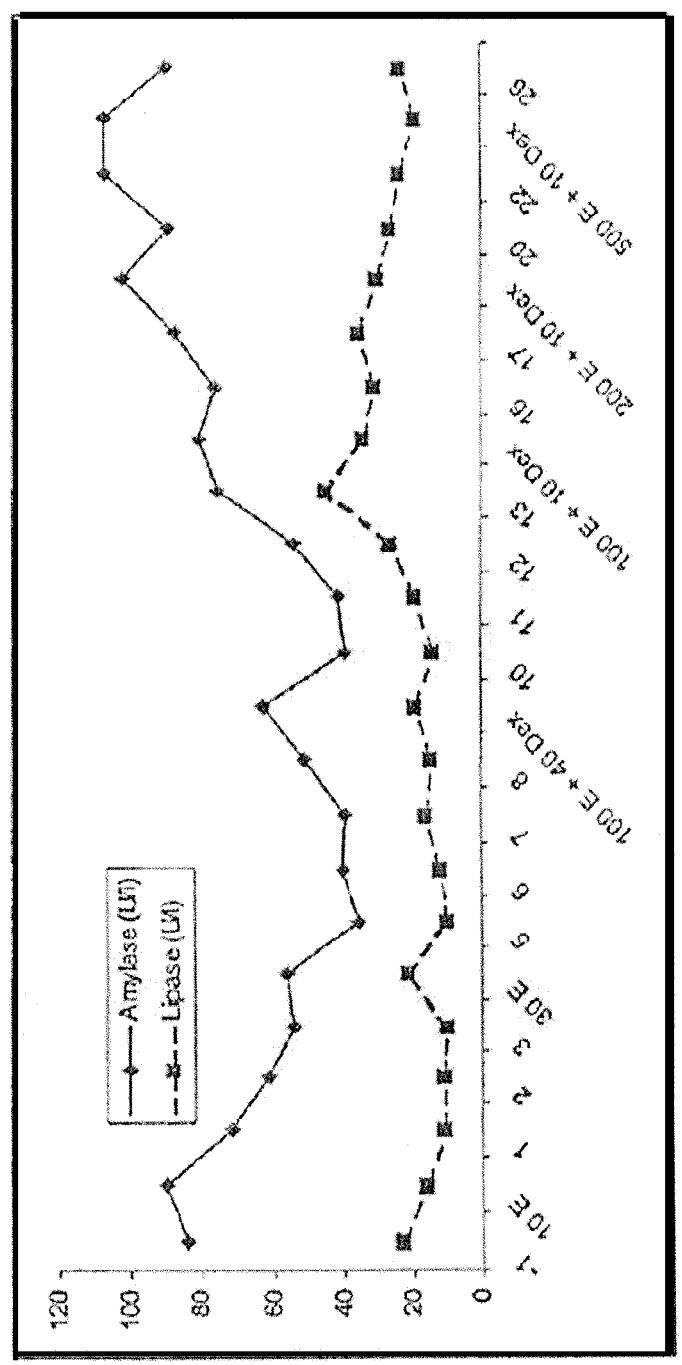
Figure 7B:
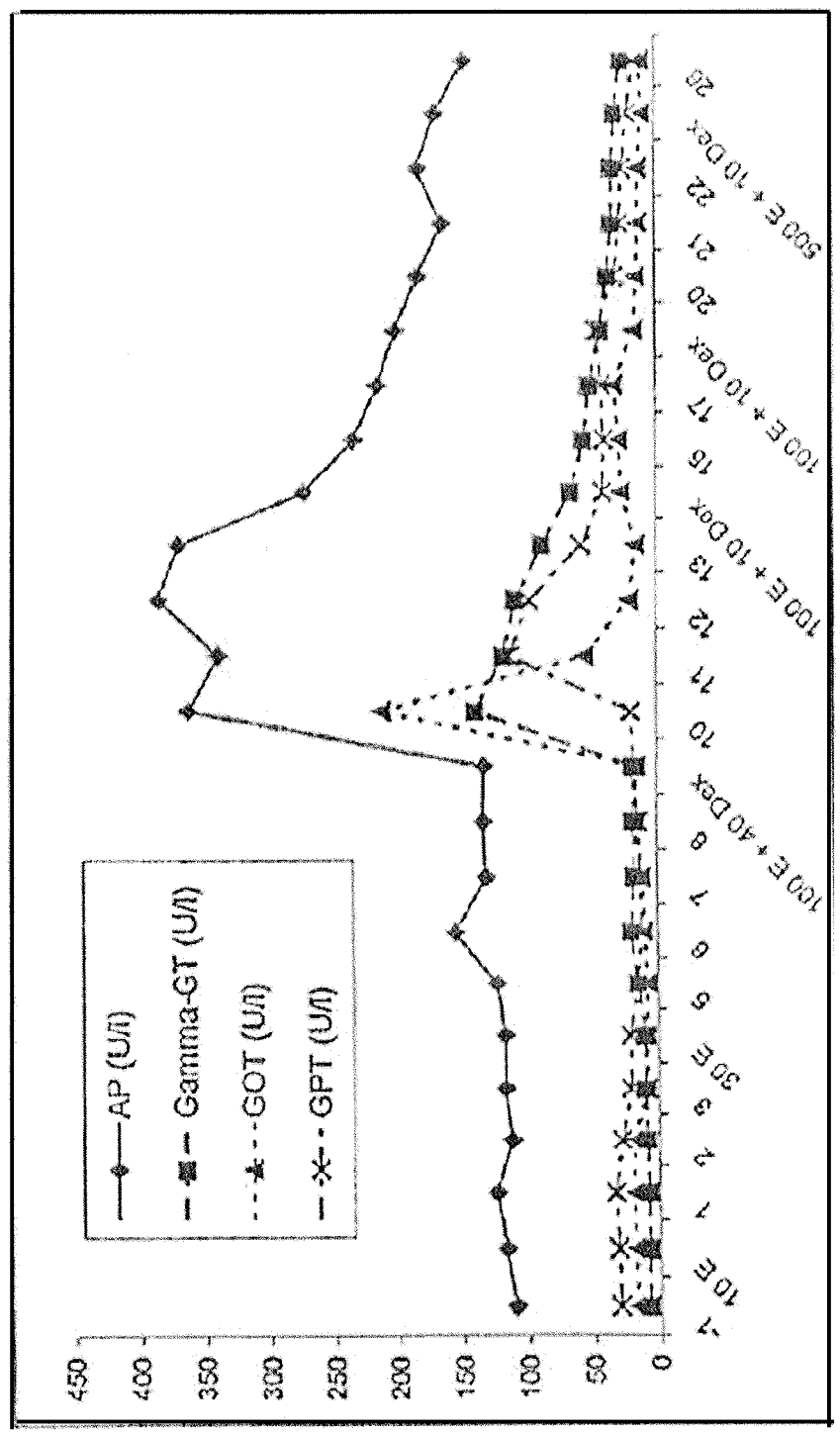
Figure 7C:
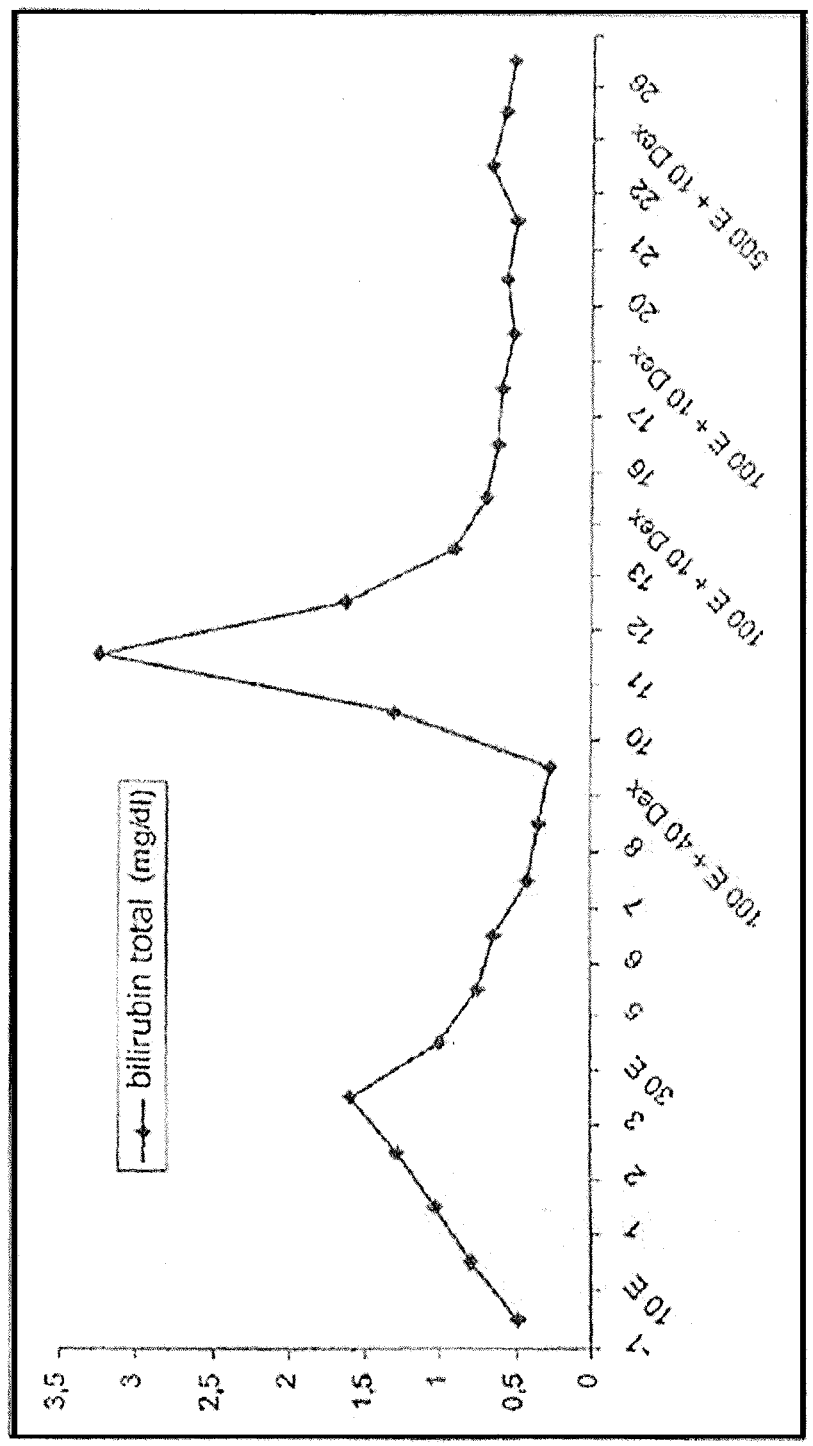

FIG. 7A-7C shows diagrams that represent the side-effects of the therapy, presented above, of a patient with chemotherapy-resistant gastric carcinoma on the pancreatic values and hepatic values.

FIG. 7A shows the serum-concentration curve of the pancreas-specific enzymes α-amylase (♦) and lipase (■), in each instance in U/l. In no pancreas parameter does an abnormal increase occur as a sign of an undesirable side-effect, despite a great increase in dose of the immunostimulatory antibody in the combined treatment according to the invention. (Normal values of a healthy adult: α-amylase<120 U/l; lipase<190 U/l)

FIG. 7B shows the corresponding curve of the serum concentrations of the liver-specific enzymes alkaline phosphatase (AP; ♦), γ-glutamyltransferase (γ-GT; ■), glutamate oxaloacetate transaminase (GOT; ▲) and glutamate pyruvate transaminase (GPT; x) (in each instance in U/l) under the therapy, described above, of a patient with gastric carcinoma. The reference ranges of the serum concentrations of the measured enzymes amount to the following: AP: 40 to 190 U/l; γ-GT: 4 to 18 U/l; GOT: 5 to 15 U/l; GPT: 5 to 19 U/l. Merely at the start of the antibody/glucocorticoid combined therapy (therapy days 10 to 13) does an increase arise in the serum concentrations of the hepatic enzymes, particularly of the AP, which, however, return to the normal values within a short time. Consequently, also in the case of the concentrations of the liver-specific enzymes no increase corresponding to the increase in dose of the immunostimulating antibody occurs as a sign of an undesirable side-effect when accompanied by simultaneous administration of dexamethasone.

FIG. 7C represents in a diagram the total concentration of bilirubin (in mg/dl) by way of further hepatic parameter as a function of the course of therapy of the patient with gastric carcinoma. Apart from a rapidly passing increase in bilirubin after the increase in dose of the immunostimulating antibody from 30 µg to 100 µg, in the case of a further increase in dose this hepatic parameter also lies within the reference range of below 1 mg/dl. Therefore despite very high dosage of the bispecific antibody in the case of administration of dexamethasone no increase in bilirubin is established that would indicate an undesirable side-effect. In this context it was significantly established that the patient showed no serious clinical side-effects whatsoever under the therapy with simultaneous administration of dexamethasone and immunostimulating antibody (cf. Example 4 below).

A further patient was subjected to immunotherapy in accordance with the invention with an antibody (trifunctional bispecific antibody with the specificity anti-EpCAM x anti-CD3) and dexamethasone. It was a question of a female patient with an adenocarcinoma and with diffuse hepatic metastasis. The application of the antibody was undertaken via a selective catheter into the A. hepatica dextra. In FIG. 8A-8E, diagrams are shown once again that document the course of immunological parameters as a function of the therapy. The graphic representation of the parameters was effected as stated above in connection with FIG. 6A-6E.

Figure 8A:
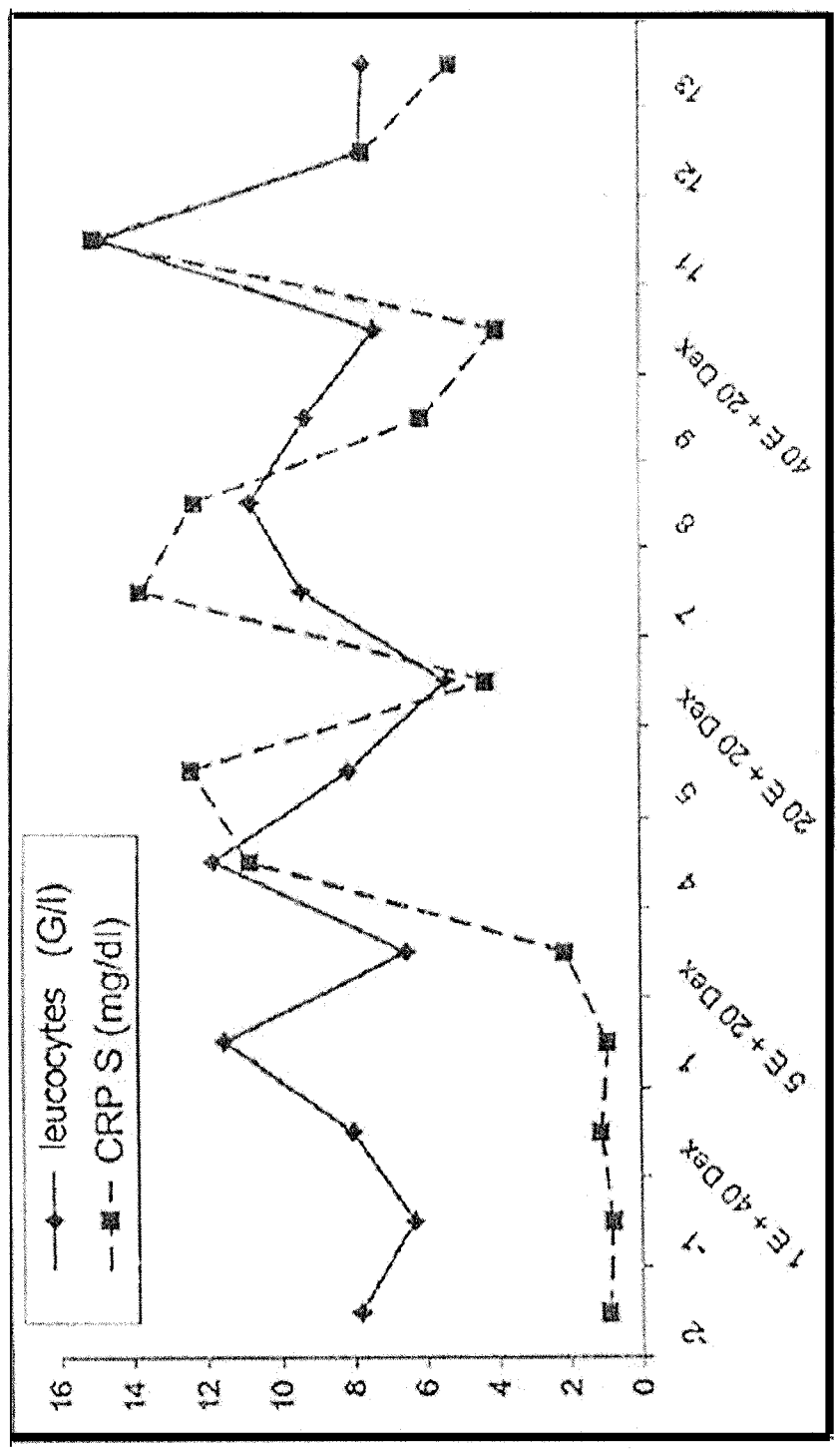
Figure 8B:
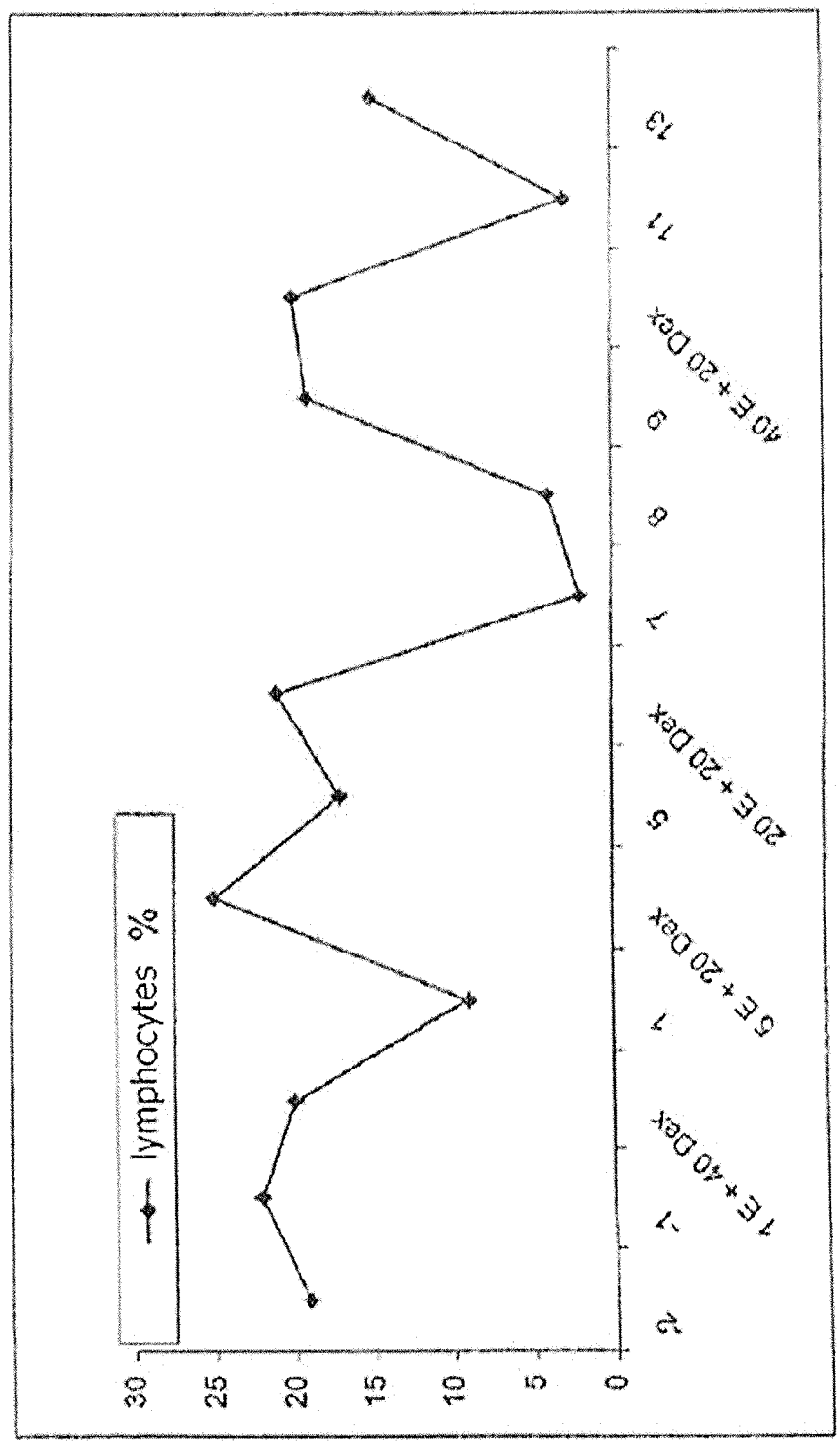
Figure 8C:
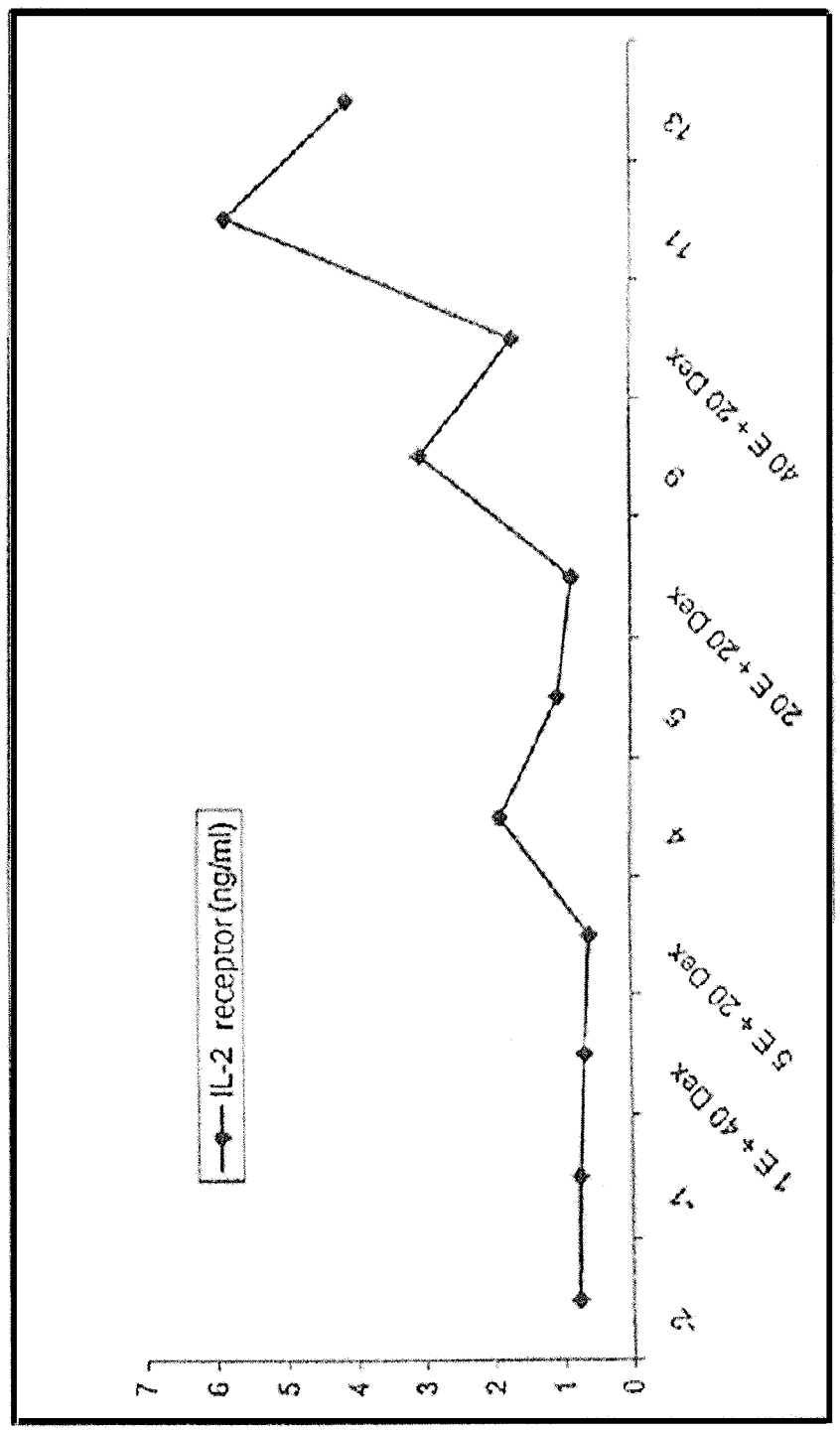
Figure 8D:
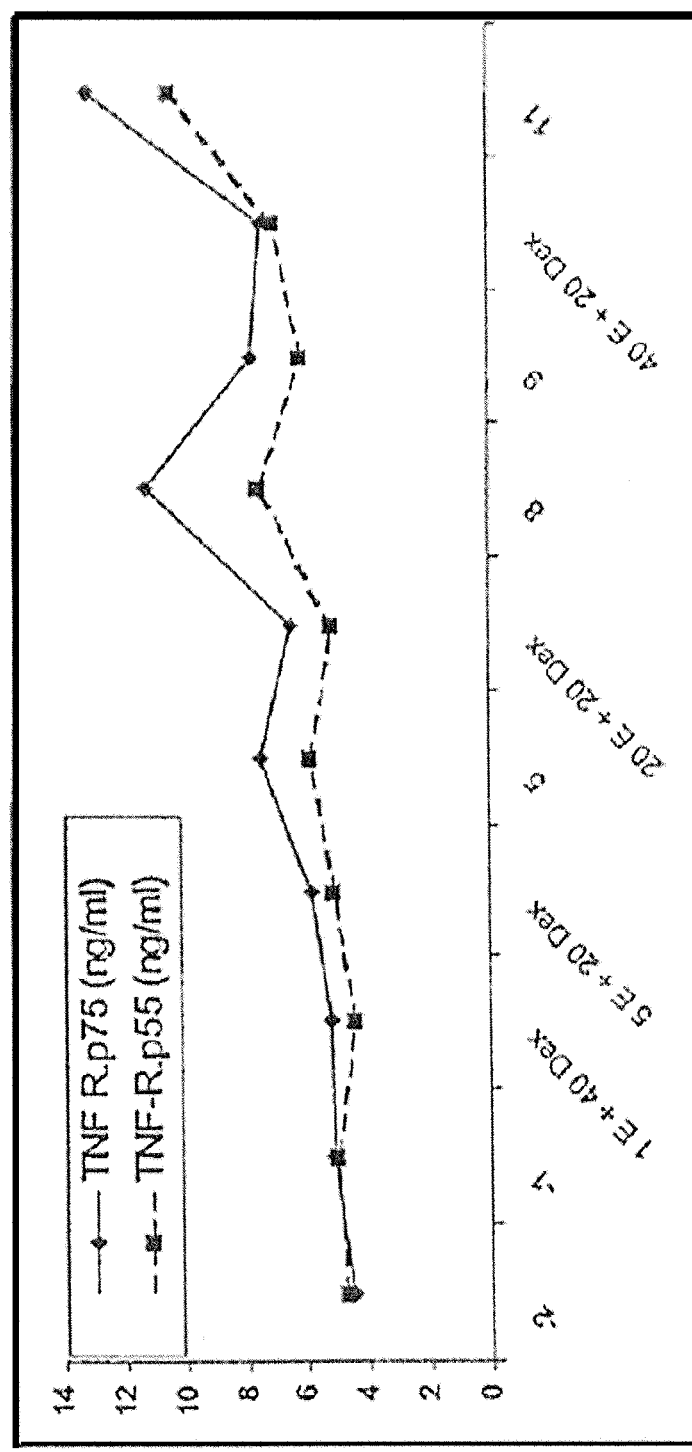
Figure 8E:
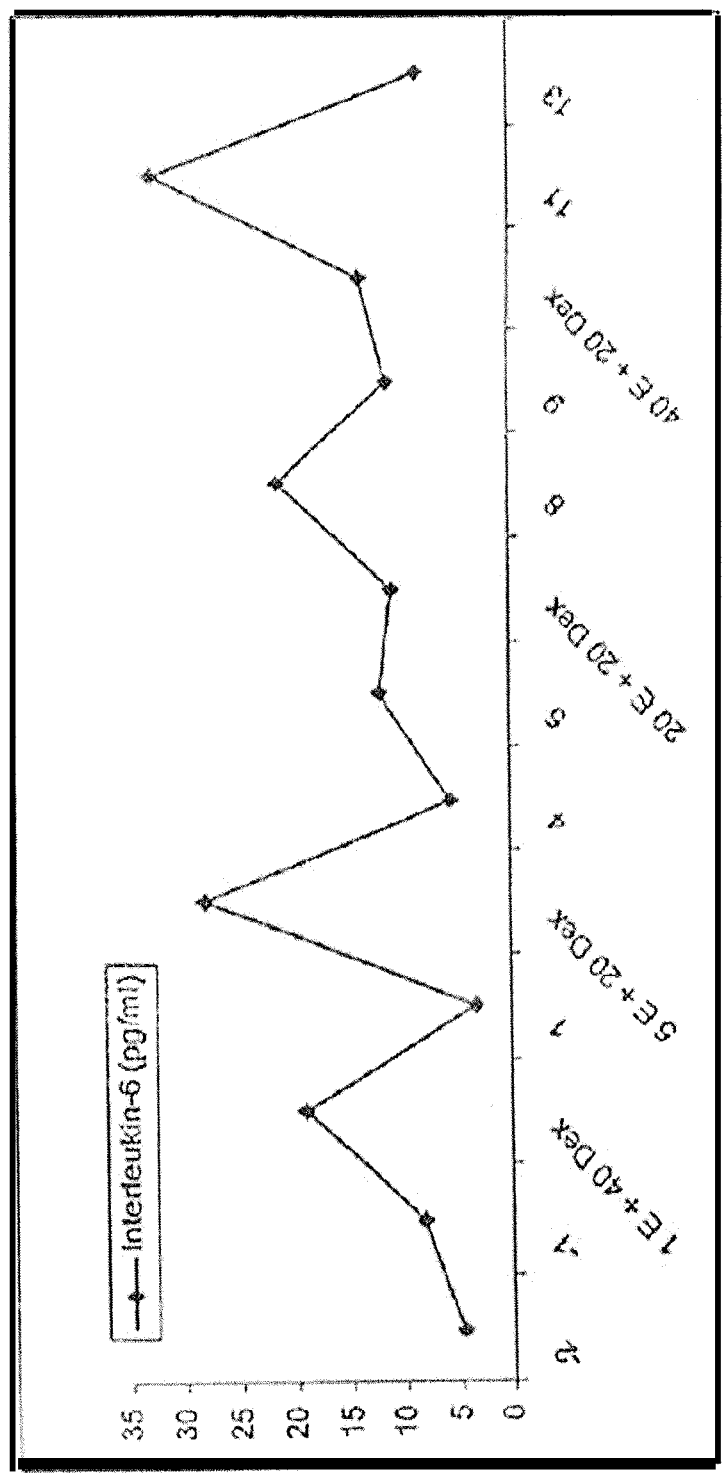

FIG. 8A shows the curve of the leucocyte number and the CRP-serum concentration, FIG. 8B represents the percentage fraction of the lymphocytes in the differential blood count as a function of the course of therapy, FIG. 8C reproduces the curve of the concentration of the IL-2 receptor, FIG. 8D is a corresponding plotting for the TNF receptor p75 and the TNF receptor p55, and FIG. 8E finally shows the curve of the IL-6 concentration under the combined therapy according to the invention. Under the therapy a systemic rise in the soluble IL-2 receptor (FIG. 8C) and in the TNF receptors p55 and p75 (FIG. 8D) occurred despite the administration of dexamethasone, reflecting the desired immune activation against tumour cells. At the same time, under an increase in dose from 1 µg antibody to 40 µg antibody, i.e. in the case of an increase by a factor of 40, no significant increase occurred in the leucocytes, in the serum CRP, in the percentage fraction of the lymphocytes, and no significantly increased systemic release of IL-6 occurred (cf. FIGS. 8A, 8B and 8E).

Figure 9A:
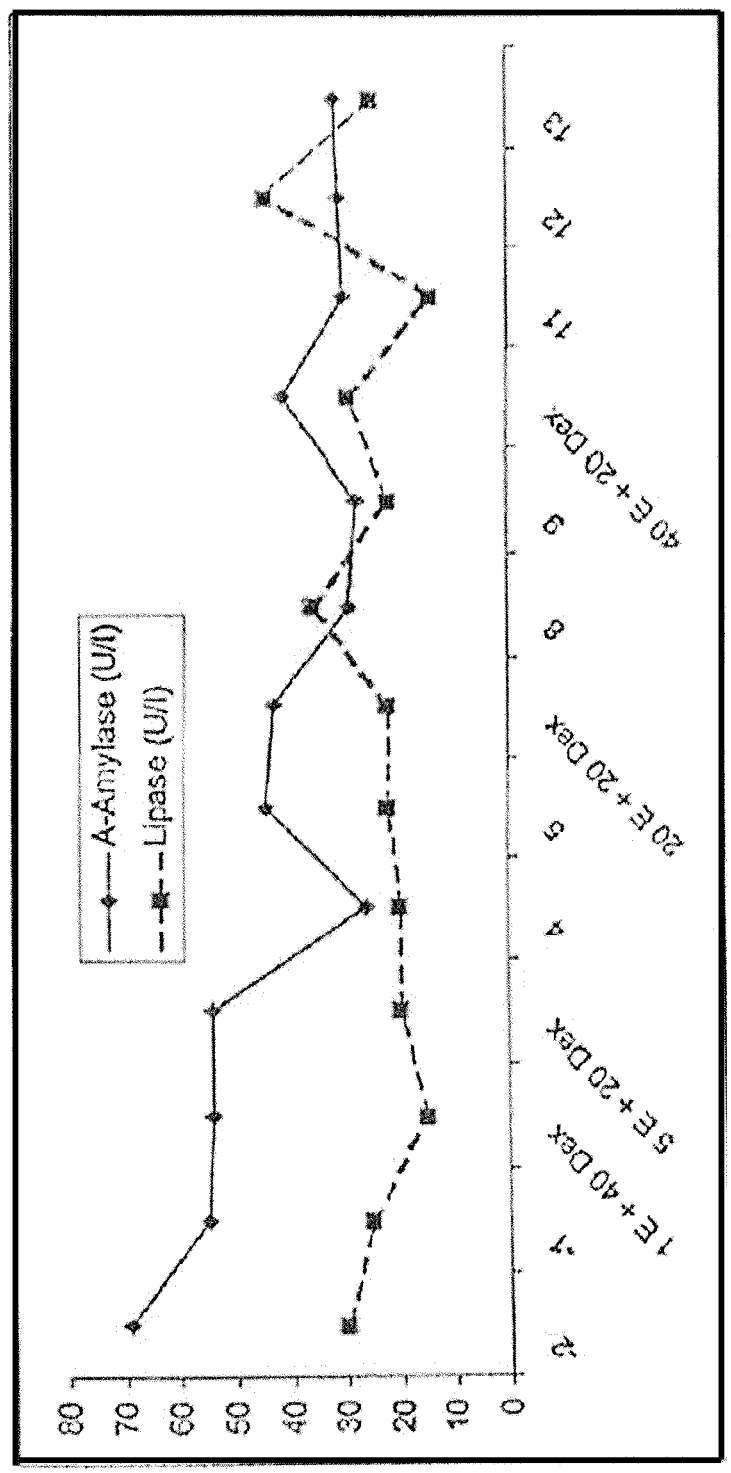

Pancreas-specific and liver-specific laboratory values were also determined in the female patient suffering from an adenocarcinoma with diffuse hepatic metastasis during the therapy with use, according to the invention, of the glucocorticoid together with the above immunostimulating antibody. The results of these investigations are compiled in FIG. 9A-9C. The plotting was effected as specified above in connection with FIG. 7A-7C in the case of the patient with gastric cancer.

FIG. 9A shows, once again, the serum concentrations of the pancreas-specific enzymes α-amylase and lipase (in each instance in U/l) as a function of the therapy represented on the x-axis. The pancreatic values were within the reference range during the entire therapy.

Figure 9B:
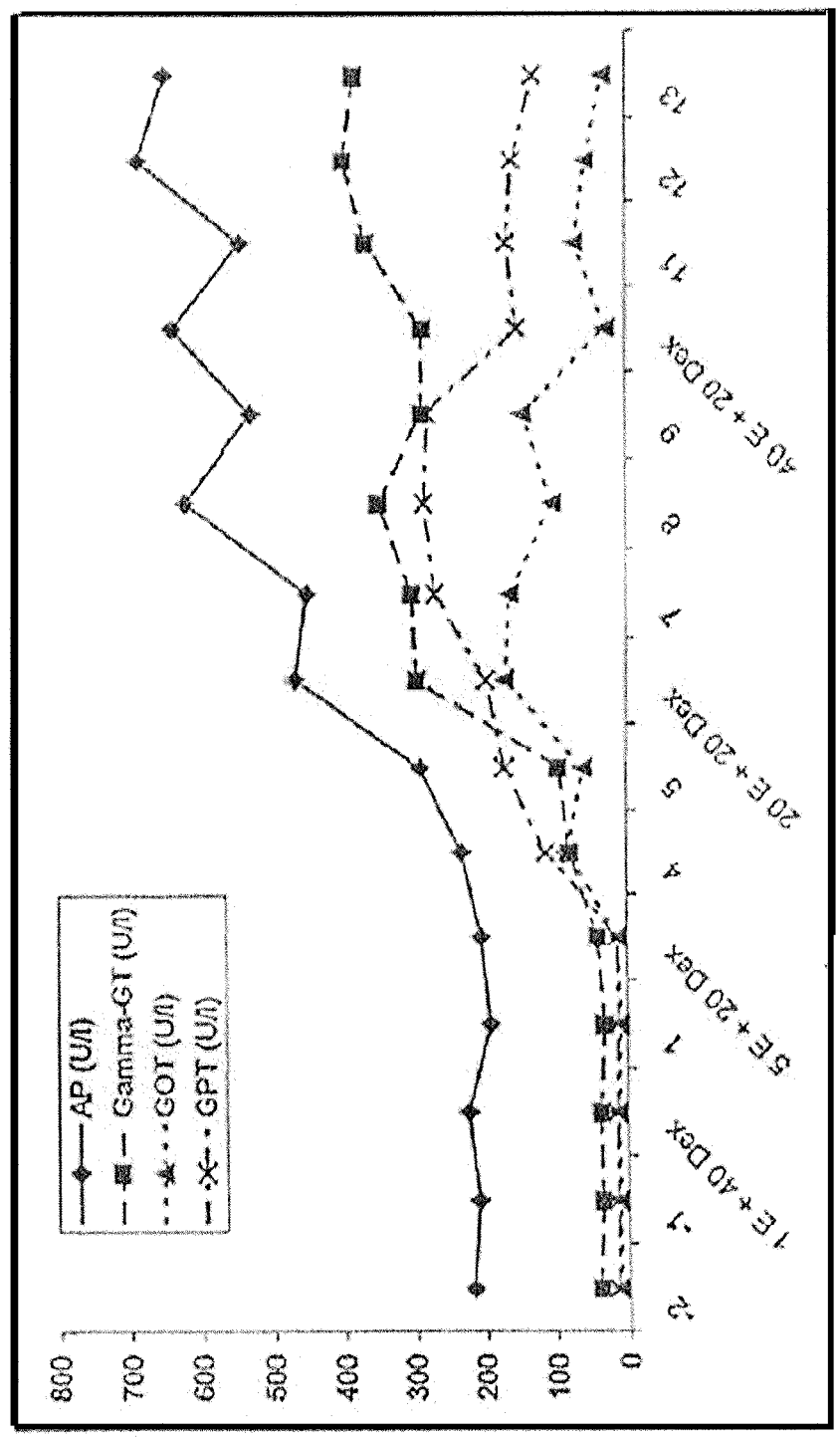
Figure 9C:
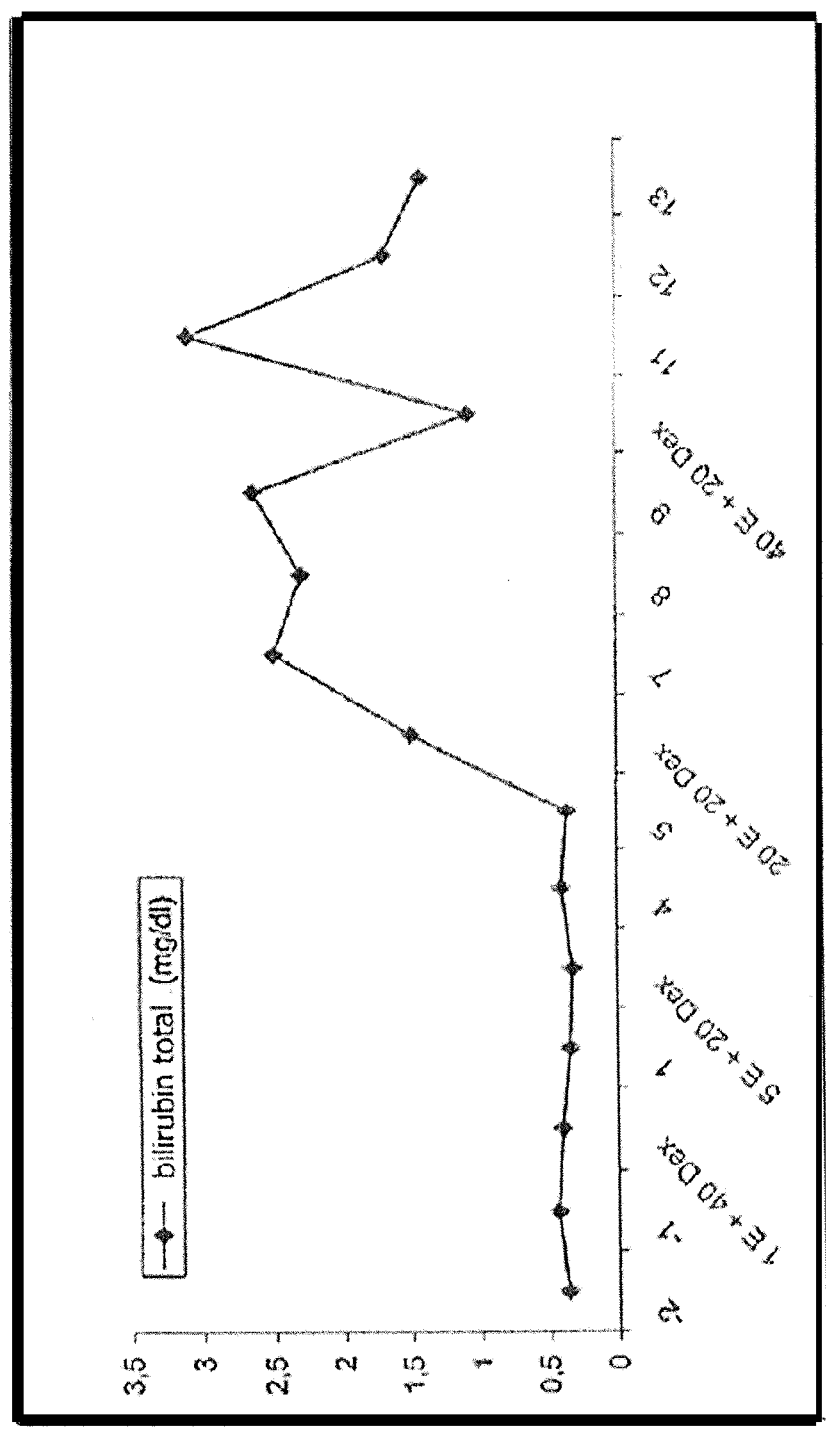

FIG. 9B shows a corresponding plotting of the liver-specific enzymes AP, γ-GT, GOT and GPT (likewise in U/l). A rise in the AP in the case of an increase in the antibody dose from 5 µg to 40 µg, starting from 200 U/l to about 700 U/l, is indeed to be recorded. Similarly, the concentrations of γ-GT and GPT rise under this increase in dose from distinctly below 100 to just under 400 U/l and 150 U/l, respectively. This rise in the concentrations of the liver-specific enzymes does not, however, indicate worrying side-effects, since after conclusion of the therapy the increase was fully reversible, and clinical problems did not arise in the patient at any time. This also applies, incidentally, to the curve of the total bilirubin concentration, which has been represented in FIG. 9C as a function of the course of therapy and which constitutes a further liver-specific laboratory parameter. The rise in the total bilirubin concentration from 0.5 mg/dl in the case of a 5 µg antibody dose to 3 mg/dl to 3.5 mg/dl in the case of an antibody dose of 40 µg shows no significant side-effect of the therapy on the liver of the patient. In this context it is likewise to be borne in mind that the hepatic values of the patient, particularly the liver-specific enzymes, were elevated by reason of the existing hepatic metastases.

Figure 10A:
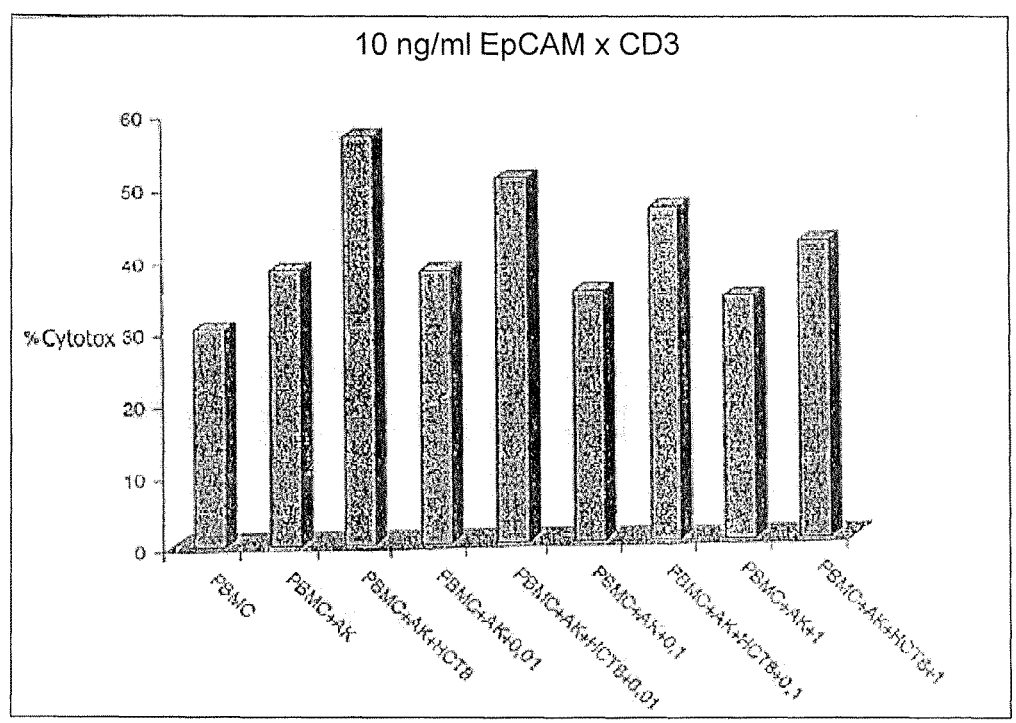
Figure 10B:
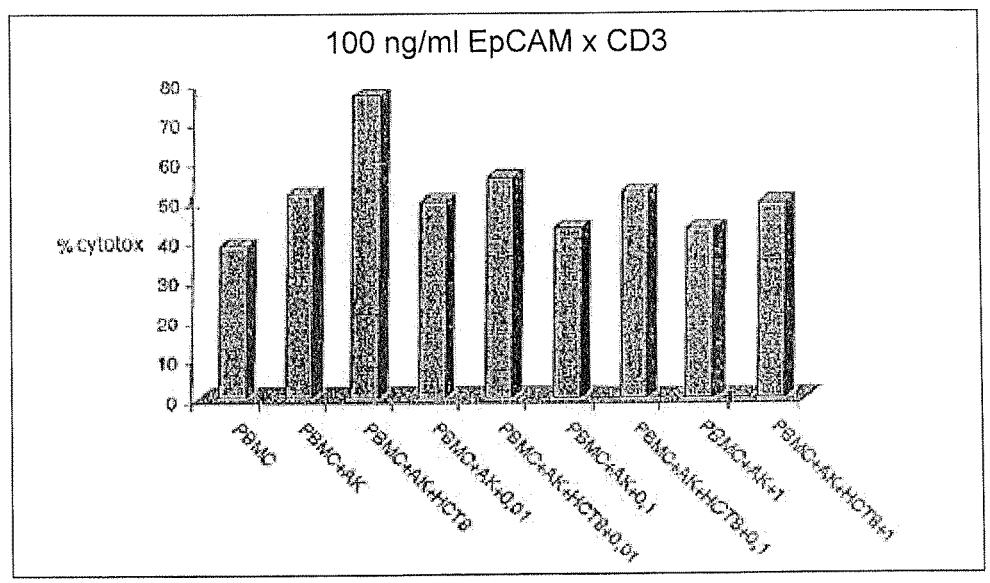
Figure 10C:
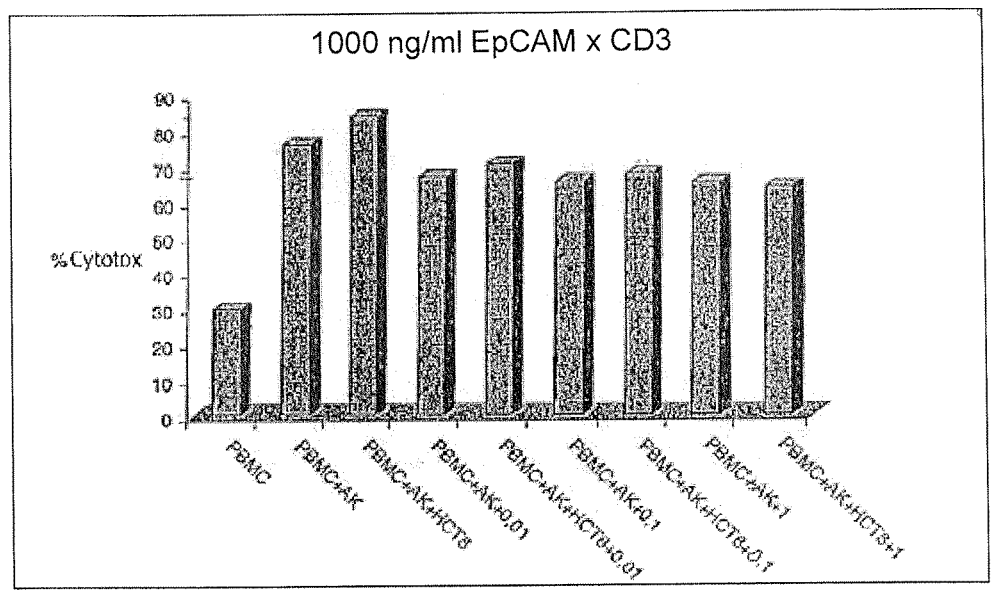
Figure 10D:
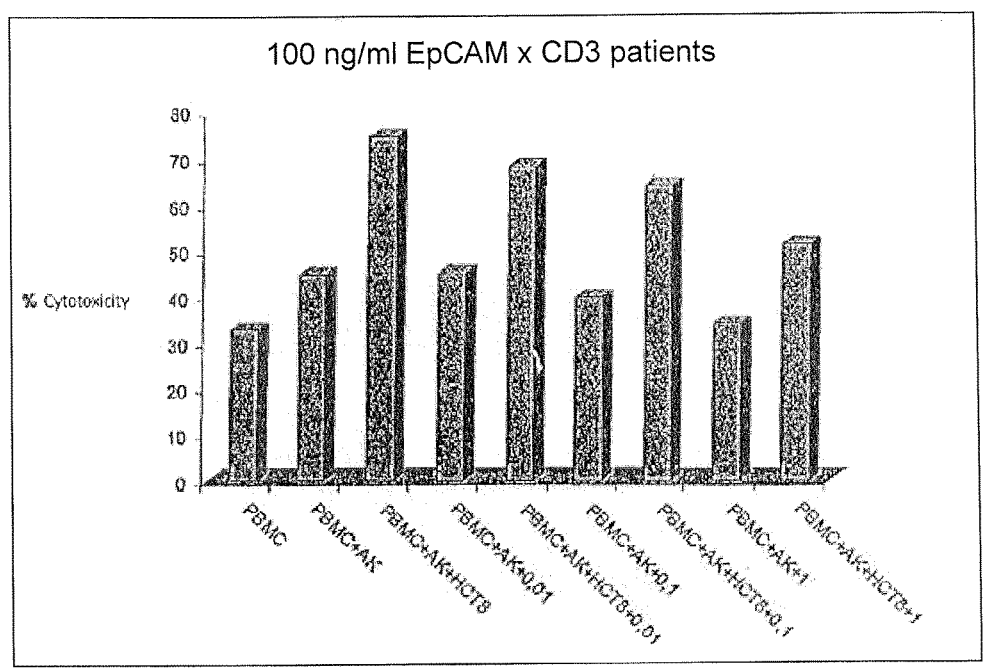

FIG. 10A-10D shows graphic representations of cytotoxicity assays in which the results of the measurements of the specific percentage cytotoxicity were determined using fluorescence-marked HCT8 tumour cells. FIGS. 10A to 10C represent the mean values of the measurements carried out in respect of three healthy test subjects, whereas FIG. 10D represents the mean values of the measurements carried out in respect of six patients with gastrointestinal carcinoma. In the experiments a stimulation was effected with trifunctional bispecific antibodies with the specificity anti-EpCAM x anti-CD3 at various concentrations amounting to 10 ng/ml, 100 ng/ml and 1000 ng/ml. The respective concentration of the antibody that has been used is specified in FIGS. 10A to 10D. The concentration of the PBMC amounted to $10^6$ cells/ml, that of the HCT8 cells amounted to $5 \times 10^4$ cells/ml. In each of the experiments the stimulation was effected with the antibody without HCT8 cells (PBMC+AK), in the presence of HCT8 cells (PBMC+AK+HCT8), and subject to additional administration of dexamethasone in concentrations of 0.01 µg/ml, 0.1 µg/ml, 1.0 g/ml (PBMC+AK+0.01 and 0.1 and 1, respectively). On the y-axis the percentage cytotoxicity has been plotted; on the x-axis the respective experimental assay of the PBMC has been plotted, with unstimulated PBMC serving by way of control (PBMC).

FIG. 10A shows the results of the corresponding measurements in the case of an antibody concentration of 10 ng/ml. In the case of stimulated PBMC with contact with HCT8 target cells and administration of dexamethasone, an inhibition of the specific percentage cytotoxicity by approximately 15 percentage points (from about 55% to 41%) arises, said inhibition increasing with increasing dexamethasone concentration. The percentage inhibition turns out to be more distinct in the case of contact with HCT8 than in the experimental assays that have no contact with HCT8 cells. Here an inhibition by merely about 5 percentage points occurs.

FIG. 10B represents the results of the measurements in the case of an antibody concentration of 100 ng/ml. In the case of stimulated PBMC with contact with HCT8 target cells, a distinct inhibition of the specific percentage cytotoxicity of up to about 30 percentage points (from about 78% to 50%) arises if the additional administration of dexamethasone was effected, said inhibition increasing with increasing concentration of dexamethasone. In contrast thereto, only a slight inhibition of the cytotoxicity, by approximately 10 percentage points, arises in the case of stimulated PBCM without contact with HCT8 and administration of dexamethasone, which likewise increases with increasing concentration of dexamethasone.

FIG. 10C shows the results of the corresponding measurements in the case of an antibody concentration of 1000 ng/ml. An inhibition of the cytotoxicity occurs by virtue of dexamethasone, though this turns out to be smaller overall than is the case with a stimulation with an antibody concentration of 100 ng/ml (FIG. 10B). In the case of stimulated PBMC with contact with HCT8 target cells, an inhibition of the specific percentage cytotoxicity by up to about 20 percentage points (from about 85% to 67%) arises if the additional administration of dexamethasone was effected, said inhibition increasing with increasing concentration of dexamethasone. In the experimental assays of stimulated PBMC without contact with HCT8 and in the case of administration of dexamethasone merely a minimal inhibition of the cytotoxicity by about 2 percentage points arises, which again increases with increasing concentration of dexamethasone.

FIG. 10D shows the corresponding average measurements in the case of tumour patients with gastrointestinal tumours. These measurements were carried out at an antibody concentration of 100 ng/ml. As can also be seen here, a distinct inhibition of the cytotoxicity by approximately 27 percentage points (from about 78% to 51%) occurs under administration of dexamethasone. The inhibition once again turns out to be greater if a stimulation with contact with HCT8 target cells is effected. The results are comparable, from the point of view of antibody concentration, with those from FIG. 10B (healthy test subjects). From such a comparison it can be noted that both in healthy test subjects and in tumour patients a distinct inhibition of the specific percentage cytotoxicity occurs by virtue of administration of the glucocorticoid dexamethasone.

Figure 11:
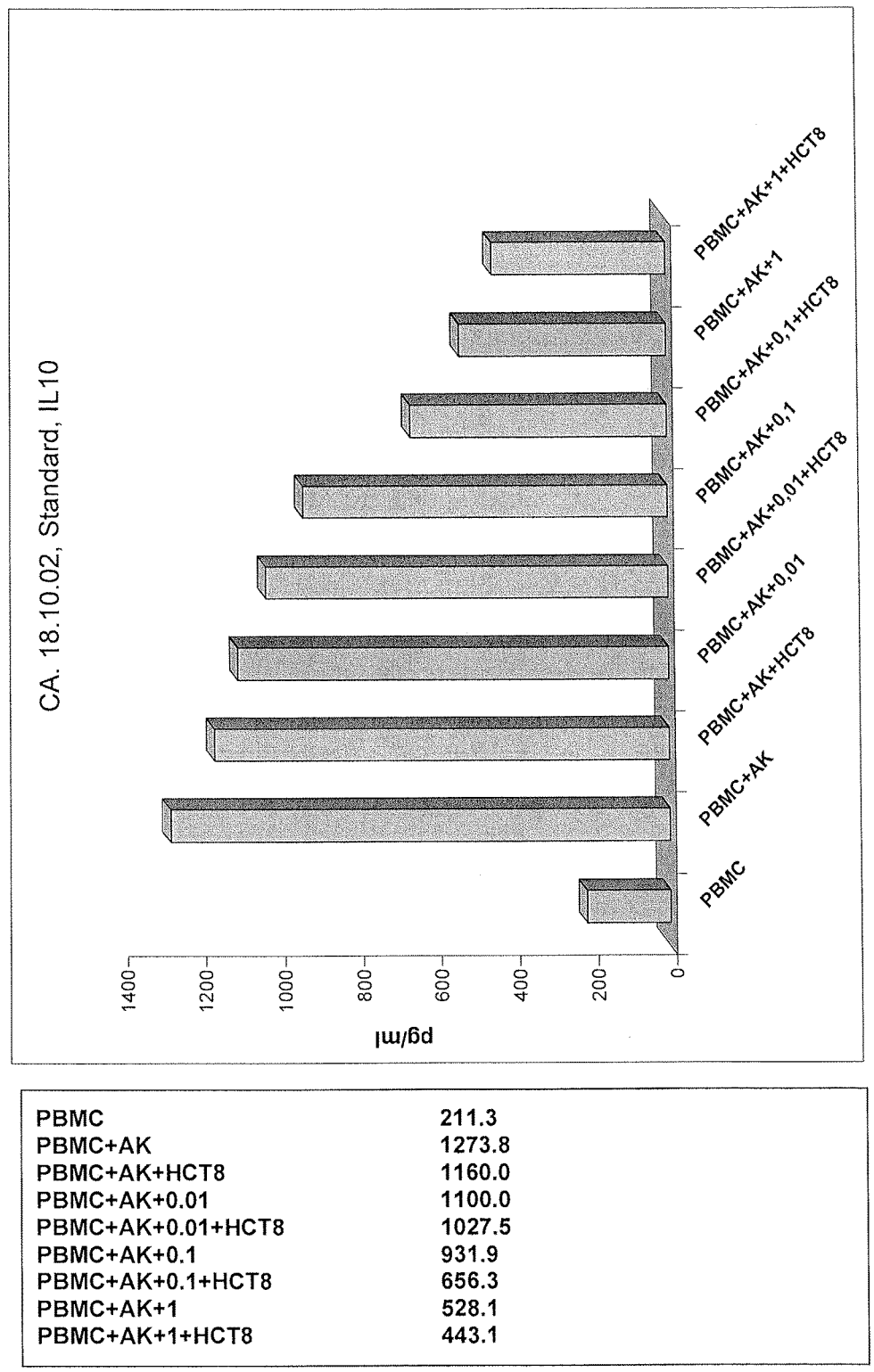
Figure 12:
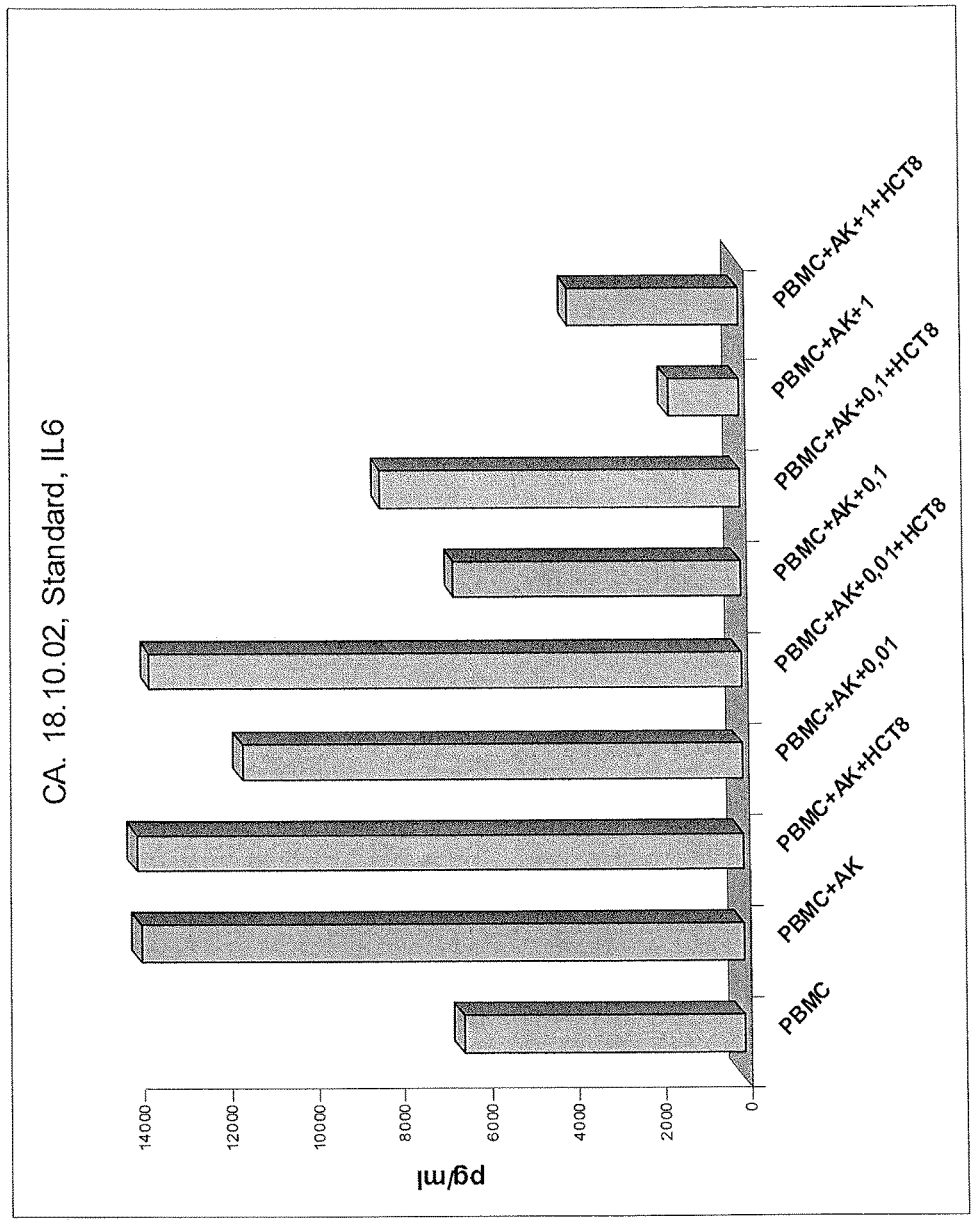
Figure 13:
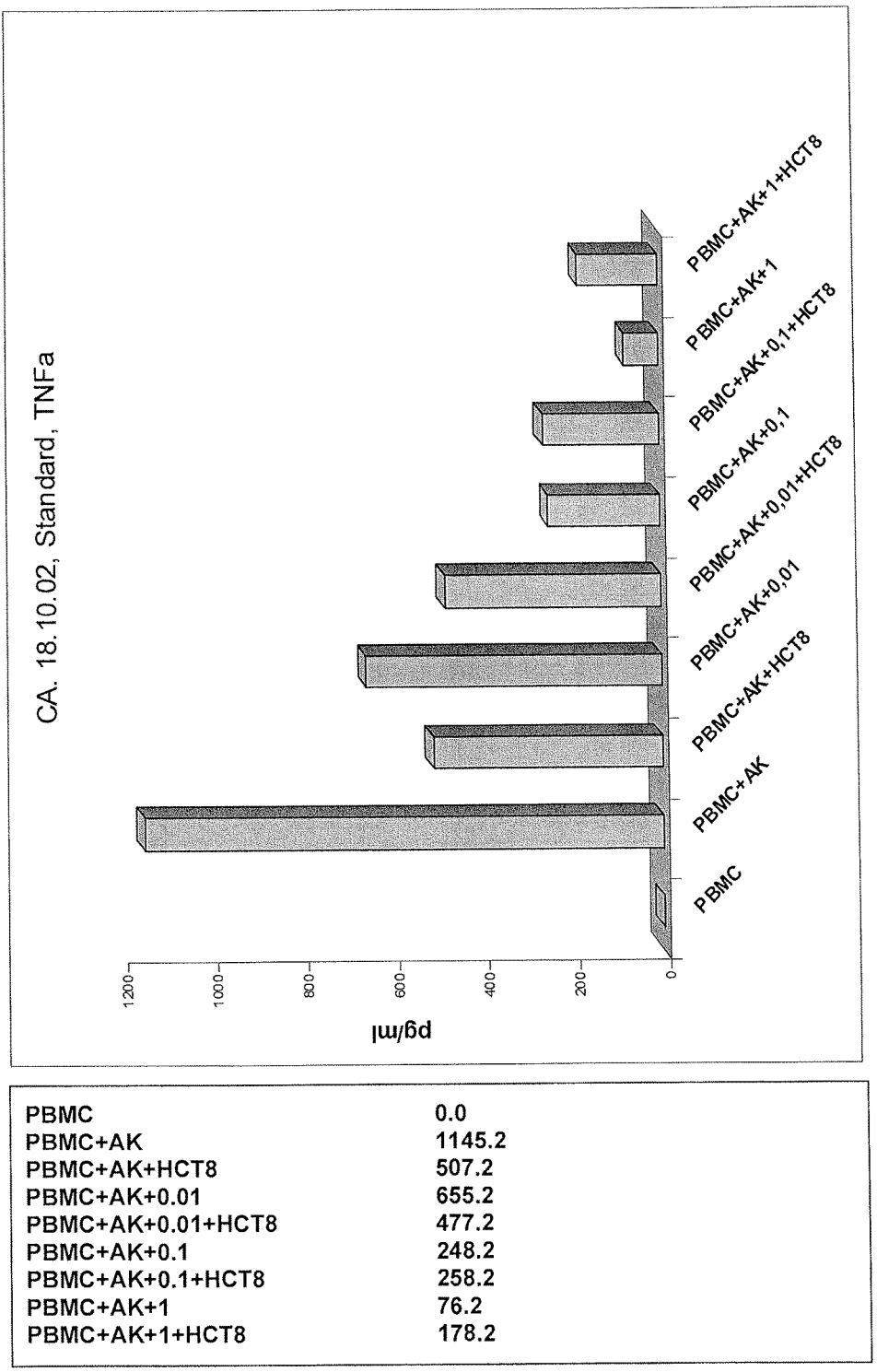

FIGS. 11 to 13 Show graphic representations of the results of the release of various cytokines in healthy test subjects by PBMC (at a concentration of $10^6$ cells/ml) after stimulation with a trifunctionally bispecific antibody of the specificity anti-EpCAM x anti-CD3 (AK) (at a concentration of 100 ng/ml) without and in the presence of EpCAM-positive tumour cells (HCT8) (at a concentration of $5 \times 10^4$ cells/ml). On the y-axes the concentration of the respective cytokine in pg/ml has been plotted. On the x-axes the respective stimulation assays of the PBMC have been plotted. The respective concentration of the added dexamethasone in µg/ml is specified by "0.01", "0.1" and "1". The values of unstimulated PBMC by way of control are likewise specified ("PBMC").

Figure 1A:
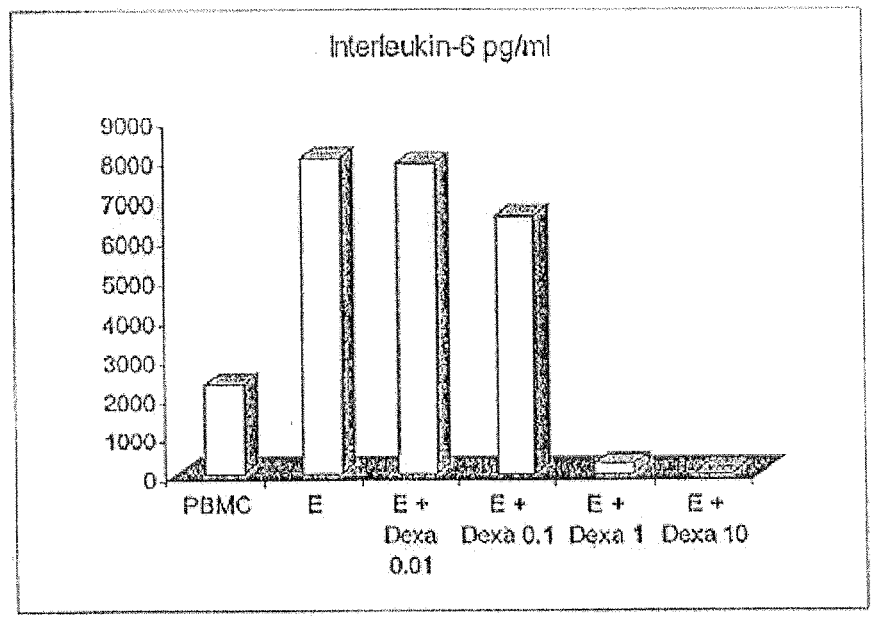
FIG. 1A-1C shows graphic representations that document the release of interleukin-6 (IL-6) by mononuclear cells of the peripheral blood (PBMC) (concentration $10^6$ cells/ml) after a stimulation without and with EpCAM-positive tumour cells (concentration $5 \times 10^4$ cells/ml).
Figure 1B:
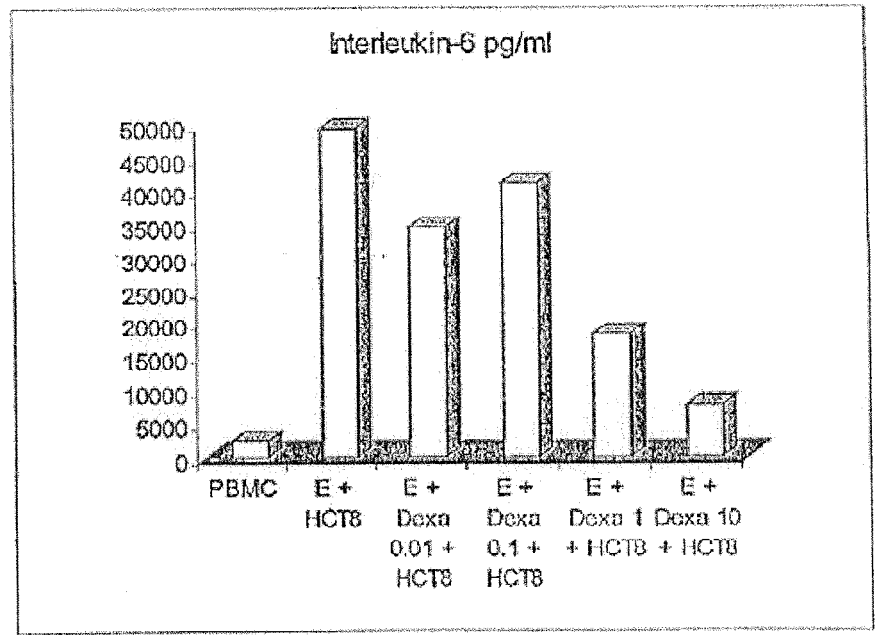
Figure 1C:
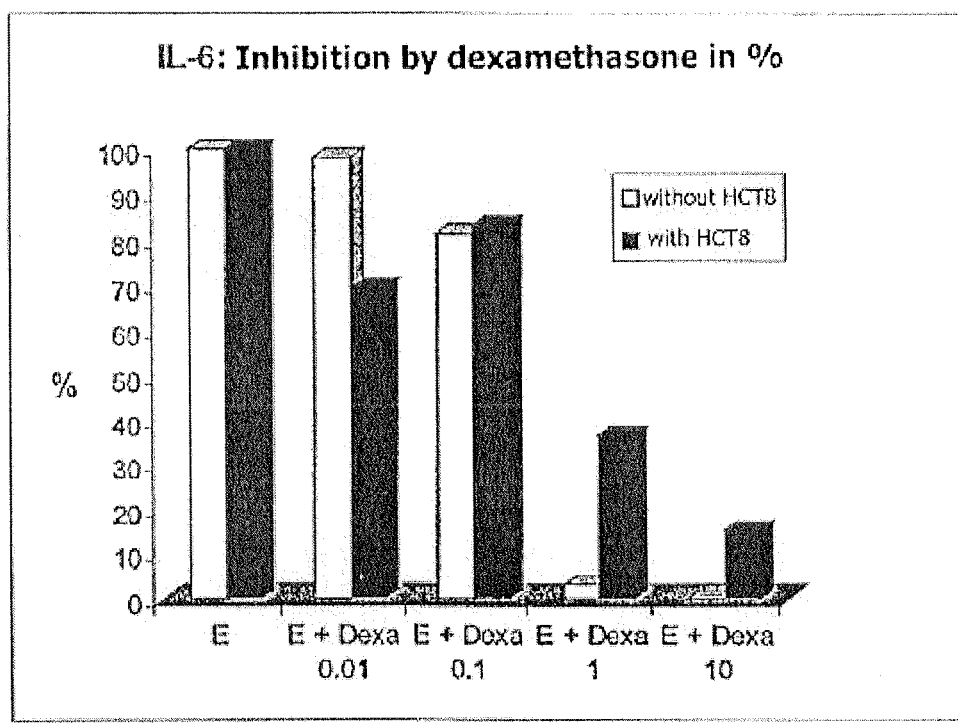

The stimulation of the PBMC without contact with EpCAM-positive tumour cells (HCT8 cells) corresponds (as also in FIGS. 1 to 3) to the non-specific release of cytokine, which is independent of the antigen binding (antibody/antigen interaction). The release of the respective cytokines is accordingly effected systemically by the totality of the PBMC. The stimulation of the PBMC with contact with EpCAM-positive tumour cells corresponds, on the other hand, to the release of the respective cytokines directly by the PBMC at the site of antigen binding. The respective releases of cytokine measured in these experimental assays therefore correspond to the specific (targeted) action of the antibody that has been used and consequently do not constitute an undesirable side-effect (systemic release). The respective cytokines are then released only by the immune cells that are directly involved in the specific immune reaction.

FIG. 11 shows the results of the release of interleukin-10 (IL-10). In the case of IL-10 it is a question of an immunosuppressive cytokine. It is to be discerned that the release of IL-10 decreases in the case of stimulation with the antibody and administration of dexamethasone. This decrease is amplified with increasing concentration of dexamethasone.

FIG. 12 shows the results of the release of interleukin-6 (IL-6). The release of the pro-inflammatory cytokine IL-6 decreases in the case of stimulation with the antibody and administration of dexamethasone. This decrease is amplified with increasing concentration of dexamethasone. The release of IL-6 continues to decrease distinctly more intensely if no simultaneous contact with HCT8 is present. The absolutely higher release of the cytokine in the case of contact with HCT8 cells is not to be appraised here as a sign of a heightened side-effect (systemic release of cytokine), but is explained through the specific immunological action at the site of antigen binding. That is to say, without contact with the HCT8 cells (side-effect) the release of IL-6 decreases, in accordance with the invention, more rapidly than with contact with HCT8 cells (specific action). Expressed differently, there is a high specific action (release of the cytokine at the site of antigen binding).

FIG. 13 shows the results of the release of TNF-α. TNF-α is, like IFN-γ, a cytokine of the cellular immunity. The release of TNF-α decreases in the case of stimulation with the antibody and administration of dexamethasone. This decrease is amplified with increasing concentration of dexamethasone. Starting from a concentration of 0.1 µg/ml dexamethasone without simultaneous contact with HCT8 (systemic release; side-effect), the release of TNF-α decreases more intensely than in the case of contact with HCT8 (specific action). Here too, the absolutely higher release of TNF-α in the case of contact with HCT8 does not constitute a sign of a heightened side-effect (systemic release of cytokine), but is explained through the specific immunological action at the site of antigen binding, i.e. the side-effect decreases, in accordance with the invention, more intensely than the specific action.

Figure 14:
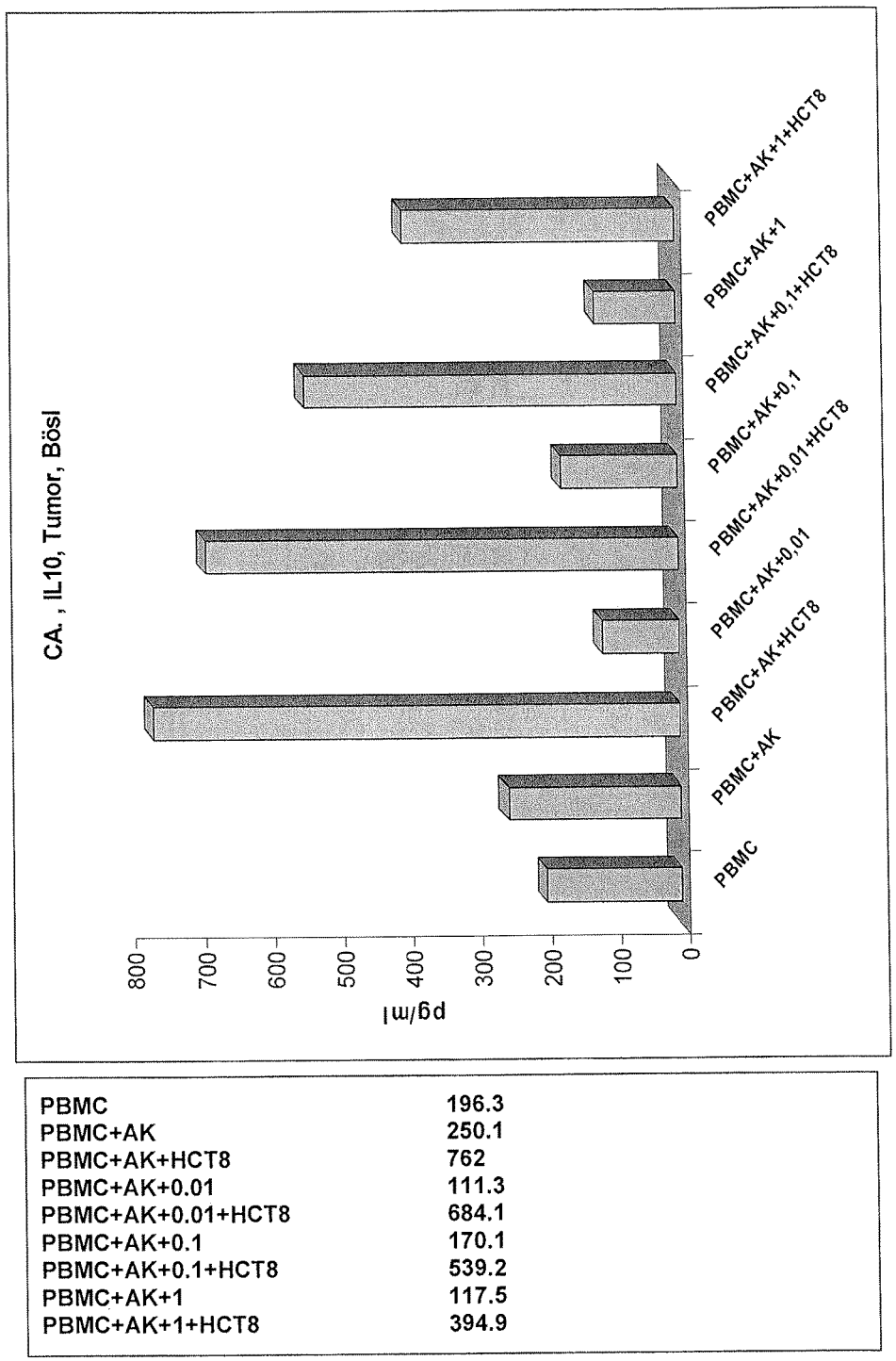
Figure 15:
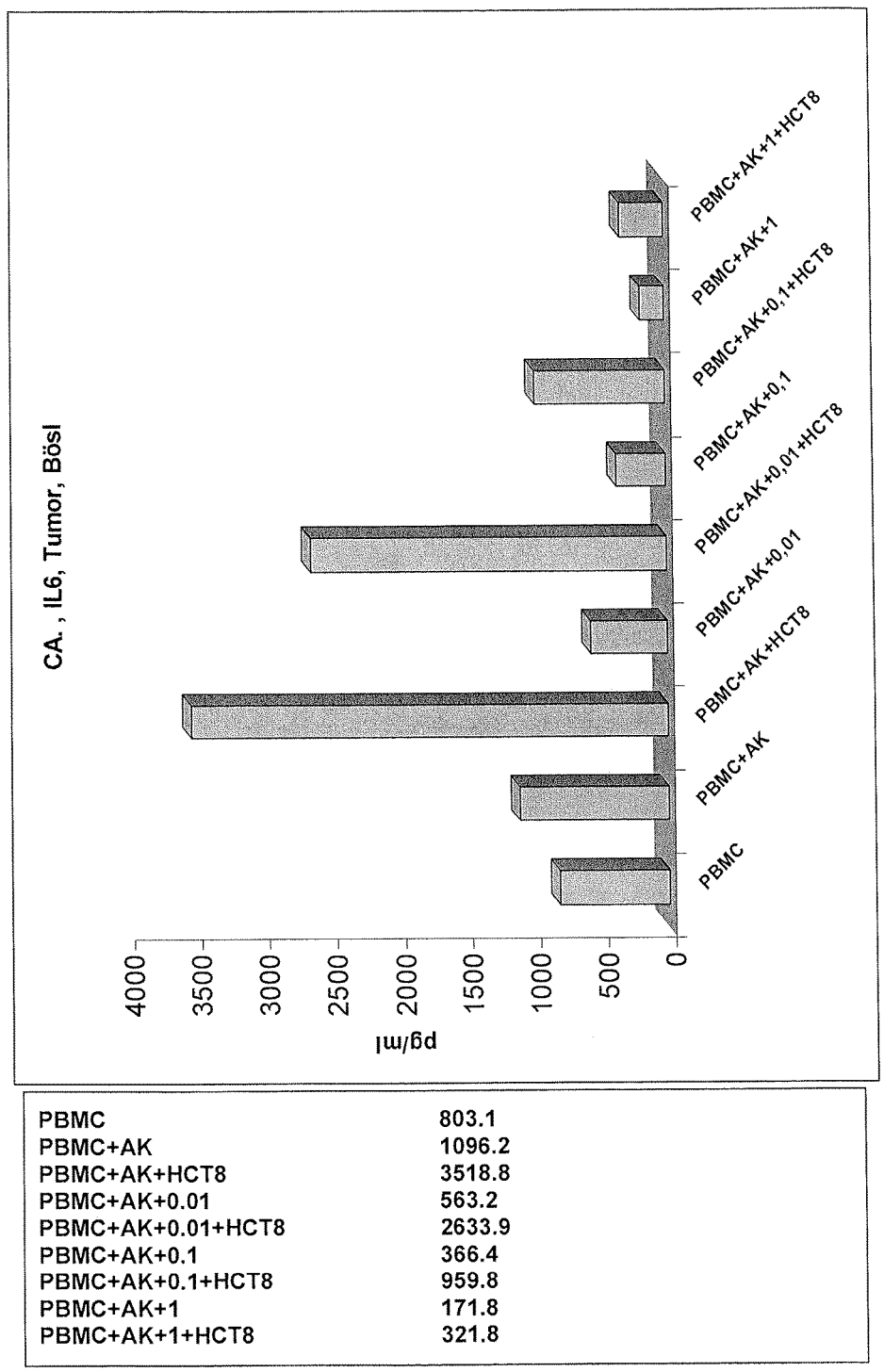
Figure 16:
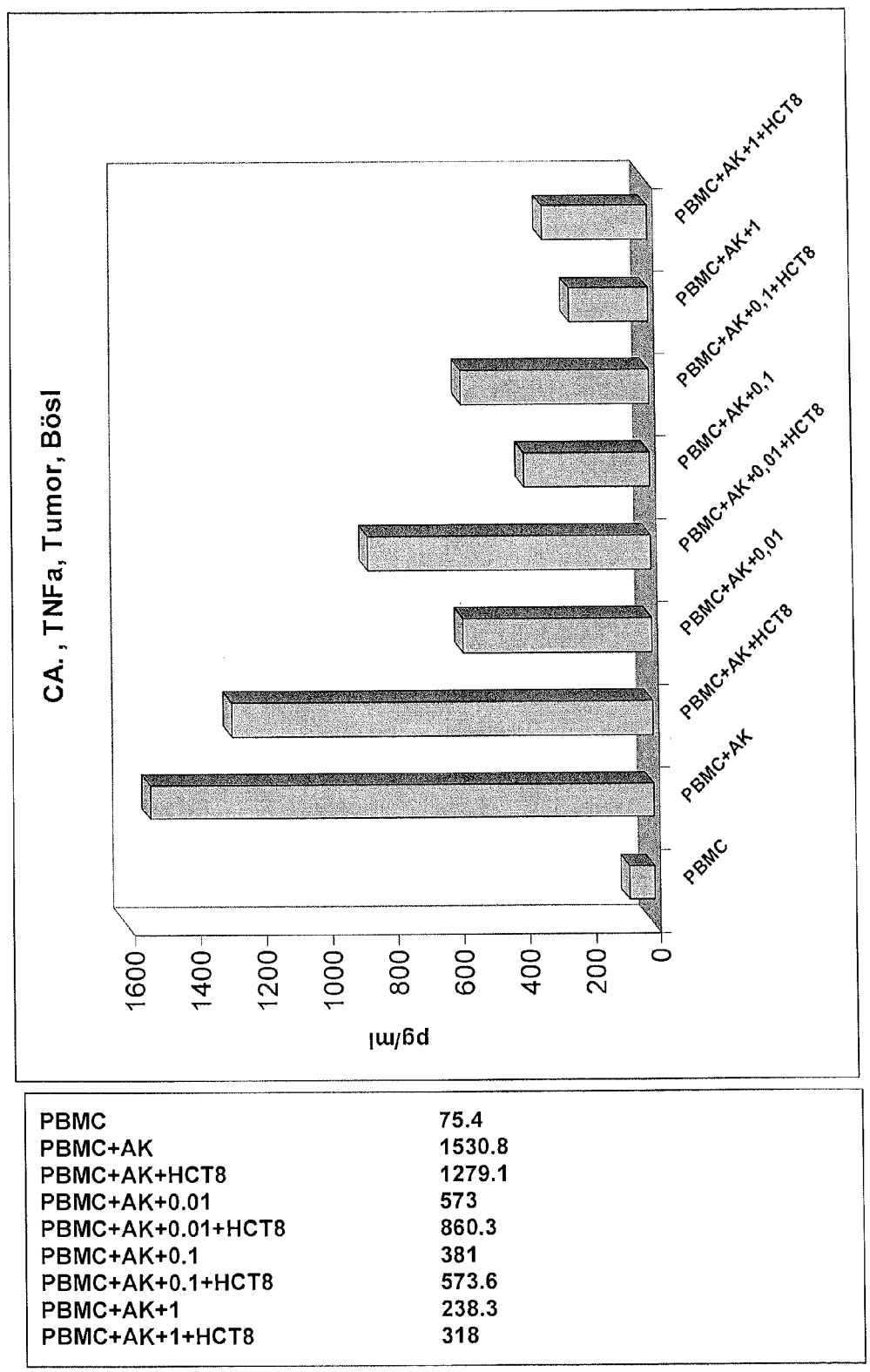

FIGS. 14 to 16 show graphic representations of the results of the release of various cytokines in tumour patients by PBMC. The experimental assays (concentrations, substances and cells used) correspond to those of the assays represented in FIGS. 11 to 13. The release of the same cytokines was measured likewise. By virtue of this, the results of the healthy test subjects (FIGS. 11 to 13) can be compared with those of the tumour patients (FIGS. 14 to 16). Likewise, the plotting on the y- and x-axes of the graphics corresponds to those of FIGS. 11 to 13. Here too, the stimulation of the PBMC without contact with HCT8 (according to FIGS. 1 to 3; 11 to 13) corresponds to the non-specific release of cytokine, which is independent of the antigen binding. The release of the respective cytokines is then effected systemically by the totality of the PBMC. The stimulation of the PBMC with contact with HCT8 corresponds to the release of the respective cytokines directly by the PBMC at the site of antigen binding. The respective releases of cytokine measured in the last-named experimental assays therefore correspond to the specific (targeted) action of the antibody that has been used and do not constitute an undesirable side-effect (systemic release). The respective cytokines are in this case only released from the immune cells that are directly involved in the specific immune reaction.

FIG. 14 shows the results of the release of interleukin-10 (IL-10). The release of IL-10 decreases in the case of stimulation with the antibody and administration of dexamethasone. This decrease is amplified with increasing concentration of dexamethasone. The release of IL-10 decreases more gently if there is no simultaneous contact with HCT8. The absolutely higher release of the cytokine in the case of contact with HCT8 cells is not to be appraised here as a sign of a heightened side-effect (systemic release of cytokine), but results from the specific immunological action at the site of antigen binding. That is to say, without contact with HCT8 (side-effect) the release of IL-10 decreases with increasing dexamethasone concentration, in accordance with the invention, more rapidly than with contact with HCT8 (specific action). That is to say, moreover, that, as desired, there is a very strong specific action (release of the cytokine at the site of antigen binding).

FIG. 15 shows the results of the release of interleukin-6 (IL-6). Here too, as in FIG. 14, the release of IL-6 decreases in the case of stimulation with the antibody and administration of dexamethasone, the decrease being amplified, here too, with increasing concentration of dexamethasone. The release of IL-6 decreases drastically more intensely if there is no simultaneous contact with HCT8. Here too, the absolutely higher release of the cytokine in the case of contact with HCT8 cells is not to be appraised as a sign of a heightened side-effect (systemic release of cytokine), but results from the specific immunological effect at the site of antigen binding. That is to say, without contact with HCT8 (side-effect) the release of IL-6 decreases, in accordance with the invention, with increasing dexamethasone concentration far more intensely than with contact with HCT8 (specific action). It accordingly remains to be noted that there is a very intense specific action (release of the cytokine at the site of antigen binding).

FIG. 16 shows the results of the release of TNF-α. In the case of stimulation with the antibody and administration of dexamethasone the release of TNF-α decreases, to be specific more intensely, the higher the concentration of dexamethasone. The release of TNF-α also decreases here, according to expectation, more intensely if there is no simultaneous contact with HCT8, in which connection, here too, the absolutely higher release of the cytokine in the case of contact with HCT8 is not to be appraised as a sign of a heightened side-effect (systemic release of cytokine), but results from the specific immunological action at the site of antigen binding. Without contact with HCT8 (side-effect) the release of TNF-α accordingly decreases with increasing dexamethasone concentration far more intensely than with contact with HCT8 (specific action). That is to say, there is a very intense specific action (release of the cytokine at the site of antigen binding).

Considering the results of the release of cytokine in the case where use is made of the trifunctionally bispecific antibody anti-EpCAM x anti-CD3, on the one hand in healthy test subjects (FIGS. 11 to 13), on the other hand in tumour patients (FIGS. 14 to 16), it remains to note in accordance with the invention that the results achieved in the case of the tumour patients correspond to those in the case of the healthy test subjects, in which connection in the case of the tumour patients the glucocorticoid dexamethasone takes effect, in accordance with the invention, more intensely on the non-specific systemic release of cytokine (side-effects; without contact with HTC8) than on the specific action (against EpCAM and CD-3), as a result of which the side-effects are greatly reduced in accordance with the invention.

Figure 17:
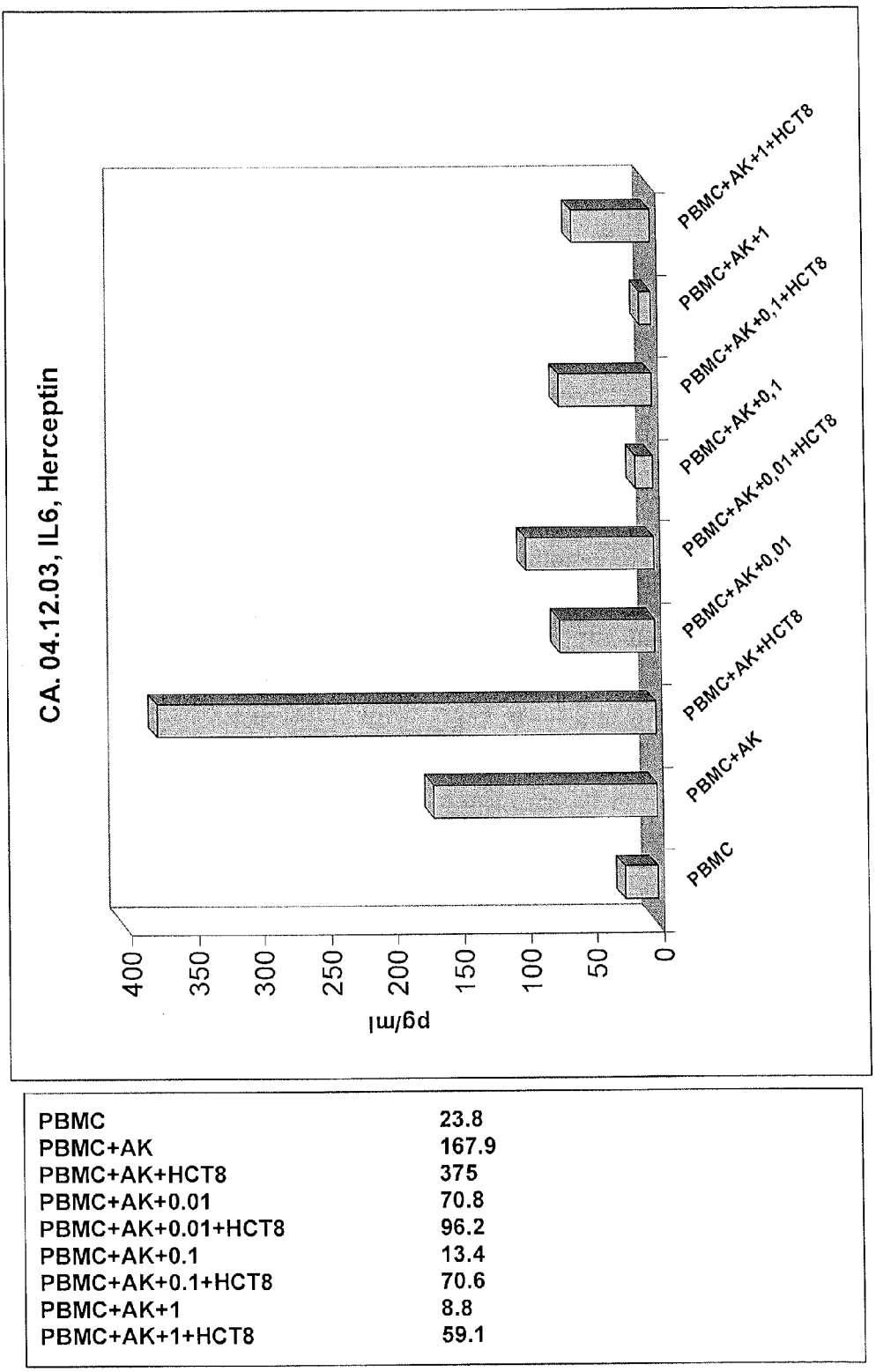
Figure 18:
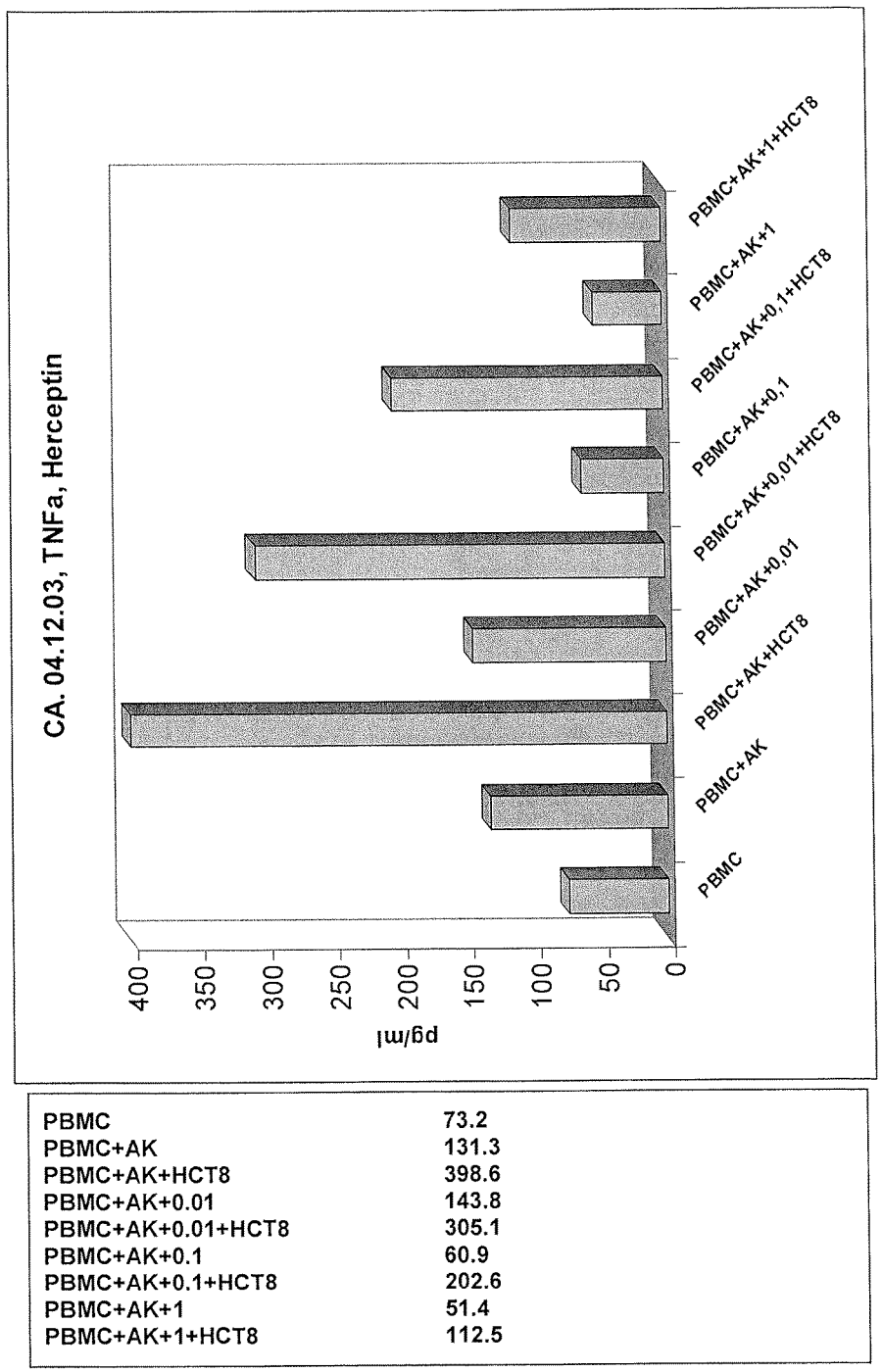

FIGS. 17 to 18 show graphic representations of the results of the release of various cytokines in healthy test subjects by PBMC (at a concentration of $10^6$ cells/ml) after stimulation with the monoclonal monospecific antibody Herceptin (AK) (at a concentration of 1 mg/ml) without and in the presence of HER2/neu-positive tumour cells (HCT8) (at a concentration of 5×10⁴ cells/ml). On the y-axes the concentration of the respective cytokine in pg/ml has been plotted. On the x-axes the respective stimulation assays of the PBMC have been plotted. The respective concentration of the added dexamethasone in μg/ml is specified by "0.01", "0.1" and "1". The values of unstimulated PBMC by way of control have likewise been plotted ("PBMC").

FIG. 17 shows the results of the release of interleukin-6 (IL-6). In the case of stimulation of the PBMC with the antibody and administration of dexamethasone the release of IL-6 decreases, the decrease being amplified with increasing concentration of dexamethasone. The release of IL-6 decreases far more intensely if there is no simultaneous contact with HCT8. The absolutely higher release of the cytokine in the case of contact with HCT8 cells is not a sign of a heightened side-effect (systemic release of cytokine), but arises from the specific immunological action at the site of antigen binding. Without contact with HCT8 (side-effect), the release of IL-6 decreases with increasing dexamethasone concentration more intensely than with contact with HCT8 (specific action). There is a strong specific action (release of the cytokine at the site of antigen binding).

FIG. 18 shows the results of the release of TNF-α. In the case of stimulation with the antibody and administration of dexamethasone the release of TNF-α decreases. The decreases occurs more intensely, the higher the concentration of dexamethasone. The release of TNF-α decreases drastically more intensely if there is no simultaneous contact with HCT8, in which connection, here too, the absolutely higher release of the cytokine in the case of contact with HCT8 is not a sign of heightened side-effect (systemic release of cytokine), but arises from the specific immunological action at the site of antigen binding. Without contact with HCT8 (side-effect) the release of TNF-α accordingly decreases significantly more intensely with rising dexamethasone concentration than with contact with HCT8 (specific action). That is to say, there is a very strong specific action (release of the cytokine at the site of antigen binding).

In considering the results of the release of diverse cytokines in the case of stimulation of PBMC with various antibodies
  (i) experimental assays of FIGS. 11 to 16: stimulation with the trifunctionally bispecific antibody anti-EpCAM x anti-CD3;
  (ii) experimental assays of FIGS. 17 to 18: stimulation with the monospecifically monoclonal antibody Herceptin
it remains to be noted that both antibodies, despite their different active mechanisms, showed substantially the same effects on the release of various cytokines, both in healthy test subjects and in tumour patients.

Figure 19:
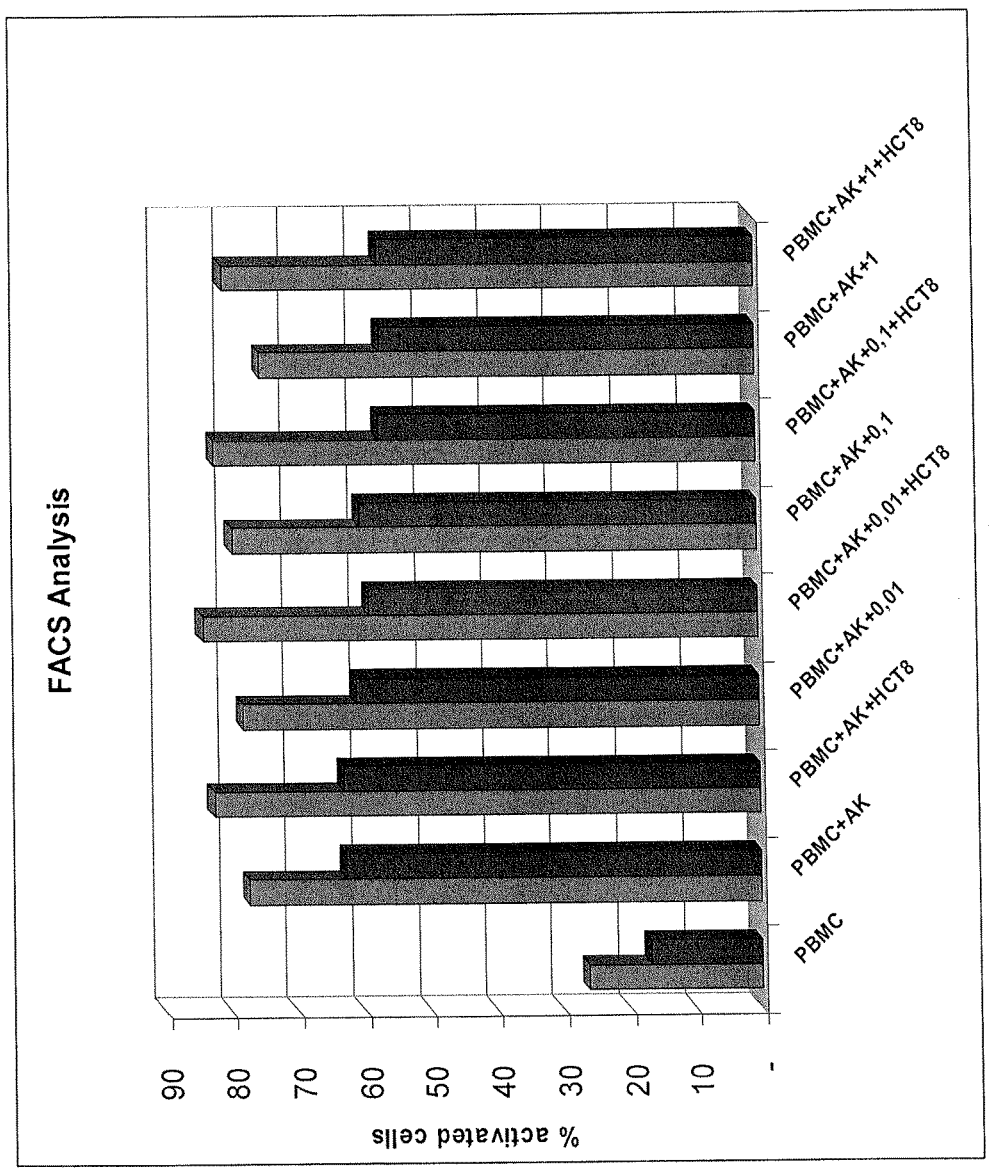

FIG. 19 shows graphic representations of the results of measurements relating to T-cell activation by the trifunctional bispecific antibody with the specificity anti-EpCAM x anti-CD3 at a concentration of 10⁶ cells/ml under the influence of the simultaneous administration of dexamethasone (concentrations of 0.01, 0.1 and 1 μg/ml). The measurement of the surface markers CD3/CD4/CD25 and CD3/CD8/HLADR on T helper cells has been represented. In this regard, CD3/CD4 represent T helper lymphocytes, in which connection CD25 is an activation marker of these cells. CD3/CD8 represent cytotoxic T-lymphocytes, in which connection HLADR is an activation marker of these cells. On the y-axis the percentage fraction of the CD3/CD4 (T helper cells) and CD3/CD8 (T killer cells)-positive T-lymphocytes with expression of the activation markers (CD25 and HLADR) has been plotted. On the x-axis the respective PBMC stimulation assays have been plotted with and without contact with HCT8 target cells (concentration 5×10⁴ cells/ml) and also with and without administration of dexamethasone in various concentrations, the respectively left-hand column relating to the CD3/CD4/CD25 measurement, and the respectively right-hand column relating to the CD3/CD8/HLADR measurement. The measurements were undertaken by means of FACS analysis. In the table underneath FIG. 19 the measured values (in percent) of the respective stimulation assays have been specified. It is to be discerned that dexamethasone does not influence the T-cell activation in the case of stimulation with the trifunctional bispecific antibody subject to contact with the HCT8 target cells (this stimulation corresponds to the specific stimulation with binding of the target antigen). This is substantiated by the unchanged high measured values in the table underneath FIG. 19.

EXAMPLES

The examples, which are intended to be purely exemplary of the invention and should therefore not be considered to limit the invention in any way, also describe and detail aspects and embodiments of the invention discussed above. The examples are not intended to represent that the experiments below are all or the only experiments performed. Efforts have been made to ensure accuracy with respect to numbers used (e.g., amounts, temperature, etc.) but some experimental errors and deviations should be accounted for. Unless indicate otherwise, parts are parts by weight, molecular weight is average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications can be made to adapt a particular situation, material, composition of matter, process, process step or steps, to the objective, spirit and scope of the present invention. All such modifications are intended to be within the scope of the claims appended hereto.

The following examples elucidate the present invention further without restricting it.

Example 1

Extraction of PBMC

Mononuclear cells were extracted from the peripheral blood of a healthy volunteer by means of centrifugation over Ficoll (density 1.068 g/cm³). To this end, venous heparinised blood was stratified over Ficoll and centrifuged at 2000 rpm for 20 min. The cell layer located above the Ficoll was pipetted off after centrifugation and was washed with PBS.

Stimulation of PBMC

For the purpose of stimulation, the PBMC were used at a concentration of 1×10⁶/ml. The stimulation of the PBMC was effected with an intact trifunctional bispecific antibody either of the specificity anti-EpCAM x anti-CD3 at a concentration of 100 μg/ml or of the specificity anti-HER2/neu x anti-CD3 at a concentration of 1 mg/ml. The stimulation was carried out for 24 h by incubation at 37° C. The stimulation was effected in each instance without tumour cells or in the presence of 5×10⁴ HCT8 tumour cells (relative to ATCC; EpCAM-positive) per ml. With respect to the effect of the synthetic glucocorticoid dexamethasone (from Jenapharm®), stimulation assays without glucocorticoid and also assays with 0.01, 0.1, 1 and 10 µg/ml were carried out.

Determination of Cytokines

After the stimulation the determination of the concentrations of the cytokines IL-6, IL-10, TNF-α and IFN-γ was undertaken in the supernatant on plates with 24 recesses in each instance by means of an ELISA. In each instance duplicate measurements were carried out. The ELISAs were undertaken by means of standardised kits produced by R&D Systems, in accordance with the manufacturer's instructions.

Results

Release of IL-6

IL-6 is a cytokine which is secreted by immunological effector cells and antigen-presenting cells directly upon occurrence of an immunological reaction. The clinical significance of IL-6 as cytokine in the serum is due to the fact that a few hours after occurrence of an inflammation or an immune reaction IL-6 is secreted and the quantity thereof correlates with the extent of the immune reaction. In the present example, in the case of contact with EpCAM-positive tumour cells (HCT8) with simultaneous addition of 0.01 µg/ml to 10 µg/ml dexamethasone a release of IL-6 with values above 5000 pg/ml in the supernatant (FIG. 1B) becomes evident. This release corresponds to the immunological action of the EpCAM-specific antibody and therefore represents the desired immunological action. This intense release of IL-6 is effected by only a few immune cells that are directly involved in the reaction, which is dependent on the specific antigen/antibody interaction.

In contrast thereto, in the case of a stimulation of the PBMC with antibodies without contact with HCT8 tumour cells a release of IL-6 of over 9000 pg/ml (FIG. 1A) becomes evident. This release arises in the case of clinical application of the immunstimulatory antibody systemically by many PBMC independently of the desired specific action. By virtue of the systemic release of IL-6, a very large quantity of IL-6 is therefore generated in the body, which is ultimately responsible for the severe side-effects, extending as far as an SIRS.

By combination of the antibody with a glucocorticoid (in the present case, dexamethasone) it was established in accordance with the invention that the non-specific release of IL-6, which is substantially responsible for the clinical side-effects of immunostimulating antibodies, is completely reduced by dexamethasone. At the same time, however, the release of IL-6, which is indicated after stimulation with EpCAM-positive tumour cells and consequently corresponds to the desired specific action of the immunostimulatory antibody, is maintained.

Release of TNF-α

Figure 2A:
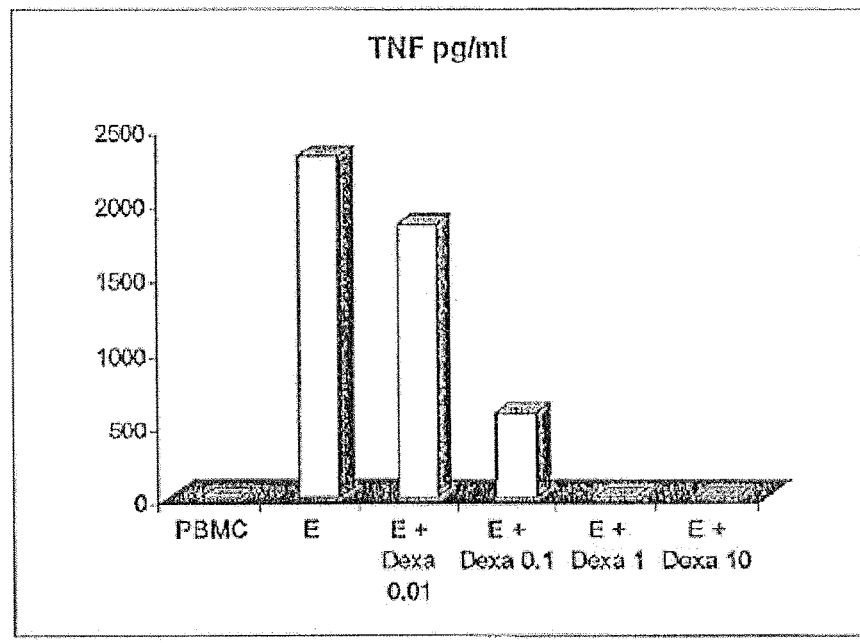
FIG. 2A-2C represents in diagrams the results of the release of tumour necrosis factor α (TNF-α) after stimulation with trifunctional bispecific antibody of the specificity anti-EpCAM x anti-CD3 without and in the presence of EpCAM-positive tumour cells.
Figure 2B:
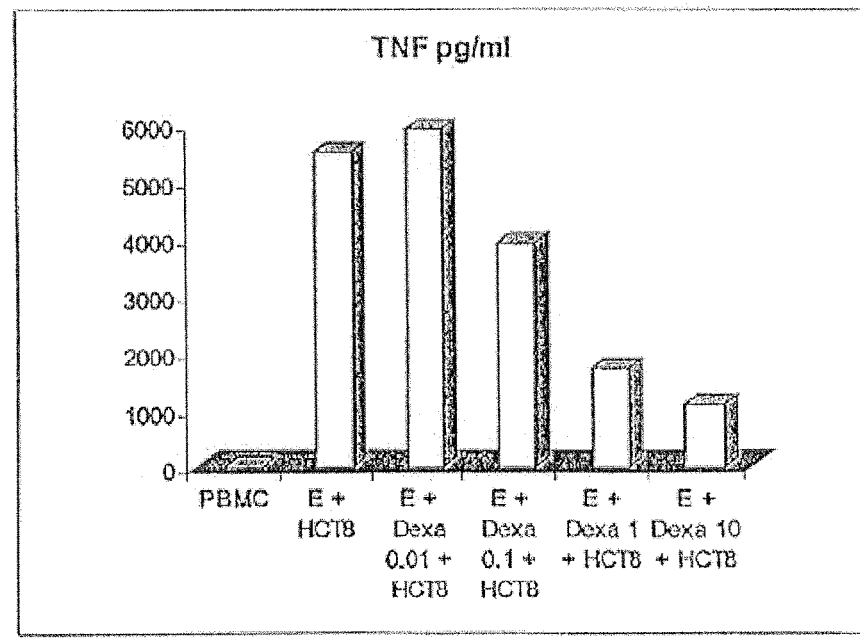
Figure 2C:
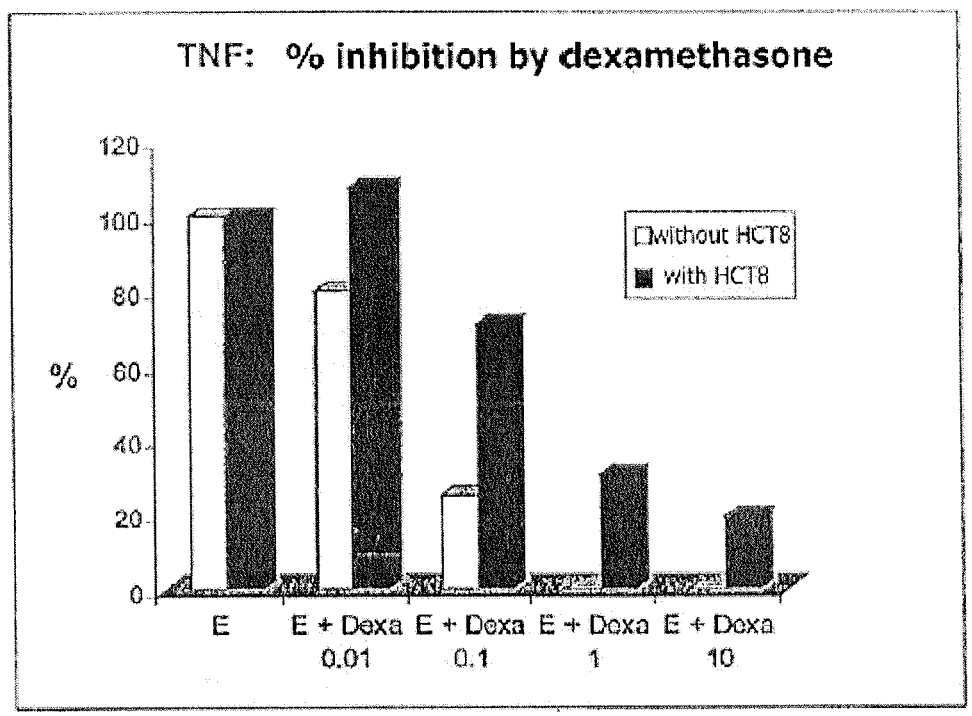

TNF-α is a TH1 cytokine which is secreted by immunological effector cells (here: PBMC) in the case of immunological destruction of target cells (here: HCT8 tumour cells). In comparison with a non-specific stimulation without tumour cells, in the present example roughly triply increased values of TNF-α were measured after stimulation with the trifunctional bispecific antibody in the presence of target cells with defined antigen (EpCAM) (FIGS. 2A and 2B). This distinct increase in the TNF-α concentration arises from the target-cell-dependent release by the PBMC in the course of the tumour-cell destruction. If the trifunctional bispecific antibody is combined, in accordance with the invention, with a glucocorticoid—in the present case, dexamethasone—the release of TNF-α that is based on non-specific effects is reduced or, in the case of correspondingly high glucocorticoid concentration, completely reduced. Consequently, through the use, according to the invention, of glucocorticoids the clinical side-effects that are based on a non-specific release of TNF-α can be significantly reduced or eliminated. In contrast to the non-specific release of cytokine, in the case of addition of dexamethasone the antigen-dependent and hence target-cell-specific release of TNF-α is fully maintained.

Release of IFN-γ

Figure 3A:
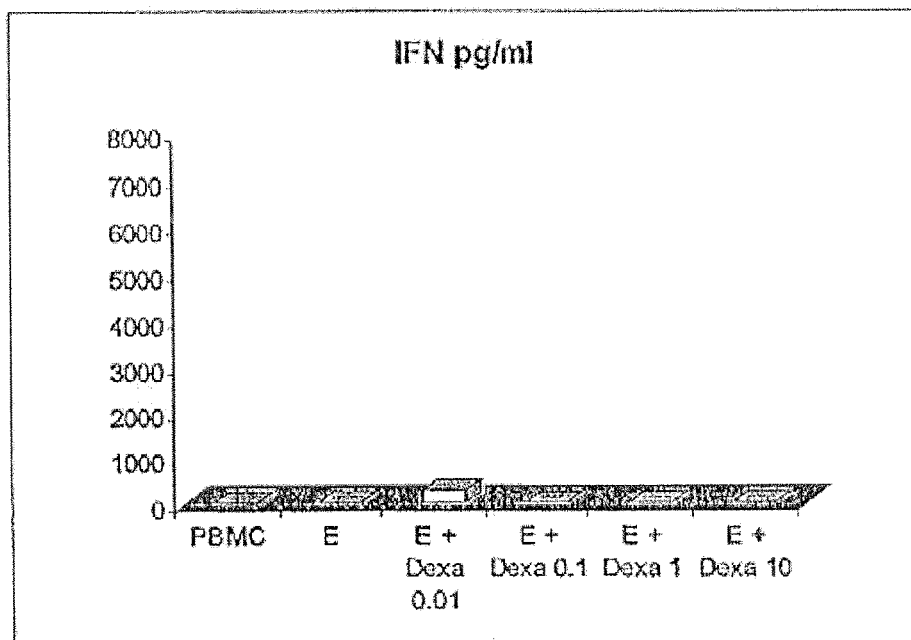
FIG. 3A-3C shows, in further diagrams corresponding to the representations of FIGS. 1A-1C and 2A-2C described above, results relating to the release of interferon-γ (IFN-γ) from PBMC after the stimulation thereof with bispecific antibody (anti-EpCAM x anti-CD3) without and with contact with target cells (EpCAM-positive tumour cells). IFN-γ is (like TNF-α) a TH1-specific (T-helper-cell-type-1-specific) cytokine and furthermore a marker for the T-cell-mediated antigen-specific target-cell destruction. IFN-γ is secreted by activated specific T-lymphocytes after stimulation against an antigen. Therefore IFN-γ should not arise in the case of a stimulation with antibody without simultaneous contact with the target cells, since in this case no stimulation is effected on the basis of a target-antigen/antibody interaction.
Figure 3B:
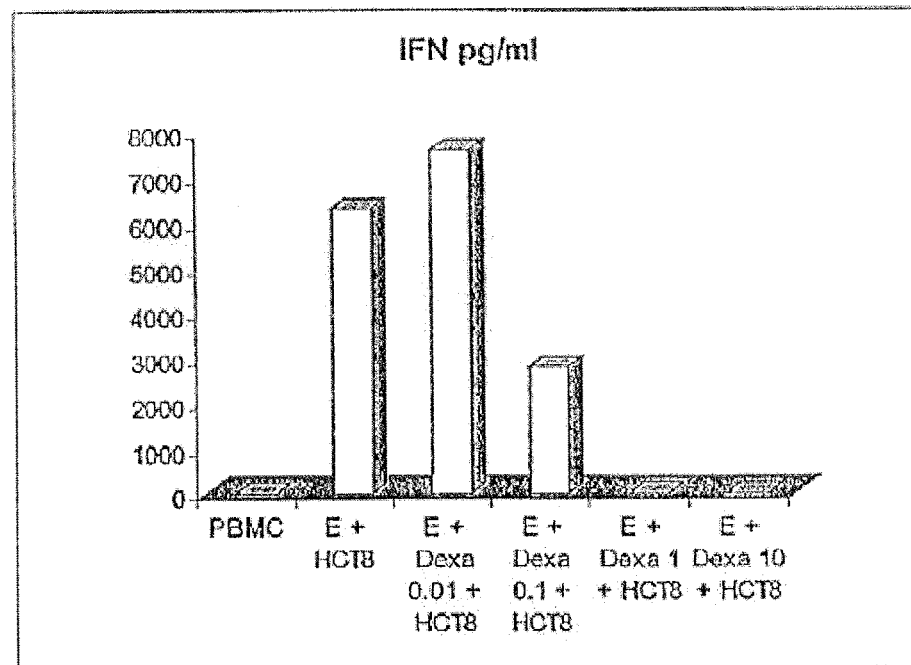
Figure 3C:
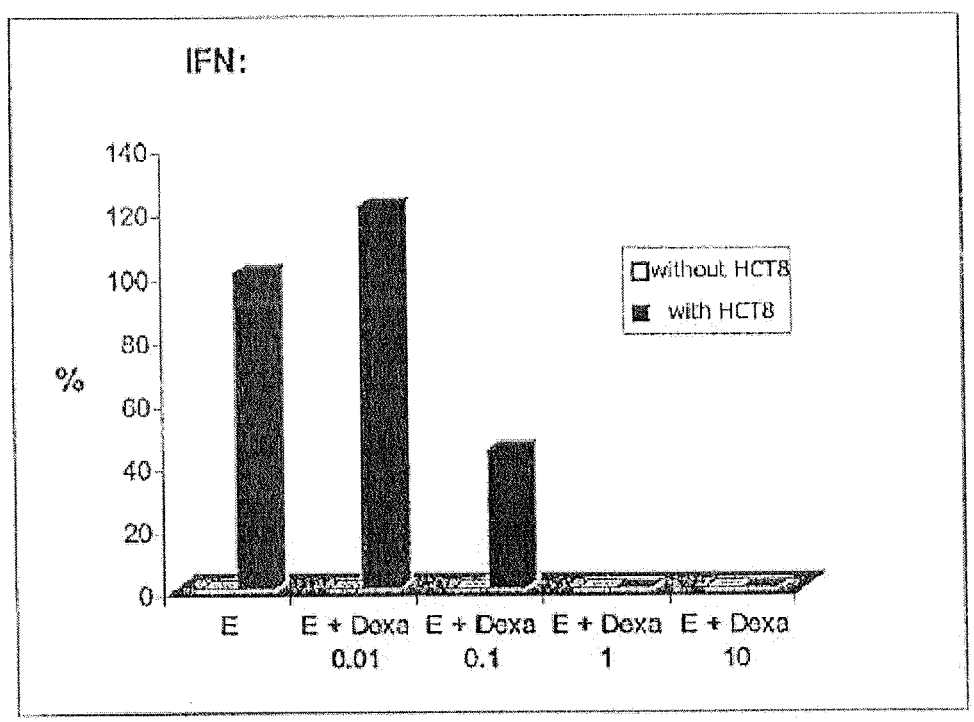
Figure 4A:
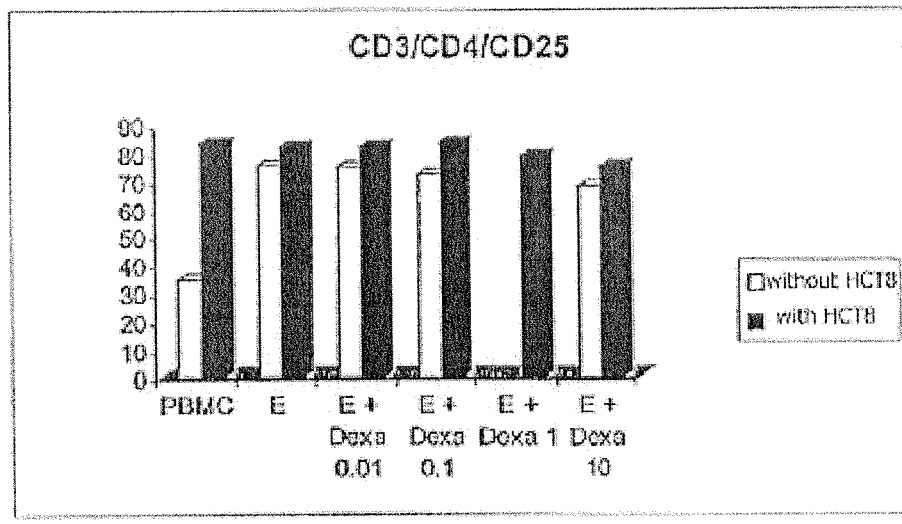
FIG. 4A-4E shows graphic representations of the results of experiments relating to the T-cell activation by the trifunctional bispecific antibody with the specificity anti-EpCAM x anti-CD3 (concentration of $10^6$ cells/ml) under the influence of the simultaneous administration of dexamethasone (concentrations of 0.01, 0.1, 1 and 10 µg/ml).
Figure 4B:
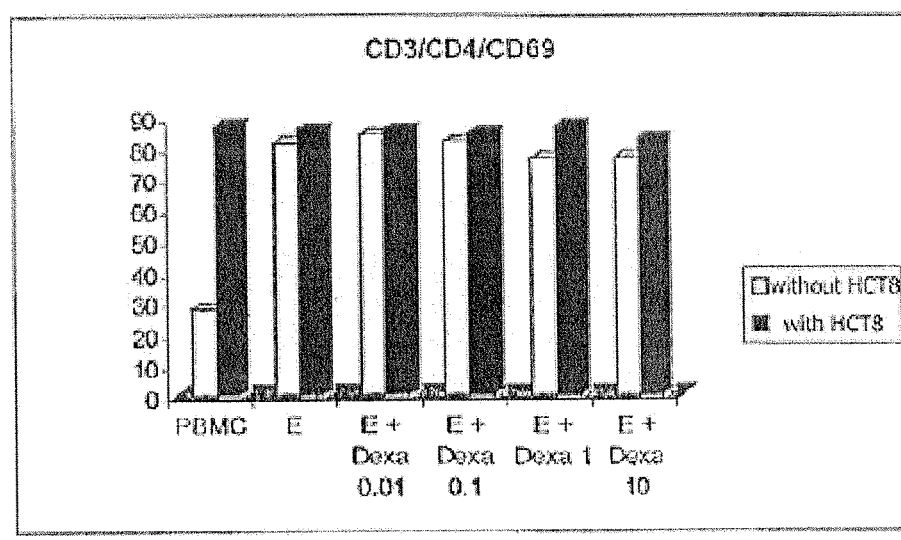
Figure 4C:
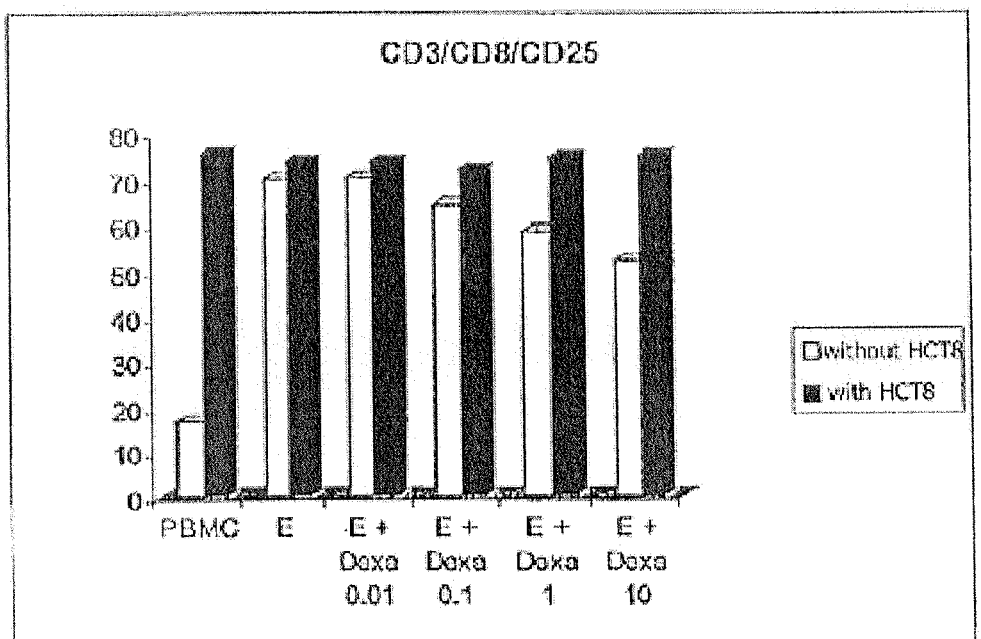
Figure 4D:
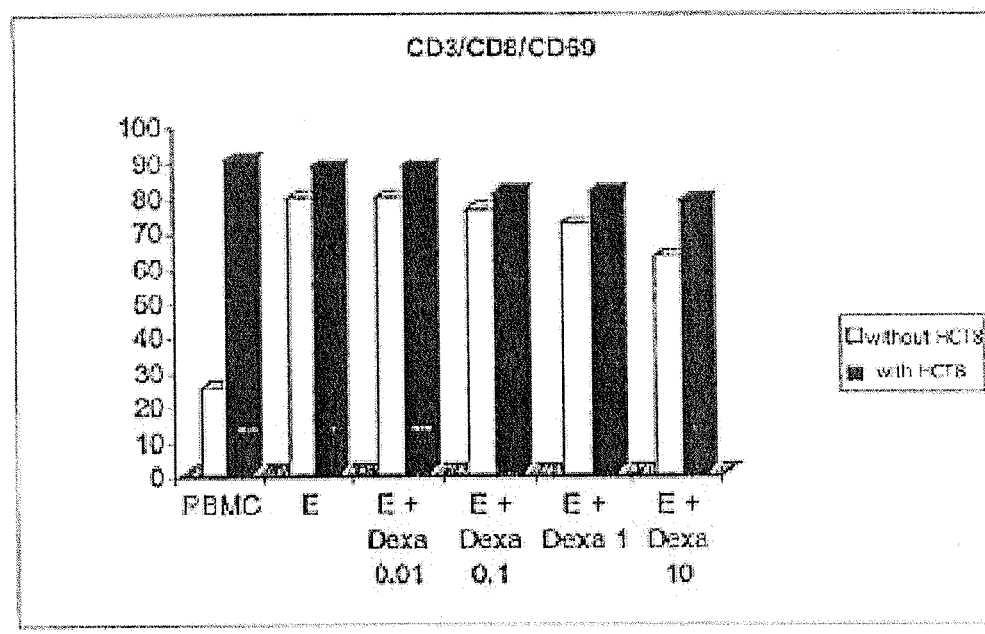
Figure 4E:
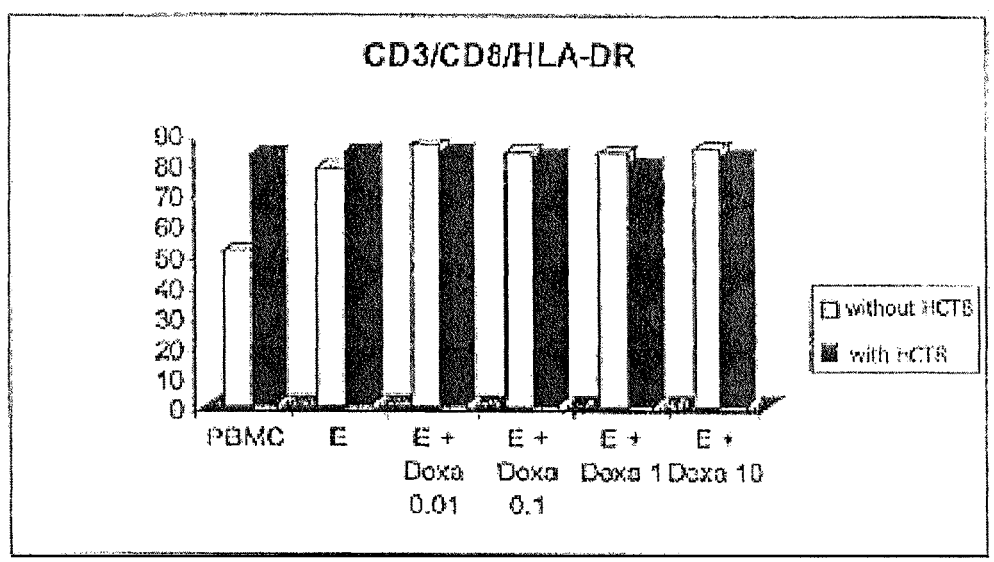

IFN-γ is likewise a TH1 cytokine. Furthermore, IFN-γ is secreted by activated specific T-lymphocytes after stimulation against an antigen, on account of which IFN-γ is a marker for the T-cell-mediated antigen-specific target-cell destruction. Therefore IFN-γ is not secreted after a stimulation of the PBMC with the trifunctional bispecific antibody in the absence of HCT8 target cells, since in this case only a non-specific stimulation occurs, which is not directed against an antigen (FIG. 3A). In the course of the stimulation in the presence of HCT8 cells a significant release of IFN-γ, which is caused by the stimulation against EpCAM by the antibody, was measured (FIG. 3B). In the case of glucocorticoid concentrations in the present example of below 1 µg/ml this target-cell-specific release of IFN-γ is substantially maintained.

Example 2

In order to determine the influence of glucocorticoid on the T-cell activation by means of stimulation with the trifunctional bispecific antibody anti-EpCAM x anti-CD3, stimulation experiments as specified in the above Example 1 were carried out, and the T-cell-specific activation markers CD25, CD69 and HLA-DR in the case of $CD3^+/CD4^+$ and $CD3^+/CD8^+$ T-lymphocytes were then measured.

FACS Analysis

Implementation of the FACS analyses was effected using a FACSCalibur manufactured by Becton Dickinson. Appropriately stimulated PBMC with FITC-marked, PE-marked and APC-marked antibodies of the requisite specificity were marked.

Results

As is evident from FIGS. 4A to 4E, in the case of a stimulation with the bispecific, trifunctional antibody no influencing of the T-cell activation by the glucocorticoid dexamethasone was established.

Example 3

With the aid of a cytotoxicity test the influence of glucocorticoid on the T-cell toxicity was investigated. The extraction of the PBMC and the stimulation thereof were carried out in accordance with the above Example 1.

Cytotoxicity Test

The measurement of cytotoxicity was undertaken with the aid of a fluorescence test using the dyestuff BCECF-AM. The measurement was undertaken by means of 2 h release technology corresponding to the procedure in Kolber et al. (1988) J. Immunol. Meth. 108: 255-264.

Results

Figure 5A:
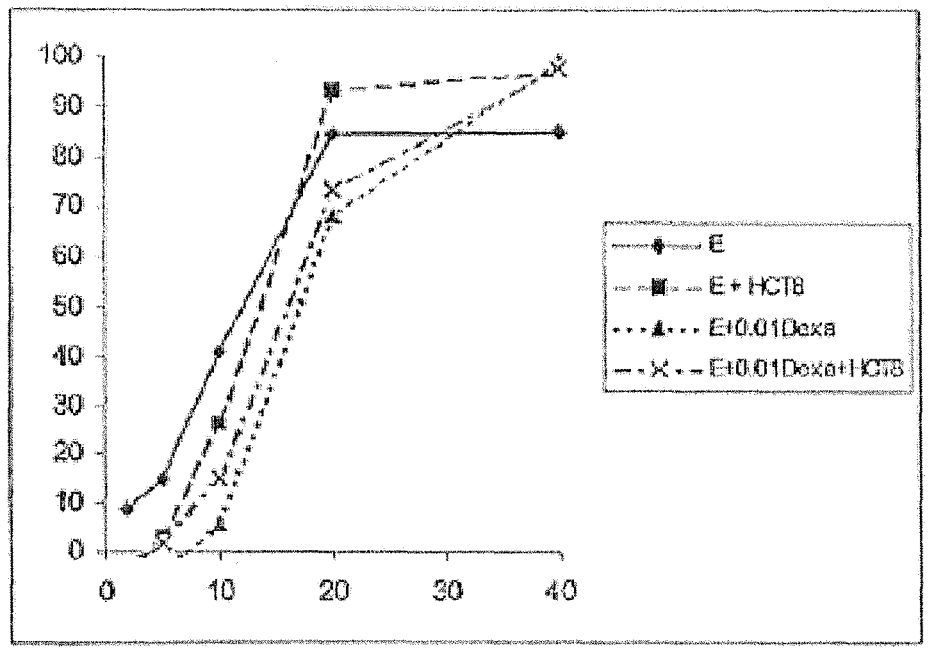
FIG. 5A-5D represents in diagrams the results of the measurement of the specific percentage cytotoxicity, which was determined in a two-hour cytotoxicity assay with fluorescence-marked HCT8 tumour cells.
Figure 5B:
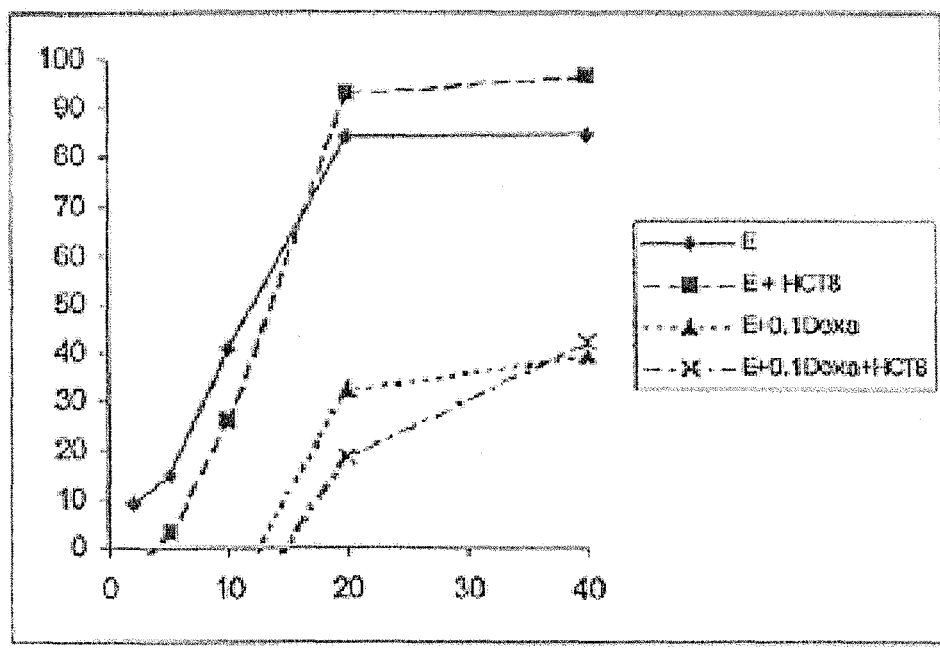
Figure 5C:
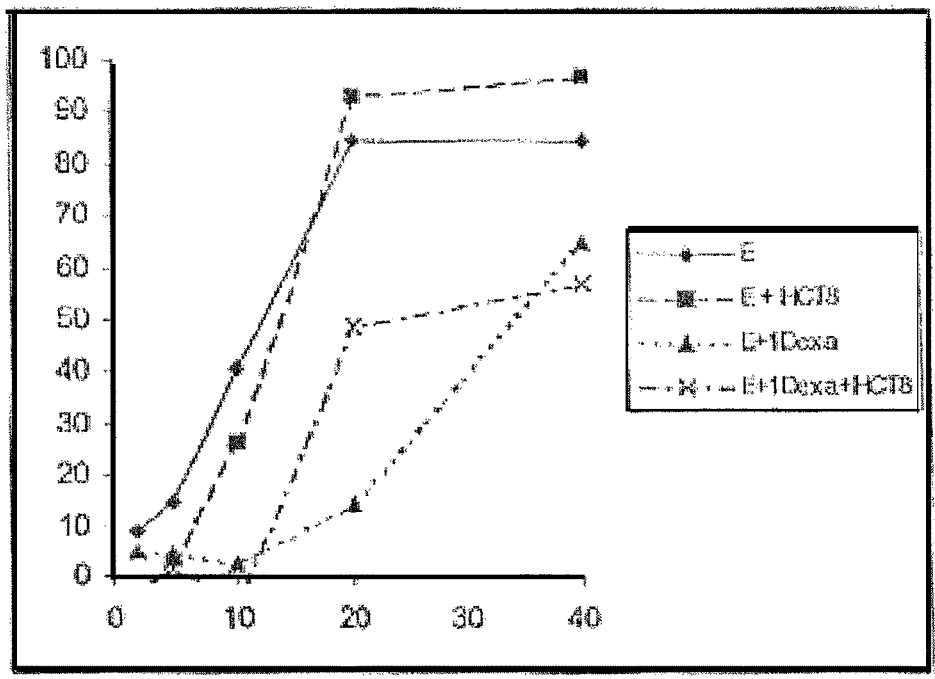
Figure 5D:
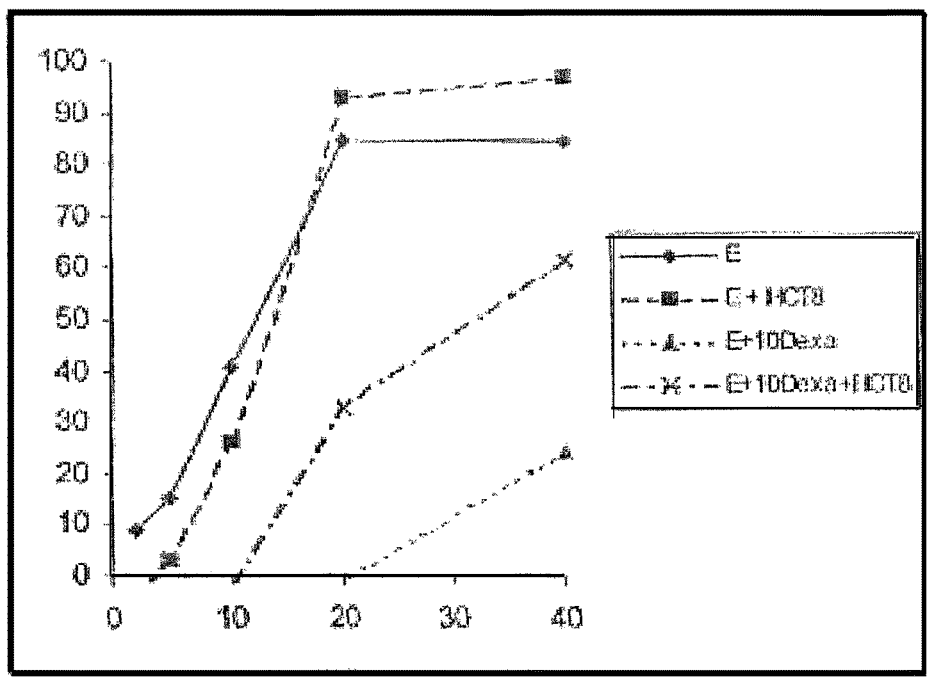

As is evident from FIGS. 5A to 5B, the effect of dexamethasone on the cytotoxicity of stimulated PBMC, caused by the trifunctional, bispecific antibody, can be summarised as follows: At a concentration of 0.01 mg/ml no effect of dexamethasone on the cytotoxicity of the stimulated PBMC was observed. Starting from a concentration of 0.1 µg/ml, a significant reducing of the cytotoxicity was observed, irrespective of whether HCT8 tumour cells were present or not during the stimulation. In the case of a stimulation in the presence of HCT8 the percentage cytotoxicity was maintained constant at a high level if use was made of a ratio of the effector cells to target cells of 40:1 and concentrations from 0.1 µg/ml to 10 µg/ml dexamethasone. If no target cells are present during the stimulation of the PBMC, the percentage cytotoxicity declines further as a function of the dexamethasone concentration.

The in vitro data according to Examples 1 to 3 can therefore be summarised as follows. Through the combination of immunostimulating antibodies with glucocorticoids a reducing of the non-specific release of cytokine occurs, without the desired antigen-specific immune reaction (Example 1), T-cell activation (Example 2) or the cytotoxicity of the stimulated cells (Example 3) being reduced to the same extent. Between a concentration of 0.1 µg/ml and 1 µg/ml dexamethasone the non-specific reaction is greatly reduced or completely eliminated. In contrast thereto, within this glucocorticoid-concentration range in vitro the specific immune activity directed against the tumour-cell antigen EpCAM was not influenced significantly.

Example 4

A patient (46 years old, male) with a gastric carcinoma (peritoneal carcinosis; pT3 pN2 M1) was subjected to immunotherapy using, in accordance with the invention, a glucocorticoid with the trifunctional, bispecific antibody of the specificity anti-EpCAM x anti-CD3. The therapy was undertaken after gastrectomy in 2000 and after multiple ineffective chemotherapy of the tumour. The patient exhibited a symptomatic production of ascites. The testing of the tumour cells in the ascites yielded a strong EpCAM expression (EpCAM+++). The administration of the antibody was effected intraperitoneally (i.p.), in each instance by infusion over 6 h to 10 h.

At the start of the therapy the antibody was administered to the patient in relatively small dose without combination with glucocorticoid. After these two monotherapy experiments the antibody dose was distinctly increased, and at the same time dexamethasone was given. In the following table the course of therapy is summarised, with indication of the side-effects observed.

TABLE 1

Course of therapy in patient with gastric carcinoma

| Day | Therapy | Clinical Progress |
|---|---|---|
| 0 | 10 E | Infusion over 6 h, 1000 ml Tuto ip |
|  |  | Premedication 2A Fenistil + 1000 mg Benuron |
|  |  | Fever to 39.3 |
|  |  | Vomiting |
|  |  | Tummy-aches, administration of Tramal |
|  |  | Exhaustion |
| 1 |  | Persistence of fever to 39.0 |
| 2 |  |  |
| 3 |  | Fever 39.0 → Novalgin 1A 19.15 |
| 4 | 30 E | Infusion over 8 h, 1000 ml Tuto ip |
|  |  | Premedication 2A Fenistil + 1000 mg Benuron |
|  |  | Termination of therapy if fever > 39.6 after 6 h |
|  |  | Novalgin 1A |
|  |  | Shivering |
|  |  | Nausea |
| 5 |  | Persistence of fever: |
|  |  | Novalgin 1A |

TABLE 1-continued

Course of therapy in patient with gastric carcinoma

| Day | Therapy | Clinical Progress |
|---|---|---|
|  |  | Novalgin 30 ggt |
|  |  | Exhaustion |
| 6 |  |  |
| 7 |  |  |
| 8 |  | Change of catheter |
|  |  | Fresh ascites quantity: 500 ml |
| 9 | 100 E | Changed premedication |
|  |  | 2A Fenistil |
|  |  | 2A Tagamet |
|  |  | 40 mg dexamethasone |
|  |  | 1000 ml Tuto ip |
|  |  | Infusion over 8 h |
|  |  | Fever up to maximum 39.0 |
| 10 |  |  |
| 11 |  |  |
| 12 |  | Strong allergic reaction with complete erythema on trunk |
| 13 |  |  |
| 14 |  |  |
| 15 | 100 E | 2A Fenistil |
|  |  | 2A Tagamet |
|  |  | 10 mg dexamethasone |
|  |  | 1000 ml Tuto ip |
|  |  | Infusion over 8 h |
|  |  | No fever |
|  |  | No SE |
| 16 |  |  |
| 17 |  |  |
| 18 |  |  |
| 19 | 200 E | 2A Fenistil |
|  |  | 2A Tagamet |
|  |  | 10 mg dexamethasone |
|  |  | 1000 ml Tuto ip |
|  |  | Infusion over 10 h |
|  |  | No fever |
|  |  | No SE |
| 20 |  |  |
| 21 |  |  |
| 22 |  |  |
| 23 | 500 E | 2A Fenistil |
|  |  | 2A Tagamet |
|  |  | 10 mg dexamethasone |
|  |  | 1000 ml Tuto ip |
|  |  | Infusion over 8 h |
|  |  | No fever |
|  |  | No SE |

E: µg i.p. trifunctional bispecific antibody anti-EpCAM x anti-CD3
SE: side-effects As is evident from Table 1, in the course of monotherapy with the immunostimulatory antibody in the case of a dose from 10 mg to 30 mg the patient suffered from strong side-effects, in particular vomiting, tummy-aches, malaise and also high fever. However, if the antibody was combined with dexamethasone the dosage of antibody was able to be increased to 500 mg i.p. without fever or other side-effects arising. The immunological laboratory parameters confirmed the strong immunostimulatory action of the antibody, which was specifically directed against the tumour cells (FIG. 6). Hepatic values and pancreatic values were largely unremarkable under the combined therapy according to the invention (FIG. 7). After conclusion of the therapy according to the invention a complete disappearance of malignant ascites was noted, and also, in the course of therapy, a complete elimination of the malignant tumour cells in the ascites.

Example 5

In a further example according to the invention a female patient (68 years) with an adenocarcinoma (Sigma pT3 pN2

M1) and with diffuse hepatic metastasis was subjected to immunotherapy with the trifunctional bispecific antibody anti-EpCAM x anti-CD3 in combination with the glucocorticoid dexamethasone. It was previously established that the cells of the hepatic metastases were 80% EpCAM-positive. In the course of the present therapy the application of the antibody was undertaken via a selective catheter via the A. hepatica dextra as an example of a selective administration into an organ (in the present case, intrahepatically) or systemically (after perfusion of the liver). The administration of dexamethasone was undertaken in each instance by way of premedication prior to the administration of the immunstimulatory antibody.

The therapy and the course thereof are specified in the following Table 2.

TABLE 2

Course of therapy in female patient with adenocarcinoma and diffuse hepatic metastasis

| Day | Therapy | Remark |
| --- | --- | --- |
| 0 | 1 μg | Application via selective arterial port into A. hepatica dextra over 8 h<br>Premedication: dexa 40 mg, 2A Fenistil, 2A Ranitidin<br>No fever, no side-effects |
| 1 | | |
| 2 | | |
| 3 | 5 μg | Application via selective arterial port into A. hepatica dextra over 8 h<br>Premedication: dexa 20 mg, 2A Fenistil, 2A Ranitidin<br>Fever to 39.8° C. 9 h after the start of therapy<br>Medication with Metamizol 1A i.v. Temperature normalisation within 4 h |
| 4 | | |
| 5 | | |
| 6 | 20 μg | Application via selective arterial port into A. hepatica dextra over 8 h<br>Premedication: dexa 20 mg, 2A Fenistil, 2A Ranitidin<br>Fever to 39.6° C. 10 h after start of therapy<br>Medication with Metamizol 1A i.v. temperature normalisation within 4 h |
| 7 | | |
| 8 | | |
| 9 | | |
| 10 | 4 μg | Application via selective arterial port into A. hepatica dextra over 10 h<br>Premedication: dexa 20 mg, 2A Fenistil, 2A Ranitidin<br>Fever to 40.1° C. 6 h after start of therapy<br>Medication with Metamizol 2A i.v. Temperature normalisation within 10 h<br>Shivering/limb pains |

Under the combination, according to the invention, of the glucocorticoid with the immunotherapeutic antibody only a passing fever occurred, in which connection a normalisation of temperature occurred at the latest within 10 h of the maximum temperature being attained. Despite the very great increase in dose of the antibody by a factor of 40 (from 1 μg to 40 μg) during the therapy, no intensification, corresponding to this immense increase, of the side-effects of the immunostimulatory antibody was consequently established, which is to be ascribed to the administration, according to the invention, of the glucocorticoid. The administration of dexamethasone had no significant negative influence on the immunostimulating action of the antibody. This is documented by a systemic rise in the soluble IL-2 receptor and in the TNF receptors p55 and p75 (FIG. 8). In contrast, despite the increase in dose with respect to the antibody to a 40-fold figure no significant side-effects could be established. This is also confirmed, in particular, by the pancreas-specific and liver-specific laboratory parameters (FIG. 9).

The invention claimed is:

1. A method for reducing the non-specific release of at least one cytokine in a subject, which is associated with a treatment of a cancer with at least one bispecific immunostimulating antibody, comprising:
administering an effective amount of at least one glucocorticoid to the subject by way of premedication on the same day and prior in time relative to the administration to the subject of the at least one bispecific immunostimulating antibody directed against a tumor antigen and a CD marker such that said effective amount of said at least one glucocorticoid reduces cytokine release caused by the administration of the least one bispecific immunostimulating antibody,
wherein
the at least one glucocorticoid comprises dexamethasone,
the tumor antigen is CD19, and
the CD marker is CD3.

2. The method of claim 1, wherein the cancer is lymphoma.

3. The method of claim 1, wherein the at least one glucocorticoid is administered intravenously, intra-arterially or subcutaneously.

4. The method of claim 3, wherein the at least one glucocorticoid is administered intravenously.

5. The method of claim 1, wherein the at least one glucocorticoid comprises dexamethasone and at least one of prednisone, prednisolone, methylprednisolone, triamcinolone, betamethasone, cortisone acetate, prednylidene, deflazacort, cloprednol, fluocortolone and budenoside.

6. The method of claim 1, wherein the at least one cytokine comprises at least one of IL-6, TNF-alpha, and IFN-gamma.

7. The method of claim 1, wherein the at least one bispecific immunostimulating antibody and the at least one glucocorticoid are administered intravenously, intraperitoneally, intramuscularly, intradermally, intratumourally, or selectively into a defined organ.

8. The method of claim 1, wherein said effective amount of said at least one glucocorticoid is 1 mg to 1000 mg.

9. The method of claim 1, wherein the at least one bispecific immunostimulating antibody is administered intravenously, intra-arterially or subcutaneously.

10. The method of claim 1, wherein the at least one bispecific immunostimulating antibody comprises a bispecific immunostimulatory scFv antibody.

11. The method of claim 10, wherein the bispecific immunostimulatory scFv antibody is administered intravenously.

12. A method of permitting increased antibody administration during a cancer treatment of a subject comprising:
administering to the subject at least one glucocorticoid by way of premedication on the same day and prior in time relative to the administration to the subject of at least one recombinant bispecific immunostimulatory scFv antibody exhibiting a first specificity against the tumor antigen CD 19 and a second specificity against the T-cell marker CD3, wherein the at least one glucocorticoid reduces cytokine release caused by the administration of the at least one recombinant bispecific immunostimulating scFv antibody, and the at least one glucocorticoid comprises dexamethasone.

13. The method of claim 12, wherein the cancer is lymphoma.

14. The method of claim 12, wherein the at least one recombinant bispecific immunostimulatory scFv antibody is administered intravenously, intra-arterially or subcutaneously.

15. The method of claim 14, wherein the at least one recombinant bispecific immunostimulatory scFv antibody is administered intravenously.

16. The method of claim 12, wherein the at least one glucocorticoid is administered intravenously, intra-arterially or subcutaneously.

17. The method of claim 12, wherein the at least one glucocorticoid comprises dexamethasone and at least one of prednisone, prednisolone, methylprednisolone, triamcinolone, betamethasone, cortisone acetate, prednylidene, deflazacort, cloprednol, fluocortolone and budenoside.

18. The method of claim 12, wherein the cytokine comprises at least one of IL-6, TNF-alpha, and IFN-gamma.

19. The method of claim 12, wherein the administering to the subject at least one glucocorticoid by way of premedication comprises administering 1 mg to 1000 mg dexamethasone.

20. A method for reducing the non-specific release of at least one of IL-6, TNF-alpha, and IFN-gamma cytokines in a subject, which is associated with a treatment of a cancer with at least one recombinant bispecific immunostimulatory scFv antibody, comprising:

administering to the subject an effective amount of 1 mg to 1000 mg of at least one glucocorticoid by way of premedication on the same day and prior in time relative to the administration to the subject of at least one recombinant bispecific immunostimulatory scFv antibody exhibiting a first specificity against the tumor antigen CD 19 and a second specificity against the T-cell marker CD3, wherein said effective amount of the at least one glucocorticoid reduces cytokine release caused by the administration of the at least one recombinant bispecific immunostimulating scFv antibody, wherein said at least one glucocorticoid comprises dexamethasone.

* * * * *